(12) United States Patent
Patel et al.

(10) Patent No.: US 8,758,763 B2
(45) Date of Patent: Jun. 24, 2014

(54) ARCHAEAL POLAR LIPID AGGREGATES FOR ADMINISTRATION TO ANIMALS

(71) Applicant: National Research Council of Canada, Ottawa (CA)

(72) Inventors: Girishchandra B. Patel, Nepean (CA); Wangxue Chen, Nepean (CA)

(73) Assignee: National Research Council of Canada, Ontario (CA)

(*) Notice: Subject to any disclaimer, the term of this patent is extended or adjusted under 35 U.S.C. 154(b) by 0 days.

(21) Appl. No.: 13/748,412

(22) Filed: Jan. 23, 2013

(65) Prior Publication Data

US 2013/0195932 A1      Aug. 1, 2013

Related U.S. Application Data

(63) Continuation of application No. 11/956,653, filed on Dec. 14, 2007, now abandoned.

(60) Provisional application No. 60/875,305, filed on Dec. 15, 2006.

(51) Int. Cl.
*A61K 39/395*      (2006.01)

(52) U.S. Cl.
USPC ..................................................... 424/184.1

(58) Field of Classification Search
None
See application file for complete search history.

(56) References Cited

U.S. PATENT DOCUMENTS 6,153,217 A      11/2000      Jin et al.

FOREIGN PATENT DOCUMENTS

WO      WO0126683 A2      4/2001

OTHER PUBLICATIONS

Communication issued in EP 07855513 dated Jul. 11, 2012, 5 pages.
International Search Report and Written Opinion issued in PCT/CA2007/002231, mailed May 2, 2008, 10 pages.
Kanichay, Roby et al., "Calcium-induced aggregation of archaeal bipolar tetraether liposomes derived from the thermoacidophilic archaeon *Sulfolobus acidocaldarius*", Archaea, vol. 1, Jan. 1, 2003, pp. 175-183.
Patel, GB et al., "Archaeosome immunostimulatory vaccine delivery system", Current Drug Delivery, Oct. 2005, vol. 2 No. 4, pp. 407-421 (abstract only).
Patel, Girishchandra B. et al., "Mucosal and systemic immune responses by intranasal immunization using archaeal lipid-adjuvanted vaccines", Vaccine, vol. 25, No. 51, Dec. 12, 2007, pp. 8622-8636 (Abstract only).
Response dated Oct. 31, 2012 to Communication of Jul. 11, 2012 issued in EP07855513, 18 pages.
Supplementary European Search Report issued in EP Application No. 07855513, completed Feb. 18, 2011, 7 pages.

*Primary Examiner* — Yunsoo Kim
(74) *Attorney, Agent, or Firm* — Shelly Guest Cermak; Cermak Nakajima LLP

(57) ABSTRACT

The invention provides non-replicating compositions, and methods for the delivery of these compositions containing pharmaceuticals, biologically relevant molecules, and/or antigens to the host, by administration via a mucosal route such as the intranasal. This invention provides non-replicating vaccine compositions and methods for the delivery of antigens in these vaccine compositions comprising an antigen and a self-adjuvanting carrier, useful for inducing antigen-specific mucosal and systemic immune responses in the host upon immunization via a mucosal route such as intranasal. The vaccine compositions comprise multivalent cations in association with a plurality of spherical archaeal polar lipid aggregates containing aqueous compartments, the AMVAD structure, formed by the interaction of archaeosomes and antigen(s) with multivalent cations such as $Ca^{2+}$, wherein the AMVAD structure acts as a self-adjuvanting carrier for the antigen(s) in the vaccine composition. Certain advantageous immune responses can also be elicited with the subject compositions.

23 Claims, 33 Drawing Sheets

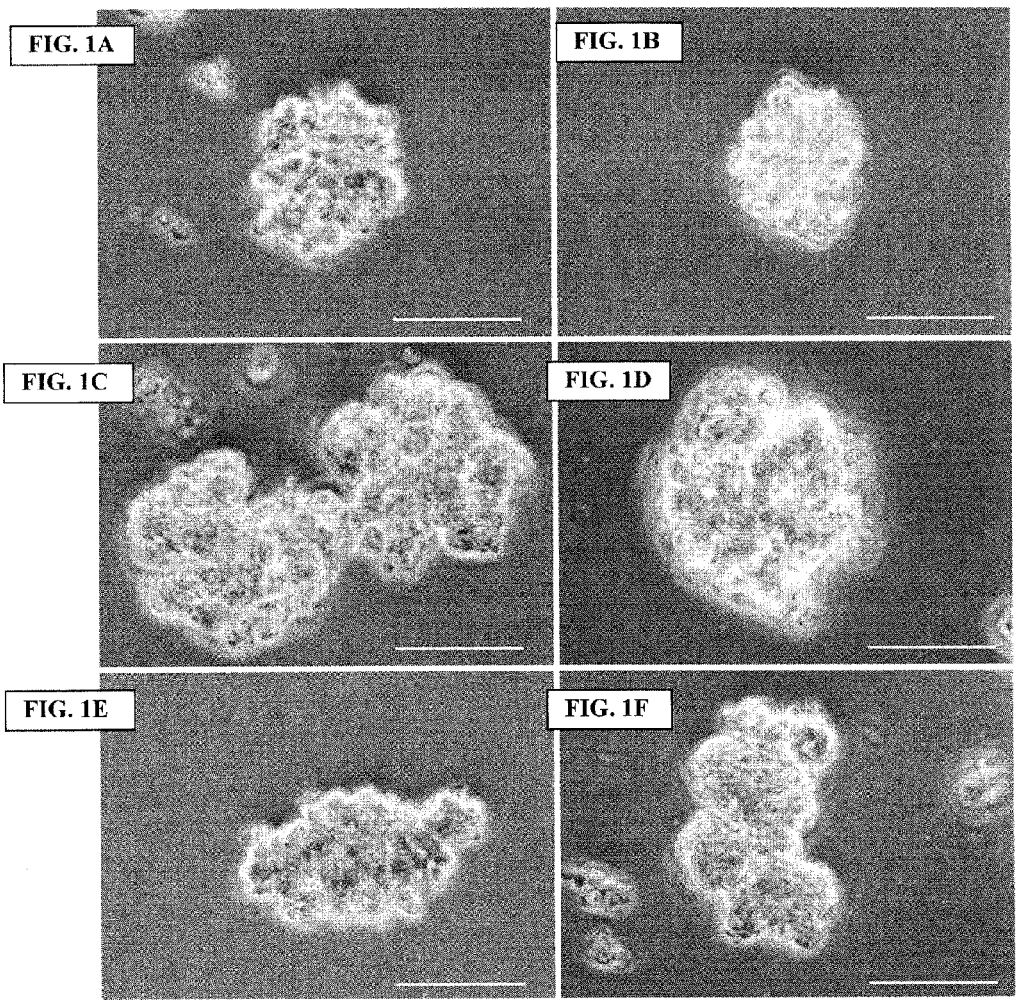

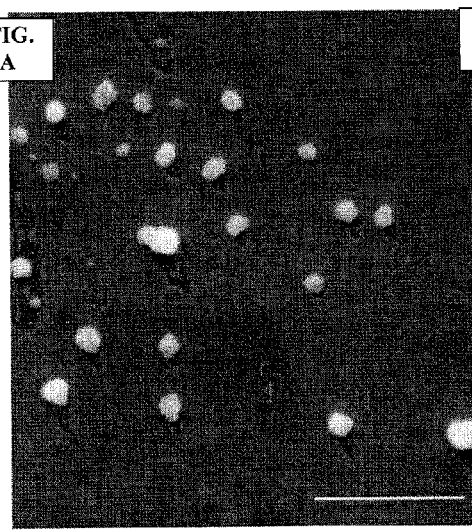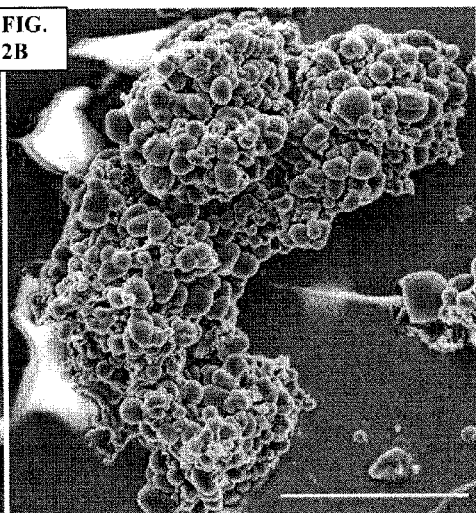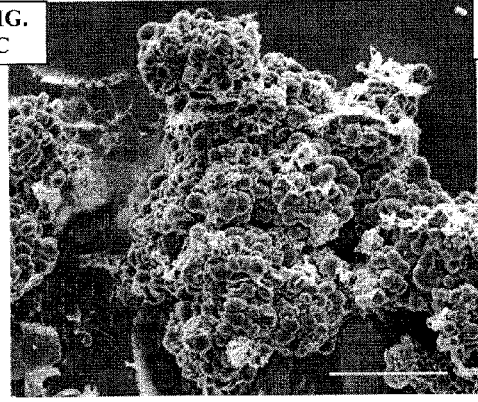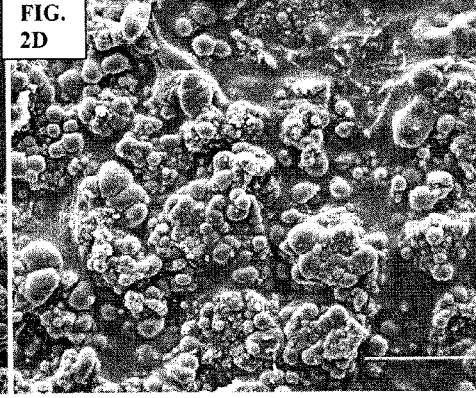

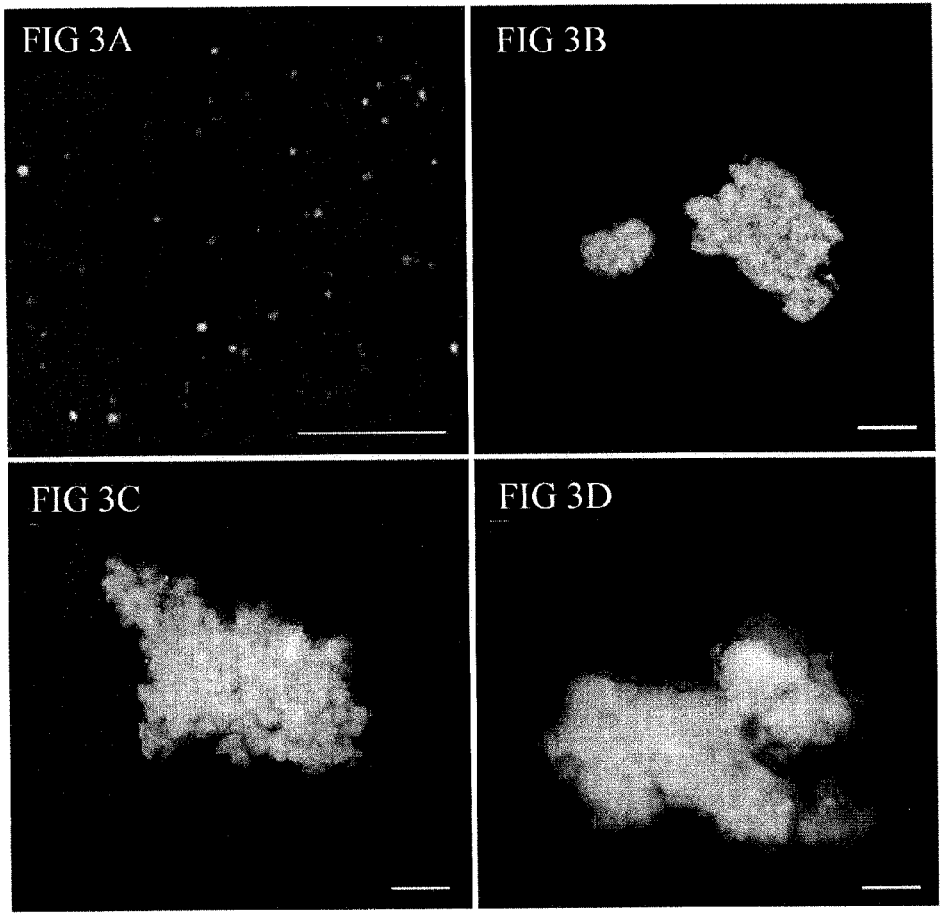

anti-BSA antibodies anti-OVA IgA

OVA/Ms AMVAD
OVA/Ms AMVAD-ANW
OVA/Ms AMVAD-NW
OVA⁻/Ms AMVAD
OVA/CaCl₂ anti-OVA serum antibodies

◨ OVA/Ms AMVAD
▦ OVA/Ms AMVAD-ANW
▦ OVA/Ms AMVAD-NW

▨ OVA⁻/Ms AMVAD
☐ OVA/CaCl$_2$ anti-OVA IgA

Fecal

Vaginal

Nasal

Bile

▤ OVA/Hs AMVAD  ☐ OVA/CaCl$_2$
▥ OVA/Hs AMVAD-ANW anti-OVA serum antibodies

OVA/Hs AMVAD
OVA/Hs AMVAD-ANW
OVA/CaCl$_2$ anti-OVA IgA

OVA/Ms AMVAD
OVA/Hs AMVAD
OVA/saline
OVA/Ms Arch (s.c.)

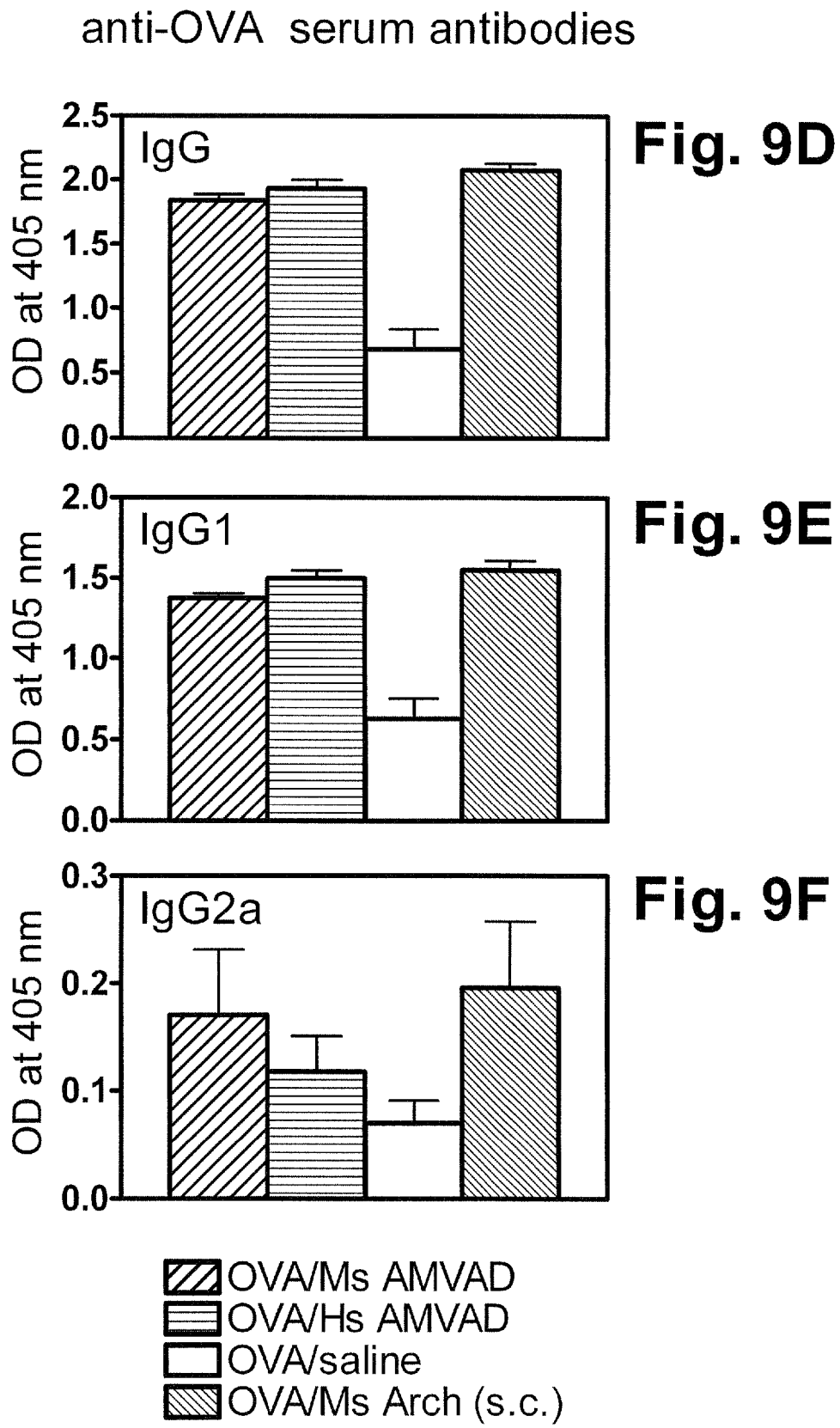

▲ OVA/Ms arch (s.c.)
■ OVA/Ms AMVAD (s.c.)
● OVA/Ms AMVAD (i.n.)
▼ saline/Ms AMVAD (i.n.)

anti-LVSCE antibodies

Bar charts showing OD at 405 nm for vaginal IgA, serum IgA, and serum IgG.

Legend:
- ☐ saline (no LVSCE)
- ||| 1 µg LVSCE/saline
- ⧄ 1 µg LVSCE/Ms AMVAD-ANW-SR

Fig. 19A

F. tularensis burden (35 d challenge)

lungs spleen

- saline (no LVSCE)
- ▲ 1 μg LVSCE/saline
- ■ 1 μg LVSCE/Ms AMVAD-ANW-SR

Fig. 19B

*F. tularensis* burden (77 d challenge)
lungs (scatter plot: Log$_{10}$ cfu, y-axis from 6.0 to 9.0)
$p < 0.001$ (saline vs LVSCE/Ms AMVAD-ANW-SR)
$p < 0.001$ (saline vs LVSCE/saline)
$p < 0.001$ (LVSCE/saline vs LVSCE/Ms AMVAD-ANW-SR)

spleen (scatter plot: Log$_{10}$ cfu, y-axis from 3.0 to 7.0)
$p < 0.01$ (saline vs LVSCE/Ms AMVAD-ANW-SR)
$p < 0.05$ (LVSCE/saline vs LVSCE/Ms AMVAD-ANW-SR)

- saline (no LVSCE)
- ▲ 1 µg LVSCE/saline
- ■ 1 µg LVSCE/Ms AMVAD-ANW-SR

Fig. 19C

Protection against i.n. LVS challenge

● saline (no LVSCE)
▲ 1 µg LVSCE/saline
■ 1 µg LVSCE/Ms AMVAD-SR

Fig. 20

ARCHAEAL POLAR LIPID AGGREGATES FOR ADMINISTRATION TO ANIMALS

CROSS-REFERENCE TO RELATED APPLICATION

This application is a Continuation of U.S. patent application Ser. No. 11/956,653, filed Dec. 14, 2007, which claims the benefit of provisional application Ser. No. 60/875,305, filed Dec. 15, 2006, both of which are incorporated herein by reference in their entireties for all purposes.

FIELD OF THE INVENTION

This invention relates in part to delivery of pharmaceuticals, biologically relevant molecules, and antigens to a host. It also relates to mucosal delivery, especially mucosal vaccine delivery. It relates to the use of vaccine compositions comprising archaeal polar lipid aggregates as mucosal vaccine delivery system for acellular (non-replicating), defined and mixed, antigens so as to elicit strong, protective, antigen-specific mucosal and antigen-specific systemic immune responses in the host, upon administration of the vaccine via mucosal routes. The invention also relates to the use of archaeal polar lipid aggregates as self-adjuvanting mucosal delivery systems for acellular antigens in vaccines administered via mucosal routes. Preferably, such administration elicits protective, antigen-specific systemic humoral and cell-mediated immune responses, in addition to antigen-specific mucosal immune responses in the vaccinated hosts. The invention relates to vaccine development for enhancing the mucosal immunity in the vaccinated host, for methods of treating and preventing infections and diseases such as those of microbial, protozoan, and viral origin that invade the host through the host's mucosal surfaces. The invention also relates to immunization of the host via the mucosal surface, to elicit antigen-specific mucosal or secretory IgA, systemic immune responses (such as IgG, IgG1, IgG2a), and cytotoxic T-cell responses that are known to be required for protecting the immunized host against infections, allergies, and neoplastic or cancer diseases.

BACKGROUND TO THE INVENTION

The mucosal surfaces in animals and humans, especially the gastrointestinal (GI) and respiratory tracts, are the major portals of entry and/or sites of diseases caused by bacterial, viral, and parasitic pathogens. Examples of these diseases include those caused by enteropathogenic *Escherichia coli*, *Campylobacter* sp., *Salmonella* sp., *Listeria monocytogenes*, *Helicobacter pylori*, *Shigella* sp., rotaviruses and caliciviruses in the gastrointestinal (GI) tract, and *Mycoplasma pneumoniae*, influenza virus, *Mycobacterium tuberculosis*, *Streptococcus pneumoniae*, severe acute respiratory syndrome (SARS) virus and respiratory syncytial virus in the respiratory tract. The urogenital tract is also a site of mucosal invasion/disease (e.g., those caused by human immunodeficiency virus, *Neisseria* and *Chlamydia*). The mucosal surfaces, especially in the respiratory tract, are also the sites where allergens (for example dust mites, pollen etc.) cause hyper immune responses resulting in allergic airway diseases such as asthma.

However, the majority of current, licensed, human and veterinary vaccines are administered parenterally or systemically (for example by subcutaneous, intramuscular, intraperitoneal routes), and although these elicit immunity in the systemic compartment (bone marrow, spleen and lymph nodes), they fail to elicit immunity in the functionally independent mucosal compartment (lymphoid tissues in the mucosae and external secretory glands). For example, the inactivated polio virus vaccine administered systemically may prevent the development of poliomyelitis, but it fails to prevent infection in the GI tract or in the tonsils.

Systemic immunization fails to induce mucosal IgA (Singh and O'Hagan, 2002). It is also acknowledged that vaccines that promote strong immune responses when given via the systemic route, may not be as successful if administered via the mucosal route (Neutra and Kozlowski, 2006). Conversely, mucosally administered vaccines that elicit mucosal immunity do not necessarily elicit systemic immunity also (Carol and Nieto, 1998).

Development of safe vaccines that elicit strong and prolonged mucosal immunity that would circumvent the attachment/colonization of pathogens to the mucosal epithelium, impede pathogen replication/penetration in the mucosa, and/or block activity of microbial toxins, would be a significant advancement in the prevention and treatment of a wide spectrum of infectious diseases. Also, mucosal immunity would be beneficial for elderly people since it is not subject to age-associated dysfunction, as well as for very young people since mucosal immunity appears to develop earlier than the systemic immunity (O'Hagan, 1998). This is a current, major, global aim in the field of vaccinology.

Furthermore, mucosal immunization can also be used for inducing immunological tolerance (immunologic hyporesponsiveness) and can serve as an attractive strategy for preventing or treating disorders resulting from untoward inflammatory immune reactions against self—(i.e., auto) or non-self-antigens, such as in type 1 diabetes, asthma, multiple sclerosis, autoimmune uveitis, and rheumatoid arthritis (see Ogra et al., 2001). Mucosal administration of relevant autoantigens and allergens on their own (in the absence of other known immune modulating components), has been shown to delay or suppress onset of clinical disease in a number of experimental autoimmune and allergic disorders. However, this approach often requires repeated feeding of large amounts of antigens over long periods and is only partly effective in the treatment of already established diseases. Mucosal administration of appropriately adjuvanted autoantigens has the potential to effectively suppress systemic auto-T cell reactivity and induce the selective migration and retention of protective/regulatory T cells into lymphoid tissues and organs involved.

It is understood that $CD8^+$ cytotoxic T-lymphocyte (CTL) responses involving participation of $CD8^+$ T cells are essential for host protection against intracellular pathogens since these cells are capable of killing the infected host cells. CTL responses are also known to be required for the killing of neoplastic host cells (Henkart, 1997; Singh and O'Hagan, 2002). Compared to the oral (per oral, p.o.) route, the intranasal (i.n.) route is generally more favourable and efficacious, and requires less dose of the immunogen since it does not have to encounter the relatively harsher environment of the gastrointestinal route (Davis, 2001; Lemoine et al., 1998; Singh and O'Hagan 2002).

Immune mechanism(s) to control infectious diseases requires the induction of neutralizing antibodies (humoral immunity) and generation of cell mediated immunity (CMI), including $CD4^+$ helper T (Th) cells, and $CD8^+$ cytotoxic (cytolytic) T lymphocytes (CTL). Naïve $CD8^+$ T cells are stimulated when peptides from endogenously derived antigens are presented in the context of MHC class I molecules. Although this process can occur virtually in all cells, only self-peptides, or peptides derived from viral or bacterial proteins being assembled within the host cell, are presented on MHC class I. Upon activation, naïve CD8+ T cells differentiate into effectors and memory T cells that possess the ability to kill infected target or tumor cells.

On the other hand, protein antigens from the extracellular fluids that are taken up by antigen presenting cells (APCs) through pinocytosis, or phagocytosis in the case of particulate antigens, are fragmented within endosomes. The peptides generated are presented by the APCs in the context of MHC class II molecules and stimulate CD4+ T cells. CD4+ T helper cells contribute towards control of infection primarily by producing cytokines that aid antibody responses, inflammation, macrophage activation, and CD8+ T cell proliferation (Krishnan and Mosmann, 1998).

The mammalian mucosal immune system comprises innate, non-specific defenses, and the adaptive immunologic network consisting of the gut-associated lymphoid tissue (GALT), bronchoepithelium and lower respiratory tract (BALT), ocular tissue, upper airway, tonsils, salivary glands and nasopharynx (NALT), and the larynx (LALT). There is some commonality in the mucosal immune network which has been referred to as the common mucosal immune system, and immunization at one mucosal surface has been shown to elicit immunity at a distal mucosal site. M-cells present in the epithelium of inductive mucosal sites (these sites are replete with B cells, T cells, dendritic cells, and also macrophages) are important in the transport of luminal antigens. Peyer's patches (PP) and NALT are the most commonly identified repositories of the M-cells. Secretory IgA (S-IgA) is the best-defined humoral effector component of the mucosal immune system; it is associated with M-cell-mediated antigen uptake. However, T lymphocytes of the CD4+ and CD8+ phenotypes and not IgA B cells, are the major effector cells present in the mucosal surfaces (Ogra et al., 2001).

Successful vaccination typically depends on two main criteria: identification of relevant antigenic target(s) for the pathogen or the disease, and the ability to evoke an appropriate protective or beneficial immune response, against the pathogen or the disease, in the vaccinated host. Some of the current research approaches for developing mucosal vaccines are based on the use of live-attenuated pathogens, or killed whole pathogen cells or components thereof, or the use of live viral/bacterial vectors (e.g. vaccinia, poxviruses, adenoviruses; *Salmonella*, BCG, *Bordetella*, commensal bacteria such as lactobacilli). Research approaches for non-replicating mucosal delivery vehicles and adjuvants have included heat shock proteins and microparticulates such as virosomes (reconstituted lipid vesicles consisting of viral glycoproteins), liposomes (closed lipidic vesicles made from ester lipids), cochleates (ester lipid liposomes converted into rolled up structures devoid of aqueous compartments by treatment with cations), polymeric microspheres, mucoadhesive polymers, ISCOMS (cage-like complexes consisting of glycosides of Quil A as the adjuvant in conjunction with phospholipids and cholesterol), virus like particles, CpG oligonucleotides and DNA as delivery/adjuvant systems, and the use of bacterial toxins such as cholera toxin (CT) and heat labile toxin (LT) from *E. coli* as potent mucosal adjuvants (Holmgren et al., 2003; Kemble and Greenberg, 2003; Lemoine et al., 1998; Ogra et al., 2001).

However, all of these approaches have drawbacks related to either safety, ease of preparation and/or efficacy. There are regulatory concerns regarding the use of ill-defined whole cell vaccines. The live attenuated pathogens may revert to virulence, especially posing a risk for the immuno-compromised population. There is potential for genetic integration between the attenuated and wild type strain that could result in creation of a more virulent strain. There maybe stronger immunity generated against the bacterial/viral vector than the antigen of interest, pre-existing immunity against the vector may reduce the efficacy of the vaccine in such pre-disposed population. There remain serious public/regulatory concerns regarding CpG and DNA vaccines (potential integration with the host DNA, tissue damage by CpG) in addition to issues concerning sustenance and duration of immunity generated. CT and LT holotoxins are highly toxic to most animals and humans, and their less toxic variants have diminished efficacies (Holmgren et al., 2003; Lemoine et al., 1998; Mestecky et al., 1997; Ogra et al., 2001). Some vaccines also require very complex methods for formulating. As a result, there are a few mucosal vaccines currently on the market, all using live-attenuated or dead whole cells.

Considerable progress has been made over the past decade using modern molecular biology and genomics approaches, towards the identification, purification and/or synthesis of key antigenic determinants of pathogens and non-pathogenic diseases such as tumors and allergies. However, such highly purified antigens (proteins and/or peptides, carbohydrates etc.) are relatively weak immunogens, limiting their ability to induce strong protective immune responses. Vaccines using acellular (non-replicating) subunit (purified or highly purified), antigens are preferred from safety and regulatory perspectives.

The poor immune responses of non-replicating antigen vaccines given mucosally is at least partially due to the lack of transport of the antigen through the epithelial layer to the mucosal immune network, and the rapid deactivation/elimination of the antigen (Jakobsen and Jonsdottir, 2003). This has continued to intensify global research aimed at developing safe and effective mucosal adjuvants, and effective mucosal vaccine delivery systems for elicitation of protective immunity. Some researchers have resorted to evaluating the use systemic prime/mucosal boost immunization strategy in order to elicit a stronger mucosal immune response (Lauterslager et al., 2003; O'Hagan, 1998). However, although there are many experimental mucosal adjuvants and mucosal delivery systems, none of these has been approved for commercial use to-date.

An adjuvant is recognized in the vaccine art as a substance or material which when administered together or in conjunction with an immunogen (antigen) increases the amount and quality of the immune response to that immunogen in the vaccinated/immunized host. Adjuvants are used in vaccine compositions to elicit an immune response sooner, or a greater response, or with less immunogen, or to increase or to suppress, production of certain antibody subclasses (potentiate the type of immune response desired for specific application) that afford immunological protection or to provide memory response to the immunogen, or to enhance/sustain components of the immune response.

Adjuvants may be further demarcated as being systemic and mucosal, based on the different physiological conditions of antigen delivery and processing that result in the generation of distinct immune responses. Mucosal vaccine adjuvants are those that are effective in eliciting of mucosal immunity, or systemic immunity, or mucosal as well as systemic immunity to an antigen in a vaccine that is administered via the mucosal route. Mucosal adjuvants can be broadly classified as those that play an immunostimulatory role (for example toxin-based, cytokine-based, innate immunity associated) and those that facilitate vaccine or antigen delivery (for example poly D,L-lactide-co-glycolide or PLGA, liposomes, cochleates, live-attenuated vectors, chitans, mucoadhesives, DNA vaccines) for the induction of a protective immunity (Holmgren at al., 2003; Ogra et al., 2001; Yuki and Kiyono, 2003).

The adjuvanticity (adjuvant activity) of mucosal adjuvants is partly manifested by their ability to help the antigen traverse the mucosal barrier imposed by the route of administration. Once the antigen has been assimilated, the adjuvant may impact the immunity by any of the recognized means in the art, such as complement activation, antigen adsorption and depot effect, induction of cytokines, presentation of the antigen to various antigen presenting cells (APCs), regulation of the expression through MHC class I or class II, stimulation of antibody production or antibody type switching (McElrath, 1995).

The bacterial protein enterotoxins of *Vibrio cholerae* (CT, cholera toxin) and of enterotoxicogenic *E. coli* (LT, heat labile enterotoxin) have been the most widely studied for development of mucosal vaccines. Although they are effective in eliciting of mucosal (e.g., IgA) as well as systemic immune responses (e.g. serum IgG), these holotoxins are too toxic for human/veterinary applications. On the other hand, their less toxic derivatives are not as effective (Arakawa et al., 1998; Holmgren et al., 2003; Ogra et al., 2001; Yuki and Kiyono, 2003).

Alum (aluminium hydroxide) is the only adjuvant currently approved universally for use in humans. However, it fails to elicit mucosal IgA antibodies upon p.o. or i.n. immunization (Alpar et al., 1992; Singh and O'Hagan, 2002). Thus, adjuvants that work for eliciting of systemic immunity may not be predictive for the elicitation of mucosal immunity.

For particulate or microparticulate mucosal delivery vehicles/carriers and adjuvants, it is recognized that the size of the particles has an impact on the type of immune response elicited. However, there is no clear consensus on the size ranges for optimal efficacy (Ogra et al., 2001; O'Hagan, 1998; Rubido et al., 2002).

Liposomes are closed, lipid vesicles containing an entrapped (encapsulated) aqueous volume. The hydrophilic polar head groups of the lipids forming liposomes are oriented towards the aqueous environment present inside and outside the liposome, whereas the hydrophobic "tail" region of the lipid is sandwiched between the polar head groups and away from the aqueous environment. Liposomes can vary in size from <50 nm to several micrometers in diameter, depending on the lipids used and the method of preparation. Depending on the methods used for making them, the liposomes can be unilamellar (one bilayer) or multilamellar (several bilayers with aqueous compartments between the adjacent bilayers).

Liposomes are well recognized in the art. Methods to encapsulate materials within the aqueous compartments of liposomes, and/or to associate with the hydrophobic lipid layer, are well known to those skilled in the art. These methods are exemplified by, but not limited to, detergent dialysis, dehydration-rehydration, reverse-phase evaporation, sonication, pressure extrusion, and remote loading. Liposomes composed predominantly of ester lipids, with or without additional components such as a sterol, are referred to herein as conventional liposomes or liposomes.

Liposomes on their own are not effective mucosal adjuvants, requiring the presence/association of additional known adjuvants or targeting molecules such cholera toxin B subunit, CT, dimethyl dioctadecyl ammonium bromide, or acemannan polysaccharide (Baca-Estrada et al., 2000; Harokopakis et al., 1998; Mestecky et al., 1997; Rubido et al., 2002; Vadolas et al., 1995), or they require high doses (1.6 mg/8-10 week old Balb/c mouse) of the liposomal lipid (de Haan et al., 1995) for efficacy. The addition of targeting molecules, on the surfaces of liposomes, specific to the mucosal epithelium to enhance the efficacy of mucosal delivery has also been suggested to improve the efficacy of liposomes as mucosal adjuvants (Mestecky et al., 1997; Ryan et al., 2001; Yuki and Kiyono, 2003).

Cochleate cylinders, formed via cation-induced (for example, $Ca^{2+}$ or $Mg^{2+}$) fusion of conventional phosphatidyl serine containing liposomes, were first described by Papahadjopoulos and colleagues, who used these as intermediate structures for conversion into large unilamellar liposomes by subsequent chelation of the added cations with EDTA (Papahadjopoulos, 1978; Papahadjopoulos et al., 1975). Later, others described various different methods for the interaction of cations for the conversion of conventional liposomes into cochleate structures, together with the incorporation/association of different molecules, and the application of the cochleates for the delivery of the said different molecules via various routes of administration. These disclosures are expressly incorporated herein by reference (Gould-Fogerite and Mannino, 1996, 1997, 1999; Gould-Fogerite et al., 1998; Mannino and Gould-Fogerite, 1998; Jin, 2004; Jin et al. 2000; Margolis et al., 2002; Zarif et al., 2003; Zarif and Tan, 2003).

These references are in agreement that the interaction of cations with negatively charged lipids, comprising liposomes made from conventional ester lipids, results in the conversion of the liposomes into cochleate cylinder structures. The cochleate structures consist of various sizes of continuous, solid, lipid bilayer sheets rolled up in a spiral (like a jelly roll). These structures are devoid of any internal aqueous spaces, and they appear as "needle like" structures under microscopic examination. These structures have also been referred to as nonaqueous structures. The average diameters of the cochleate cylinders can range from 40 nm to several μm (Jin, 2004; Mannino and Gould-Fogerite, 1998).

As such, cochleates are distinct from liposomes which are individual, spherical, closed vesicles which essentially do contain encapsulated internal aqueous compartment(s). In liposomes, water soluble molecules are encapsulated within the aqueous compartment(s) and hydrophobic molecules can be associated with the hydrophobic tail region of the lipid bilayer where it can be entirely within the hydrophobic region and/or could be exposed on the outer surface of the vesicle or oriented inside towards the encapsulated aqueous compartment. In cochleates, the molecules of interest for delivery purposes are entrapped within the rolled up lipid bilayer sheets.

It is recognized that the lipids used for making the liposomes need to have a net negative charge for the subsequent interaction with the added cations for conversion to cochleates. In addition, although lipids that are negatively charged by the presence of phosphatidyl serine head groups are amenable for cochleate formation, not all negatively charged lipids/liposomes could be converted into cochleates (Papahadjopoulos, 1978; Gould-Fogerite et al., 1998). Moreover, some lipids needed to be purified to at least 75% enrichment of phosphatidyl serine (by weight), in order for being able to convert the liposomes made therefrom into cochleates cylinders (Zarif and Tan, 2003). For preparation of cochleates from ester lipids (which in many instances contain some degree of unsaturation in their fatty acyl chains), the cochleate manufacturing process is conducted under an inert gas such as nitrogen, and the cochleates are stored under an inert gas (Jin, 2004; Jin et al., 2000; Zarif et al., 2003) to avoid potential stability- and toxicity-related problems associated with lipid oxidation.

The conversion of conventional liposomes to cochleates is mediated by cation-induced fusion of the vesicles (Jin, 2004;

Margolis et al., 2002; Papahadjopoulos 1978). It has been reported that the conversion of conventional liposomes into cochleate structures by addition of divalent cations such as $Ca^{2+}$ required incubation periods of from one to several hours (Papahadjopoulos, 1978; Papahadjopoulos et al., 1977). For making cochleates from conventional liposomes, a molar concentration of $Ca^{2+}$ that is up to one half the molar concentration of the lipids/phospholipids (that is, the molar ratio of lipids to cations of 1:0.5) is required (Gould-Fogerite et al., 1998; Margolis et al., 2002).

More recently, cationic organic drugs have been used to directly convert conventional liposomes into cochleates and entrap the drug, rather than using cations to form cochleates from liposomes (Jin, 2004). Several methods have been described in the literature, for preparation of cochleate formulations, incorporating different means of adding cations to liposomes to convert them into cochleates (Jin, 2004; Jin et al., 2000; Papahadjopoulos, 1978; Papahadjopoulos et al., 1975; Zarif et al., 2001, 2003; Gould-Fogerite, S., and Mannino, 2000). These methods have been referred to variously as standard cochleates (liposomes are pre-formed by hydration/sonication of lipids followed by either direct addition of calcium or infusion of calcium via dialysis against a calcium containing buffer), DC cochleates (infusion of calcium at the same time as liposomes are being formed by detergent dialysis process), LC cochleates (liposomes made by detergent dialysis followed by calcium addition separately), hydrogel-isolated cochleate (liposomes with the loaded components are added to a polymer A which is then mixed with another polymer B in which polymer A is not miscible, resulting in an aqueous two-phase system to which is then added a cation salt so that it diffuses into the polymer A containing liposomes.

In all these methods, except the one where the molecule of interest is a cationic molecule added directly to empty pre-formed liposomes to make cochleates (Jin, 2004), the molecule of interest is first encapsulated/associated with the liposomes, and the cation is added without prior removal of the un-encapsulated (or material not associated with the liposomes) molecules present in the external milieu, raising the strong possibility that there could be substantial amounts of the molecule present in the formulation as a cation-precipitate, besides that entrapped in the cochleate structures. This external precipitated material is mostly left with the cochleate formulation since there is no simple way to remove this from the rest of the cochleate which also is a precipitate. In addition, the presence of this material in the formulation could have a significant impact on the observed biological effects of molecule delivered using the so called cochleate formulation. One skilled in the art will recognize that there are various means such as for example ultracentrifugation or dialysis using an appropriate molecular weight cut off, to allow escape of the un-encapsulated molecules from the liposome preparation, before addition of the cation to make cochleates, so as to avoid the possibility of cation-precipitated molecule being present in the formulation. One skilled in the art will also recognize that there could be many other means for addition of cations to liposomes to convert them into cochleate structures. One skilled in the art will also appreciate that any molecule of interest, whether it is hydrophilic or hydrophobic in characteristic, can be entrapped/associated in/with cochleate structures.

Lipids amenable for cochleate formation can be obtained from animal or plant membranes (Mannino and Gould-Fogerite, 1998), but there is no suggestion or mention that lipids obtained from the membranes of microorganisms, in the absence of other bacterial components such as membrane proteins and lipopolysaccharides (LPS), would be amenable for cochleate formation. Cochleates have recently been made from lipid-containing outer membrane extracts of *Neisseria meningitides*, but these extracts also contained major outer membrane proteins and LPS (Bracho et al., 2006; Campo et al., 2006; Perez et al., 2006). The advantages of cochleates as delivery vehicles, compared to the liposomes from which they have been converted from, have been attributed to improved stability properties of these structures, the protection of the associated biological molecules from the external environment, and the ability to store lyophilized cochleate preparations that can be re-hydrated just prior to use without loss of the associated biological molecules (Mannino and Gould-Fogerite, 1998; Margolis et al., 2002; Zarif et al., 2003).

Cochleates with associated drugs and other bioactive molecules, including antigens, have been shown to be useful for the delivery of these compounds in murine models (Gould-Fogerite et al., 1998; Gould-Fogerite and Mannino, 1999; Jin et al., 2000; Margolis et al., 2002; Zarif et al., 2003). The use of cochleates for delivery of antigens in vaccine applications has been described for vaccines administered by parenteral (such as i.m.), per oral (p.o.) or a combination of both routes (Gould-Fogerite and Mannino, 1996; Gould-Fogerite et al., 1998; Gould-Fogerite et al., 1997; Jin et al., 2000).

Cochleate/protein vaccines (synthetic lipid dioleyl phosphatidylserine having 18-carbon acyl chains and one unsaturated bond was used as the negatively charged lipid for making the formulation) administered p.o. or i.m. were stated to elicit strong circulating mucosal antibodies, but no data were given to illustrate this, to be able to discern the level of immune response (Gould-Fogerite and Mannino, 1996). The paper also stated that i.n. administration elicited circulating antibodies but did not specify what subtype the antibodies were, and did not mention or suggest that any of the antibodies were of the IgA isotype indicative of a mucosal immune response.

It has been previously reported that i.n. immunization with vaccine wherein the antigen is associated with polymeric particles, may elicit an increase in the circulating antibodies of the IgG isotype but not of the IgA isotype (Lemoine et al., 1998). This shows that the mere mentioning of elicitation of circulating antibodies without identifying the specific mucosal suggestive antibody subtype is not indicative of the elicitation of a mucosal immunity.

Administration of protein- or glycoprotein/cochleates vaccines via p.o. or i.m. routes were reported to elicit specific serum IgA responses, especially after the second immunization (Gould-Fogerite et al., 1998). In most other experimental vaccines, systemic immunization fails to elicit an IgA response (Singh and O'Hagan, 2002), and systemic immunization fails to generate protective immunity at the mucosal surfaces (Yuki and Kiyono, 2003).

The p.o. and i.m. immunization with PS-cochleate/glycoprotein vaccine elicited antigen specific serum IgG1 and IgG2a responses also, as did the corresponding PS-liposome vaccine (Gould-Fogerite et al., 1998). This paper also reported that the serum IgA antibody response upon p.o. immunization with PS-liposomes containing glycoproteins was similar or greater than that obtained with corresponding PS-cochleates-glycoproteins.

It was reported that the immune responses obtained with the cochleate vaccine formulations administered p.o. or i.m. were slower to develop than those obtained with liposomes, but the cochleate vaccine responses kept on steadily increasing for a period of several months after immunization (Gould-Fogerite et al., 1998; Gould-Fogerite and Mannino, 1996). Although immune response data are given for cochleate vaccines administered via the p.o., i.m. or a combination of both routes, there was no indication or suggestion of the elicitation of a mucosal immune response upon i.n. administration (Gould-Fogerite and Mannino, 1997). There are differences in the adsorption of the antigen administered via the p.o. and the nasopharyngeal routes such as i.n. In addition, an adjuvant effective via the p.o. route is not predictive of its efficacy by the nasopharyngeal route (Rubido et al., 2002).

Elicitation of anti-OVA IgA responses in saliva, but not serum IgG responses, were recently reported upon i.n. immunization of mice with OVA formulated in cochleates made from proteoliposomes consisting of outer membrane proteins, lipids and LPS extracted from *N. meningitidis* (Bracho et al., 2006). However, it has been reported that mucosal IgA and systemic IgG immune responses are elicited against the proteoliposome components of these cochleates (Campo et al., 2006; Perez et al., 2006), raising concerns about the efficacy of such cochleates for use in subsequent immunizations due to the pre-existing immunity against the carrier. Also, it should be noted that the LPS (an endotoxin) in these cochleates is a known immunostimulating molecule.

*Archaea* is a Domain of microorganisms that is considered to be distinct from the two Domains constituting eubacteria and eukaryotes. *Archaea* includes aerobic, anaerobic (including methanogenic), thermophilic, extremely thermophilic, thermoacidophilic, and extremely halophilic microorganisms. The unique polar lipid structures of archaeal membranes are one of the key, unique defining characteristic that helps distinguish members of *Archaea* from species of the other two domains. The total lipids extracted from archaeal species consist of between 80-95% polar lipids, the balance being neutral lipids.

Archaeal polar lipids are composed of branched phytanyl chains, usually of constant length, which are fully saturated in most species. They are uniquely attached via ether bonds to the glycerol backbone carbons at the sn-2,3 positions (Kates, 1992). In contrast, conventional ester phospholipids found in members of the domains Bacteria and Eukarya have fatty acyl chains of variable length, which may be unsaturated, and these are distinctly attached via ester bonds to the sn-1,2 carbons of the glycerol.

The core structures of archaeal polar lipids (the polar head groups having been removed by hydrolysis) consist of the standard archaeol (also referred as diether) lipids (2,3-di-O-phytanyl-sn-glycerol) and/or the standard caldarchaeol (also referred as tetraether) lipids (2,2',3,3'-tetra-O-dibiphytanyl-sn-diglycerol) and modifications thereof (Kates, 1992). Diether lipids are monopolar like the conventional ester phospholipids, whereas the tetraether lipids are bipolar. The polar head groups, attached to the sn-1 glycerol carbon in the archaeols and to the sn-1 and sn-1' glycerol carbons in the caldarchaeols, can vary and may include phospho groups, glyco groups, phosphoglyco groups, polyol groups, or hydroxy groups.

The phosphatidylcholine head group commonly encountered in conventional ester lipids is rarely found in archaeal polar lipids. The total polar lipids extracted from archaeal species are negatively charged due to the preponderance of negatively charged polar head groups (Sprott, 1992). The total polar lipids extracted from some archaeal species such as *Halobacterium salinarum* consist entirely of archaeol type of core lipids, others such as from *Methanobrevibacter smithii* consist of a mixture of archaeol and caldarchaeol, whereas those from others such as *Thermoplasma acidophilum* consist predominantly of caldarchaeol cores (reviewed in Patel and Sprott, 1999).

The total lipid extract (contains neutral and the polar lipids), total polar lipid extract or purified polar lipids from archaeal species can be made into liposomes, which are referred to as archaeosomes (reviewed in Patel and Sprott, 1999). Archaeosomes prepared from polar lipids consisting exclusively of archaeol type cores, form a bilayer vesicle membrane as observed with conventional liposomes. Those made from polar lipids consisting exclusively of caldarchaeol type cores form a monolayer membrane that spans the entire vesicle membrane. Those made from polar lipids consisting of mixtures of both archaeol and caldarchaeol type cores form a vesicle membrane consisting of both mono- and bilayer membrane (Patel and Sprott, 1999).

In earlier studies, it was reported that archaeosomes elicit antigen-specific humoral antibody (Th2) and cell-mediated (Th1) immune responses, including $CD8^+$ cytotoxic T lymphocyte (CTL) responses, to entrapped antigens upon immunization of the host by parenteral routes such as i.p., s.c. and i.m. (reviewed in Patel and Chen 2005; Sprott et al., 2000, 2001). Further, there has been no prior suggestion or indication that such archaeosome vaccines would be capable of eliciting mucosal immunity upon systemic or mucosal route of vaccine delivery. Prior art has indicated that adjuvants that help elicitation of systemic immune responses are generally incapable of eliciting mucosal responses upon administration of the vaccine by a mucosal route (Ryan et al., 2001; Singh and O'Hagan, 2002).

The citation of above references is not an admission that any of the foregoing is pertinent prior art. Representations as to the contents of these references and as to the dates of publication are based on the information available to the applicants and do not constitute any admissions as to correctness of the contents or the dates of the said references.

SUMMARY OF THE INVENTION

Surprisingly and unexpectedly, it was presently discovered that by addition of multivalent cations or multivalent organic cationic compounds, archaeosomes can be formulated into structures comprising aggregates of individual, larger, spherical structures with aqueous compartments, referred to herein as archaeal lipid mucosal vaccine adjuvant and delivery (AMVAD) structures. It was also discovered that vaccine compositions consisting of antigens formulated into AMVAD structures elicited strong, sustained, and protective antigen-specific mucosal immunity upon administration (that is vaccination or immunization) to the host via a mucosal route such as the i.n. route. In addition to the mucosal immunity elicited at the immunization site and at other distal mucosal surfaces, strong systemic immune responses (humoral antibody and cell-mediated responses including antigen-specific $CD8^+$ CTL responses) were also elicited by these formulations. The mucosal and systemic immune responses were sustained for a period of several months, and were subject to strong memory responses upon antigen alone boost. However, although systemic immunization with the AMVAD vaccine formulation elicited strong systemic immune responses, there was little to no elicitation of mucosal immune responses. In addition to strong, sustained mucosal and serum antigen-specific IgA antibody responses, the AMVAD vaccine formulation can elicit robust and sustained systemic antibody responses (serum IgG, IgG1, IgG2a) upon intranasal administration to the host. Additionally, strong antigen-specific CTL responses can also be elicited. All of these immune responses exhibit strong memory responses upon a booster immunization with the antigen alone. The invention provides methods for providing protective immunity in the vaccinated host against infections caused by mucosal pathogens, and in the treatment of disease conditions that are known to be mitigated by the elicitation of such immune responses. Compositions of the invention are also useful for eliciting systemic immune responses by systemic immunization, showing utility for systemic immunization for protection against pathogens/diseases requiring such host-immune responses for protection.

Structures formed from the archaeosomes by addition of multivalent cations are referred to herein as AMVAD structures. The formulation is referred to as an AMVAD vaccine when it is co-formulated with an antigen. In contrast, the cochleate structures obtained by addition of multivalent cations to conventional liposomes are folded, cylindrical, jelly-roll like bilayer structures which possess no aqueous compartments. Also, unlike cochleates where the required molar ratio of the lipid to the divalent cation ($Ca^+$) is 1:0.5 (Margolis et al., 2002; Papahadjopoulos et al., 1977) for converting liposomes into cochleates, the molar ratio of polar lipid to $Ca^+$ for making AMVAD structures is higher—typically much higher—and typically in the range of 1:1 and higher. At a molar ratio of 1:0.5, most of the archaeosomes are present as individual, small, non-aggregated vesicles which have average diameters in the nanometer range rather than micrometers.

In some embodiments, the subject invention utilizes archaeal polar lipid/cation mucosal adjuvant and mucosal vaccine delivery structures, referred to herein as the AMVAD structures. The subject AMVAD structure can be used as novel carriers for delivery of pharmaceuticals, biologically relevant molecules, and antigens to the host by administration to the host via the mucosal route, and more particularly by the intranasal route.

Some embodiments of this invention utilize an AMVAD structure as a novel, self-adjuvanting carrier for antigens in acellular (non-replicating) vaccine formulations delivered by the mucosal route, and more particularly by the intranasal route, to elicit antigen-specific immunity or an immune response in the vaccinated host. In some embodiments, the immunity is antigen-specific mucosal immunity in the vaccinated host. In some embodiments, the immunity is antigen-specific systemic immunity. In some embodiments, an AMVAD structure is used to elicit antigen-specific mucosal and systemic immunity in the vaccinated host.

In some embodiments where an antigen-specific mucosal immunity is elicited in the vaccinated host, the archaeal polar lipid extract is a polar lipid extract from an archaeal species (archaeobacterium). In some embodiments, the archaeal polar lipid extract from the archaeal species is a single polar lipid extracted in a biologically pure form from the archaeal species. In some embodiments, the archaeal polar lipid extract is the total polar lipid extract. In some embodiments, the total polar lipid extract is extracted from the group consisting of *Methanobrevibacter smithii*, *Thermoplasma acidophilum*, or *Halobacterium salinarum*.

In some embodiments of the subject invention, an AMVAD structure is used as a novel, self-adjuvanting carrier for antigens in acellular (non-replicating) vaccine formulations delivered by the mucosal route, and more particularly by the intranasal route, wherein the systemic immunity elicited is an antigen-specific $CD8^+$ CTL immunity.

In still further embodiments, the subject AMVAD structures are used to elicit antigen-specific systemic immunity in addition to the antigen-specific mucosal immunity in the vaccinated host, the immunity elicited being characterized by a strong elicitation of antigen-specific nasal IgA, vaginal IgA, fecal IgA, bile IgA, and serum IgA, IgG, IgG1, and IgG2a antibodies.

In some embodiments where mucosal and/or systemic immunity is elicited, the immunity can be sustained for a substantial portion of the life span of the vaccinated host.

In some embodiments where (antigen-specific) mucosal and/or systemic immunity is elicited, the immunity response can be subject to a strong memory response upon antigen alone boost via the mucosal route.

The elicited antigen-specific $CD8^+$ CTL response can also be subject to a strong memory boost response upon antigen alone boost via the mucosal route.

The subject AMVAD structures can be used for therapies against diseases caused by pathogens, toxins, autoantigens, allergens, and against cancer, tumor or neoplastic cells/diseases. Thus, the subject structures can be used to protect the vaccinated host against an infection caused by a pathogen.

According to a further aspect of the invention, a method is provided for conferring to an animal protective immunity against infection by a pathogen, comprising administering to the animal a vaccine composition comprising an AMVAD structure prepared from the total polar lipids extract of an archaeal species and an antigen, via a mucosal route, and more preferably by the intranasal route, wherein the AMVAD structure acts as a self-adjuvanting carrier for the antigen.

According to yet a further aspect of the invention, a method is provided for immunizing an animal by a mucosal route, more preferably by the intranasal route, to confer to the said animal a memory response against infection by a pathogen, comprising administering to the animal a vaccine composition comprising an AMVAD structure prepared from the total polar lipids extract of an archaeal species and an antigen, wherein the AMVAD structure acts as a self-adjuvanting carrier for the antigen.

According to another aspect of the invention, a method is provided for immunizing an animal by a mucosal route, and more preferably by the intranasal route, for eliciting an antigen specific MHC class I-restricted cytotoxic T lymphocyte response and an antigen specific MHC class II-restricted Th 1 and Th 2 response in an animal, comprising administering to the animal a vaccine composition comprising an AMVAD structure prepared from the total polar lipids extract of an archaeal species and an antigen, wherein the AMVAD structure acts as a self-adjuvanting carrier for the antigen.

Another aspect of this invention includes utilizing an AMVAD structure as novel, self-adjuvanting carrier for antigens in acellular (non-replicating) vaccine formulations delivered by the mucosal route, and more particularly by the intranasal route, wherein the vaccinated host is protected against an infection caused by a pathogen, wherein the pathogen primarily enters/invades the host via a mucosal surface.

According to one aspect of the invention a method is provided for eliciting antigen-specific mucosal, and antigen-specific cytotoxic T lymphocyte (CTL) immune responses in an animal, comprising administering to the animal a vaccine composition comprising an AMVAD structure and an antigen, wherein the AMVAD structure acts as a self-adjuvanting carrier for the antigen.

According to yet a further aspect of the invention, a method is provided for stimulating the elicitation of antigen-specific IgA antibody responses at mucosal surfaces, comprising administering to the animal a vaccine composition comprising an AMVAD structure and an antigen, wherein the AMVAD structure acts as a self-adjuvanting carrier for the antigen.

Thus, the subject invention includes utilizing an AMVAD structure as a novel, self-adjuvanting carrier for antigens in acellular (non-replicating) vaccine formulations delivered by the systemic route, to elicit antigen-specific systemic immunity in the vaccinated host. The subject invention also includes methods for making vaccine formulations comprising an AMVAD structure and an antigen, for immunization of the host for elicitation of antigen-specific mucosal and systemic immunity, wherein the method to make the AMVAD/antigen vaccine formulation comprises interaction of closed vesicles made from archaeal polar lipid, an antigen and a positively charged ion such as a cation.

BRIEF DESCRIPTION OF THE DRAWINGS

FIG. 1A shows a typical example of a phase contrast observation of empty Ms AMVAD prepared by the standard protocols described in Example 3. FIG. 1B shows a typical example of a phase contrast observation of OVA/Ms AMVAD prepared by the standard protocols described in Example 3. FIG. 1C shows a typical example of a phase contrast observation of empty Hs AMVAD prepared by the standard protocols described in Example 3. FIG. 1D shows a typical example of a phase contrast observation of OVA Hs AMVAD prepared by the standard protocols described in Example 3. FIG. 1E shows a typical example of a phase contrast observation of OVA/Ms AMVAD-ANW prepared by the admixing protocols as described in Example 5. FIG. 1F shows a typical example of a phase contrast observation of OVA/Hs AMVAD-ANW prepared by the admixing protocols as described in Example 5. Under phase contrast light microscopy, the typical AMVAD structure (FIG. 1A-1F) has a phase light perimeter, with some phase light areas within the structure. The figures show that Ms and Hs AMVAD formulations prepared by the different methods have similar appearance under phase contrast microscopy. The bar in each figure equals 20 μm.

FIG. 2A shows a typical observation, by scanning electron microscopy as described in Example 8, of Ms archaeosome formulation prepared by the standard protocols in Example 3. FIG. 2B shows a typical observation, by scanning electron microscopy as described in Example 8, of empty Ms AMVAD formulation prepared by the standard protocols in Example 3. FIG. 2C shows a typical observation, by scanning electron microscopy as described in Example 8, of OVA/Ms AMVAD formulation prepared by the standard protocols in Example 3. FIG. 2D shows a typical observation, by scanning electron microscopy as described in Example 8, of OVA/Hs AMVAD formulation prepared by the standard protocols in Example 3. It is seen that unlike the small, individual, spherical vesicle structures seen in the archaeosome formulation (A), the AMVAD formulations are composed of much larger spherical structures that have aggregated into clumps that appear similar to a bunch of grapes. Bar equals to 1 μm in FIG. 2A and 20 μm in FIGS. 2B-2D.

FIG. 3A shows a typical fluorescence microscopy observation of CF/Ms archaeosome formulation prepared as described in Example 9. FIG. 3B shows a typical fluorescence microscopy observation of CF/Ms AMVAD formulation prepared as described in Example 9. FIG. 3C shows a typical fluorescence microscopy observation of Ms AMVAD-ACF formulation prepared as described in Example 9. FIG. 3D shows a typical fluorescence microscopy observation of Hs AMVAD-ACF formulation prepared as described in Example 9. The archaeosomes with encapsulated carboxyfluorescein (CF) dye appear as fluorescent, individual, small, spherical structures that are barely visible at the ca 1250× magnification of the microscope. The AMVAD structures (FIG. 3B-3D) appear as larger fluorescent structures. Bar equals 20 μm in each figure.

FIG. 6A shows the anti-BSA fecal IgA titres (mean OD±SD) at 28 d and 204 d. FIG. 6B shows the anti-BSA serum IgA titres (mean OD±SD) at 28 d and 204 d. FIG. 6C shows the anti-BSA serum IgG titres (mean OD±SD) at 28 d and 204 d. The anti-BSA fecal IgA, serum IgA and serum IgG titres (mean OD±SD) at 28 d and 204 d in the mouse group immunized with BSA/Ms AMVAD in PBS (0, 7, 21 d, 10 μg BSA/immunization) are strong and generally well sustained. The group which received BSA alone in PBS had little to no measurable immune responses.

FIG. 9D shows elicitation of anti-OVA serum IgG titres (mean OD±SD) at 28 d, upon i.n. immunization (0, 7, 21 d) of groups of C57BL/6 mice with OVA (10 μg/immunization) formulated with Ms AMVAD (OVA/Ms AMVAD) or Hs AMVAD (OVA/Hs AMVAD) vaccines prepared as described in Example 3. FIG. 9E shows elicitation of anti-OVA serum IgG1 titres (mean OD±SD) at 28 d, upon i.n. immunization (0, 7, 21 d) of groups of C57BL/6 mice with OVA (10 μg/immunization) formulated with Ms AMVAD (OVA/Ms AMVAD) or Hs AMVAD (OVA/Hs AMVAD) vaccines prepared as described in Example 3. FIG. 9F shows elicitation of anti-OVA serum IgG2a titres (mean OD±SD) at 28 d, upon i.n. immunization (0, 7, 21 d) of groups of C57BL/6 mice with OVA (10 μg/immunization) formulated with Ms AMVAD (OVA/Ms AMVAD) or Hs AMVAD (OVA/Hs AMVAD) vaccines prepared as described in Example 3. One control group was similarly i.n. immunized with OVA/saline. A second control group was s.c. immunized at 0 and 21 d with OVA/Ms archaeosomes (OVA/Ms arch) prepared as described in Example 2, as a positive control for subsequent CTL assays. The results show that mucosal and systemic immune responses were also elicited in C57BL/6 mice, upon i.n. immunization with AMVAD vaccines.

In FIG. 11A, it is seen that at 234 d, only the OVA/Ms archaeosome group had a measurable CTL response but in FIG. 11B, it is seen that at 39-d post-antigen alone boost, there is a measurable increase (boost) in the CTL response in both, the i.n. and the s.c. OVA/Ms AMVAD immunized groups. There is no CTL response seen in the group immunized with empty Ms AMVAD.

FIG. 19A shows anti-LVSCE vaginal and serum IgA, and serum IgG antibody responses at 28 d upon i.n immunization (0, 7, 21 d, 50 μl immunization volume) of groups of Balb/c mice (n=10) with saline (saline, no LVSCE), 1 μg LVSCE/saline or 1 μg LVSCE/Ms AMVAD-ANW-SR formulation. The antibody responses with the LVSCE/Ms AMVAD-ANW-SR vaccine are much higher than those observed with the LVSCE/saline immunization. There were no measurable anti-LVSCE antibody responses in mice immunized with only saline. FIGS. 19B and 19C show the pathogen burdens in the lungs and spleen of mice (n=5) at 3 days post i.n. challenge at 35 d with $2.8 \times 10^5$ CFU of *F. tularensis* LVS or at 77 d with $2.0 \times 10^5$ CFU of *F. tularensis* LVS respectively, in each of the three immunized groups in FIG. 19A. These results show that the pathogen burdens in lungs and spleen of LVSCE/Ms AMVAD-ANW-SR vaccinated group are overall significantly lower than in the corresponding organs from of LVSCE/saline- or saline-immunized mice, respectively ($p<0.05$ to $p<0.001$).

FIG. 20 shows the % survival in groups of Balb/c mice (n=10) intranasally immunized with saline (saline, no LVSCE), 1 μg LVSCE/saline or 1 μg LVSCE/Ms AMVAD-ANW-SR formulations as described in FIG. 19, and intransally challenged at 35 d with 2.8×10⁵ CFU of *F. tularensis* LVS. The results show that mice immunized with the LVSCE/AMVAD-SR vaccine had substantially prolonged survival post-challenge, compared with the mice immunized with saline or LVSCE/saline.

DETAILED DESCRIPTION OF THE INVENTION

Figure 4A:
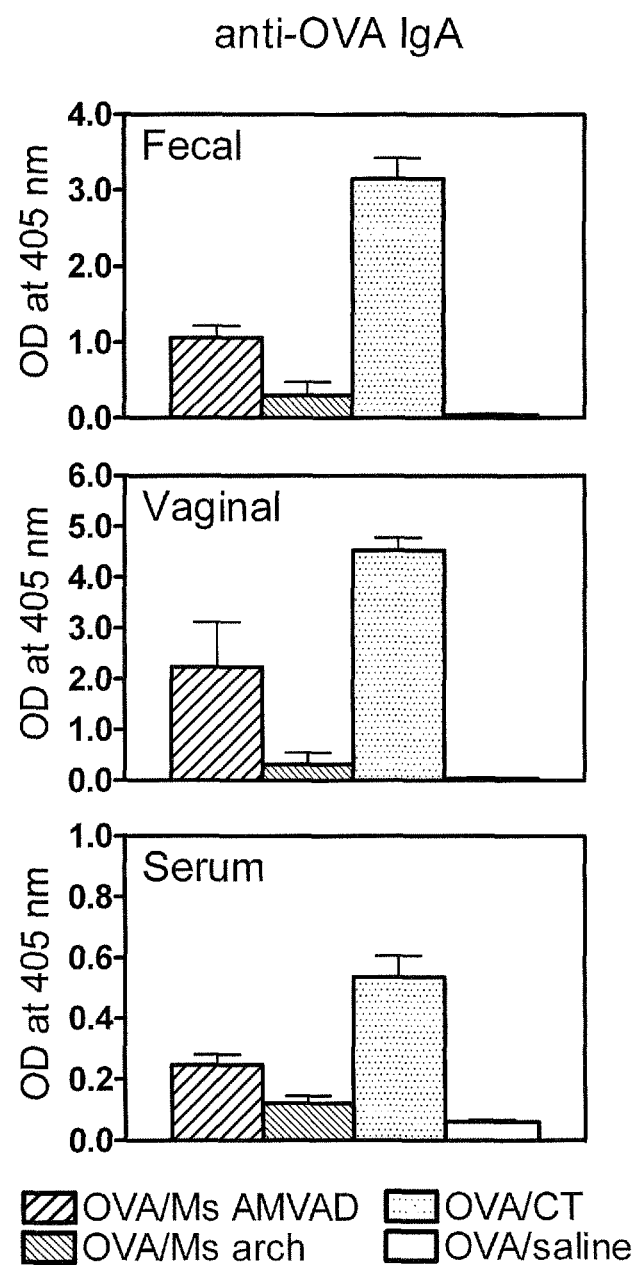
FIG. 4A shows the anti-OVA IgA antibody titres in the feces, vaginal wash, sera at 29 d in Balb/c mice that were vaccinated i.n. at 0, 7 and 21 d with 10 μg OVA formulated with Ms AMVAD, Ms archaeosomes (Ms arch), cholera toxin (CT) or saline (antigen alone, no adjuvant group).

The current invention shows that pharmaceuticals, biologically relevant molecules, and antigens can be formulated into compositions comprising aggregated spherical structures obtained by the interaction of unilamellar archaeosomes (i.e., closed vesicles made from archaeal polar lipid) and a positively charged ion such as a cation (the resultant structure referred to herein as archaeal lipid mucosal vaccine adjuvant and delivery (AMVAD) structure) in the presence of the pharmaceutical, biologically relevant molecule or the antigen, for delivery of the pharmaceutical, biologically relevant molecule or the antigen to the host, via a mucosal route of administration.

The current invention shows that mucosal administration of vaccine formulations comprising the AMVAD structure and an antigen, unexpectedly induces a strong and sustained antigen-specific mucosal immune response to the acellular protein, peptide or protein-polysaccharide conjugate antigen, without the need for inclusion of other known immune modulating adjuvants in the vaccine formulation. That is, the AMVAD structure is a self-adjuvanting carrier of antigens that helps elicit mucosal immunity upon administration of the vaccine via a mucosal route such as the intranasal route This is clearly contrary to prior uses of archaeosomes and conventional liposomes, which fail to elicit antigen-specific mucosal immunity upon mucosal administration. This is also contrary to prior cochleate formulations wherein the antigen is entrapped in the rolled up bilayer sheets made from conventional ester lipids, and wherein the cochleate structures have no encapsulated aqueous space or compartments.

The AMVAD structures of the present invention are aggregated, spherical structures (appearance like a bunch of grapes) which have larger average widths than the starting unilamellar archaeosomes, and the AMVAD structure does have aqueous compartment/capture volume. The mucosal administration of the vaccine comprising the AMVAD structure/antigen, in addition to the strong, protective mucosal immune response, can also elicit strong and sustained systemic MHC-I (CTL) and MHC-II (Th1 and Th2) responses, as well as strong memory responses. These observations were unexpected, and contrary to literature expectations of such delivery systems.

Mucosally administered vaccines can also alleviate issues with parenteral vaccinations, such as the use and disposal of needles, need for trained personnel for vaccine administration, and injection site reactions including puncture site infections. Mucosal vaccines can also be more acceptable to the vaccine. In addition, the regulatory burden is less onerous than for parenteral vaccines. Mucosal vaccines can also overcome barriers of pre-existing systemic immunity from previous vaccination or from maternal antibodies in young children, or the selective immuno-suppression such as in AIDS patients. Hence, vaccines that upon mucosal administration can elicit not only a protective mucosal immunity, but also additional systemic immunity consisting of humoral, and cell-mediated immunity including CD8⁺ cytotoxic T-lymphocyte (CTL) responses.

Intranasal (i.n.) and oral (per oral, p.o.) are some of the most desirable mucosal administration routes for pharmaceuticals, biologically relevant molecules, and antigens in vaccine compositions. However, other routes such as ocular, buccal cavity, and rectal, can also be used. There can also be differences in the adsorption of the antigen administered via the p.o. and the nasopharyngeal routes such as i.n., which helps to explain why the administration of a vaccine/adjuvant via these different routes will not necessarily elicit the same types of immune responses.

Examples of the efficacy and utility of AMVAD structure as self-adjuvanting carrier for appropriate acellular antigens to elicit mucosal and systemic immunity, as well as the protective immunity against infection by pathogens, is demonstrated herein using murine models.

Many of the mucosally invading pathogens are intracellular pathogens (including viruses), discussed in more detail below, that establish themselves inside the host cells.

The skilled artisan will recognize that the antigen is selected based on the type of disease affecting the patient. The pathogen from which the acellular antigen is derived, or is based upon, could be from a bacterium, a virus, or a protozoan parasite, as examples. Such antigen could be the killed whole pathogen, or a component extracted from the pathogen, such as a toxin or capsular polysaccharide produced by the pathogen, membrane protein, coat protein, cytoplasmic protein, protein fragments, peptide, carbohydrate or other component. The antigenic peptide sequence could be chemically synthesized, for example from amino acids and/or by polymerization, or produced by recombinant technology, both of which are well known in the prior art.

In another embodiment, the antigen is from a pathogen where mucosal immunity is important to protect the immunized host against infection or re-infection.

In another embodiment, the antigen is from a pathogen which primarily invades the host through the mucosal surface. Examples of such pathogens (given for illustrative purposes only and not to limit the scope of the invention) are *Escherichia coli, Campylobacter* sp., *Salmonella* sp., *Listeria monocytogenes, Helicobacter pylori, Shigella* sp., rotaviruses, caliciviruses in the gastrointestinal (GI) tract; *Mycoplasma pneumoniae*, influenza virus, severe acute respiratory syndrome (SARS) virus, *Mycobacterium tuberculosis, Streptococcus pneumoniae*, and respiratory syncytial virus in the respiratory tract; human immunodeficiency virus (HIV), *Neisseria*, and *Chlamydia* in the uro-genital tract; and malaria parasite.

In another embodiment, the antigen is from a pathogen where cellular immunity is important to protect the immunized host against infection or re-infection. It will be well recognized by the skilled artisan that intracellular pathogens are one group of infectious agents that require the vaccinated host to mount cellular immunity to protect the host from the infectious challenge. Examples of intracellular pathogens (given for illustrative purposes only and not to limit the scope of the invention) are bacteria that cause tuberculosis (*Mycobacterium tuberculosis*), listeriosis (*Listeria monocytogenes*), tularemia (*Francisella tularensis*), and leprosy (*Mycobacterium leprae*), viruses [members of the families adenovirus, coronavirus, herpes virus, orthomyxovirus, papovirus, paramyxovirus, picornavirus (the most readily acknowledged viruses being HIV which cause AIDS, virus causing SARS and the viruses that cause influenza)], and parasites that cause malaria (*Plasmodium* species), toxoplasmosis (*Toxoplasmosis gondii*), and leishmaniasis (*Leishmania* species).

In yet another embodiment, the antigen is a tumor associated antigen (i.e., antigen associated with neoplastic disease). Tumor antigens are well known in the art. Illustrative examples are prostrate specific antigen, carcinoembryonic antigen, mucins, and various melanoma antigens. Skilled artisans will appreciate that the type of immune reaction elicited will also depend on whether the antigen has the respective epitope(s) required for generating the MHC class I, and/or MHC class II pathway generated immune reactions. Such appropriate antigens can be prepared readily by those skilled in the art, using traditional or modern synthetic or recombinant techniques.

In yet another embodiment, the antigen is an allergen or autoantigen (i.e., antigens inducing allergic disorders and autoimmune diseases). Allergens and autoantigens are well known in the art. Illustrative examples are dust mites, pollen, animal dander, sDNA, anti-nuclear antibodies (ANA), nDNA, myelin basic protein (MBP), thyroglobulin and insulin. It will be well recognized by the skilled artisan that suppression of the immune response, particularly T cell reactivity, production of autoantibodies and IgE, and induction of immunoregulatory T cells by incorporating the appropriate allergens or autoantigens with a self-adjuvanting carrier such as the AMVAD, will delay or suppress the onset of allergic disorders and autoimmune diseases.

In the present invention, it is acceptable but not essential, that the antigen first be encapsulated within the archaeosome and/or be associated with the archaeosome vesicle layer before converting this to the AMVAD-antigen formulation by the addition of appropriate amount of cation. One skilled in the art will also recognize that association of the antigen with/in the archaeosome can be accomplished by encapsulating the antigen within the archaeosome and/or associating it with the archaeosome lipid layer using methods known in prior art for liposomes and archaeosomes. This may be accomplished, for example, by either covalent or non-covalent (e.g., hydrophobic, adsorption) interaction between the liposome and the antigen.

It will also be appreciated by the skilled artisan that the attachment of the peptide or protein antigen to the archaeosome can be quantitatively facilitated by linking a hydrophobic anchor, such as a fatty acyl group or a hydrophobic sequence of amino acids, to a terminal end of the peptide. However, for the current invention to work, such modification of the antigen is not a prerequisite. In the present invention, the AMVAD structure acts as a carrier for the antigen and simple admixing of the antigen with pre-formed empty (devoid of antigen) AMVAD structures fails to elicit strong antigen-specific immune responses.

The vaccine composition of the invention comprises the AMVAD structure as a self-adjuvanting carrier for the acellular antigen, and may include other pharmaceutically acceptable excipients (e.g., water, saline, glycerol, dextrose, pH buffering agents, bacteriostatic compounds and combinations thereof) that are compatible with the active components in the vaccine formulation, and not deleterious to the recipient thereof.

As will be appreciated by one skilled in the art, the compositions of the invention can be used to immunize a host in need of protection from infection by a specific infectious agent or at risk from developing a specific disease or tumor-associated ailment. The vaccine formulations of the invention will include an immune stimulating amount of appropriately selected acellular antigen. Immunization of the host can be accomplished by the normally acceptable routes of mucosal vaccine administration including intranasal, ocular, buccal, genital tract (vaginal), rectal, intratracheal, skin, and gastrointestinal tract as examples. Immunization of the host can also be by parenteral routes such as subcutaneous (s.c.), intramuscular (i.m.), and intradermal (i.d.), but this typically strong systemic immune responses with a much less significant mucosal immune response.

The dosage of the vaccine formulation is administered in a manner compatible with the host to be immunized, the route for immunization, and in a manner that will be therapeutically effective, immunogenic and protective. The skilled artisan will easily be able to factor in the various circumstances and determine the most appropriate regimen for immunization.

It is shown that as self-adjuvanting carriers that promote mucosal immunity, AMVAD structures are superior to many prior adjuvants. Strong and maximal immune responses are typically mounted early after vaccination, the responses last a prolonged period of time, responses are boostable (i.e. have a memory response), and the responses protect the vaccinated host against challenge by the corresponding antigen specific pathogen. The AMVAD vaccines of the current invention are safe, non-toxic, and cause no adverse reactions in the vaccinated host.

In the present invention, AMVAD structures are typically precipitates that comprise spherical structures that have aggregated into structures resembling bunches of grapes that still maintain aqueous compartments or spaces, and are prepared from the polar lipid extract from one or more members of *Archaea*, or from lipid(s) that mimic polar lipid structures found in members of *Archaea*, or from one or more polar lipid(s) purified in a biologically pure form from *Archaea*. Such AMVAD-like structures are also referred to herein as spherical, archaeal polar lipid aggregates.

The skilled artisan will appreciate that lipids that structurally mimic (such as those made by chemical synthesis) the polar lipids found in the *Archaea* may be used to make AMVAD structures for the purposes of the current invention. The *Archaea* produce many different polar lipid structures that are useful to produce AMVAD structures. Of the available species of *Archaea* as a class of organisms, several are discussed herein as illustrative examples as sources of lipids for preparing AMVAD structures for the current invention. A common feature of the archaeal polar lipids is their unique structures, the phytanyl chains and the ether bonds attaching the phytanyl chains to the glycerol carbons at sn 2,3 positions.

The AMVAD vaccines of the current invention can be made by various methods without affecting their efficacy in generation of mucosal and systemic immunity upon immunization of the host via a mucosal route. One such method comprises making archaeosomes with encapsulated antigen and converting this preparation, without removal of un-encapsulated antigen, into AMVAD vaccine by addition of sufficient amount (in proportion to the archaeal lipid) of a cation such as $Ca^{2+}$ in the form of $CaCl_2$. The free, soluble antigen in the formulation can be removed by centrifugation.

Cations for use according to the subject invention are multivalent cations, including divalent cations in some preferred embodiments. One skilled in the art will recognize that different multivalent cations, based on the number of positive charges they carry, can require different amounts of the cation to derive the same effect respective to forming the subject structures. Multivalent cations for use according to the subject invention can include Magnesium ($Mg^{2+}$), Zinc ($Zn^{2+}$), Barium ($Ba^{2+}$), Iron ($Fe^{2+}$), Calcium ($Ca^{2+}$), trivalent cations such as Aluminum ($Al^{3+}$), and the like. Multivalent organic cationic compounds such as tobramycin sulphate and 2,4,5,6-Tetraminopyrimidine sulphate can also be used to make the subject structures. With that noted, one preferred multivalent cation for archaeal lipid aggregate formation, for example, is the divalent $Ca^{2+}$ that is added as $CaCl_2$. Monovalents are not preferred, as a monovalent (NaCl) does not appear to convert the archaeosomes into the AMVAD structures.

In the current invention, one alternate method of making an AMVAD vaccine formulation comprises making archaeosomes with encapsulated antigen, removing the un-encapsulated antigen from the archaeosome preparation by a method such as ultracentrifugation, and then converting this archaeosome preparation into AMVAD vaccine by addition of sufficient amount (in proportion to the archaeal polar lipid) of a cation such as $Ca^{2+}$ in the form of $CaCl_2$. The free, soluble antigen in the AMVAD formulation may be removed, if necessary, by centrifugation.

In the current invention, another alternate method for making AMVAD vaccine comprises making archaeosomes with encapsulated antigen and converting this preparation, without removal of un-encapsulated antigen, into AMVAD vaccine by addition of sufficient amount (in proportion to the archaeal lipid) of a cation such as $Ca^{2+}$ in the form of $CaCl_2$. The free, soluble antigen in the formulation is not removed from the vaccine formulation.

In the current invention, yet another alternate method of making an AMVAD vaccine formulation comprises admixing the antigen with pre-formed empty archaeosomes and converting this preparation into AMVAD vaccine by addition of sufficient amount of a cation (in proportion to the archaeal lipid) such as $Ca^{2+}$ in the form of $CaCl_2$. The free, soluble antigen in the formulation may be removed, if necessary, by centrifugation.

The current invention also includes methods of use of the AMVAD vaccine compositions for the elicitation of strong and sustained mucosal and systemic immunity in the host upon mucosal immunization.

The invention also includes a method of use for the elicitation of strong and sustained systemic immunity in the host upon systemic immunization.

The above disclosure generally describes the current invention. This invention will be better understood from the illustrative Examples given. The data therein are for illustrative purposes only, and are not intended to limit the scope of the invention. Changes in form and substitution of equivalents are contemplated as the circumstances may suggest appropriate. Modification and variations of the methods and reagents described herein will be obvious to those skilled in the art, and are intended to come within the scope of the appended claims.

Definitions of some of the various terms used in this description

The specific terms (definitions) used in the disclosure are intended in a descriptive sense and are not intended for the purposes of limitations.

Antigen: an immunogen (e.g., derived from proteins, peptides, carbohydrates, nucleic acids lipids and mixtures thereof) to which an animal such as a human mounts an immune response. The antigen may be a conjugate of a carbohydrate (polysaccharide) and a protein. The term antigen is intended to include a molecule that contains one or more epitopes which stimulate a host's immune system to produce specific humoral, cellular (cell-mediated) and/or secretory immunological response. The antigen may possess specific epitopes known to be required for the elicitation of immune responses via the MHC class I or MHC class II antigen processing pathways of the immune system.

Acellular antigen: an antigen that is non-replicating (not able to grow and multiply), and this antigen may represent an extract from a pathogenic microorganism including viruses, bacteria/mycoplasma, fungi, protozoa, other parasites, or from a diseased tissue, or it could a purified or a highly purified component thereof, additionally including such components that are chemically synthesized or produced by recombinant methods so as to mimic those found in the pathogen or diseased tissue. The antigen may be completely and readily soluble (dissolved) in water or aqueous buffer, the antigen maybe hydrophobic (not readily soluble in water or aqueous buffers, for example alkylated peptide), it may consist of a mixture of antigens or a single purified antigen, and it may be an alkylated peptide. The antigen could be in a particulate form. The antigen or antigens may be comprised of all or a certain part of a pathogenic microorganism, or all or a specific part of a protein, glycoprotein, glycolipid, polysaccharide (carbohydrate) or lipopolysaccharide which is associated with the microorganism. Suitable antigens can be derived from, for example, *Salmonella, Helicobacter*, HIV, *Moraxella*, Mycobacteria, influenza virus, the pathogens are well known in the field of infectious diseases. The antigen could also be derived or extracted from sources other than a microorganism, for example cancer cells/tissue or allergens.

Cancer: malignant growth or tumor caused by abnormal or uncontrolled cell division; it may spread to other parts of the body (synonymous to malignant neoplastic disease).

Tumor-specific or tumor antigen: antigen expressed by tumor cells and not by normal cells. Methods for the extraction of antigen from source particle, cell tissue or organism are known in prior art.

Allergen: an antigen that triggers an allergic response such as the type 1 hypersensitive immune responses in some hosts; examples of such allergens include house dust mite, dog or cat dander, pollen from rye grass, ragweed and the like, milk protein and bee venom. The antigen could also be a component responsible for inducing autoimmune diseases (autoantigens) such a myelin, insulin peptide B and the like.

Autoantigen: also known as self-antigen; an antigen that although being a normal constituent of the host results in triggering of humoral or cell-mediated immune responses as in autoimmune diseases; an endogenous antigen that induces production of autoantibodies. An antigen could also be defined as a non-self antigen, a foreign substance that is capable of inducing an immune reaction in the host. The antigen could be a DNA molecule, or a nucleic acid molecule encoding a protein antigen that induces immunity. A hapten is within the scope of the definition of an antigen. The antigen could be used for vaccines for treatment of autoimmune diseases such as diabetes, hypo- and hyper thyroidism, psoriasis, arthritis or the treatment/prevention of cancer. The antigen could also be used for vaccines for the treatment and prevention of infectious diseases such herpes, HIV, and papilloma. The antigen could also be used for the treatment or prevention of diseases caused by pathogens that invade the host via mucosal surfaces. The antigens, besides being administered in vaccines formulated with an AMVAD structure of the present invention, are contemplated to be administered together with other known adjuvants.

Adjuvant: a substance or material with immune modulating (immunomodulating) and/or carrier activity, which when administered with an immunogen enhances the immune reaction to that immunogen. Self-adjuvanting carrier—a carrier or delivery vehicle for an antigen, that functions to help elicit a strong antigen-specific immune response in the absence of the requirement for other known adjuvants in the formulation. Adjuvant activity includes but is not limited to, the ability to enhance quantitatively or qualitatively, the immunological response to the antigen by increasing the immunogenicity (level of the immune response) to the antigen or by reducing the dose or level of the antigen required to produce an immune response, or to reduce the number or the frequency of immunizations required to produce the desired immune response.

Acellular vaccine: a vaccine composition that is free from any self-replicating components such as for example, viable cells.

Host, any animal, including a mammal, such as a human, cow, pig, horse, cat, dog, sheep. The host could also be a bird such as chicken (poultry), turkey, duck, or a fish such as salmon.

A biologically relevant molecule, one that has a role in life processes of a living organism. The molecule could be organic, or inorganic, a monomer or a polymer, endogenous to a host organism or not, naturally occurring or synthesized in vitro and the like. The examples include vitamins, minerals, co-factors, enzymes, polypeptides, proteins, lipids, carbohydrates, toxins, amino acids, cytokines, and the like.

Pharmaceutical: pharmaceutical compound or agent, a substance or a compound or a component that is used for the treatment of disease (variously also referred to as drug, medicament, medicine, medication).

Immune response: a specific response of the immune system of an animal to an antigen or an immunogen. Immune response may include the production of antibody, cellular, proliferative or cytotoxic (cytolytic) activities, or the secretion of cytokines. The immune response may be classified as mucosal response, based on the production of antigen-specific IgA responses, especially at the mucosal surfaces, or it could be classified as systemic response, based on the production of antigen-specific serum IgG, IgG1 and IgG2a responses.

Cell-mediated immune response: an immune response that is characterized by the involvement of effector T lymphocytes (such as cytotoxic T cells, CD4$^+$ T-helper cells, and regulatory T-cells); these immune responses being implicated in allograft rejection, delayed type hypersensitivity, and in the killing of cancer cells and cells infected by intracellular pathogens; an immune response other than the production of humoral antibodies.

Immunity: a state of resistance of a subject animal to an infecting organism or a disease.

Immunizing dose: the amount of antigen or immunogen needed to induce an immune response. This amount will vary with the presence and effectiveness of various adjuvants. The amount will vary with the animal and immunogen or the antigen.

Memory response: immune cells that have previously been exposed to an antigen, are in resting stage but capable of being activated upon exposure to the antigen again. Conventional phospholipid or ester phospholipids or ester lipid: a glycerolipid in which the hydrocarbon chains are linked via ester bonds at the sn-1,2 carbon positions of the glycerol backbone.

Archaeal or archaeobacterial polar lipid: polar lipid derived from a member of the class *Archaea* (synonymous to *Archaeobacteria*) or a lipid that is chemically synthesized to mimic the unique structure of archaeal polar lipid(s) wherein the phytanyl chains are attached via ether bonds to the glycerol backbone at sn-2,3 carbon positions.

Liposome: closed vesicle entrapping or encapsulating an aqueous volume, made of lipid membranes; the liposome may be unilamellar, oligolamellar or multilamellar.

Conventional liposome: a liposome prepared from ester lipid and in some cases including a sterol, and may include other compounds that are entrapped within the vesicle or associated with the lipid membrane.

Archaeosome: a liposome prepared from one or more of the polar lipids that are unique to the species in the class *Archaea*, including those vesicles made from archaeal polar lipid(s) or lipid(s) that structurally mimic the polar lipids found uniquely in archaeal species (archaeobacteria). Similar to conventional liposomes, archaeosomes may include other compounds that are entrapped within the vesicle or associated with the lipid membrane layer.

Multivalent cations: multivalent cations include inorganic and organic multivalent cations, include the following divalent cations: $Ca^{2+}$, $Mg^{2+}$, $Zn^{2+}$, $Ba^{2+}$, $Fe^{2+}$. Divalent cations are some preferred cations, as is $Ca^{2+}$. However, trivalent cations such as $Al^{3+}$ can also be used according to the subject invention. Also included are organic cationic compounds such as 2,4,5,6-Tetraminopyrimidine sulphate and tobramycin sulphate, which are multivalent cationic compounds that can be used in place of inorganic cations to make the subject AMVAD structures and, in one step, associate these drugs with AMVAD. See Example 30.

AMVAD structure: archaeal lipid mucosal adjuvant and mucosal vaccine delivery structure; a single AMVAD structure comprises an aggregate of spherical structures resembling a bunch of grapes and containing aqueous compartment(s) or aqueous capture volume, formed by the addition of cations such as $Ca^{2+}$ to a preparation of small, unilamellar, archaeosomes; also referred to as archaeal polar lipid aggregates; individual AMVAD structures or aggregates may further clump together to result in multi-AMVAD or multi-aggregate structures (like several bunches of grapes stuck together); the term AMVAD structure includes single and multi-AMVAD structures. The AMVAD structure may be formulated in association with a pharmaceutical, a biologically relevant molecule or an antigen.

AMVAD vaccine: AMVAD structure formulated with an antigen and used for administering, immunizing or vaccinating a host. The name of the archaeal species (archaeobacterium) associated with the word archaeosome (for example, *M. smithii* archaeosome, or archaeosome of/from *M. smithii*) indicates that the archaeosome is made from lipids extracted from that specific archaeal species, and unless stated to the contrary, from the total polar lipids (TPL) extract of that archaeal species. The name of the archaeal species associated with the word AMVAD indicates that the AMVAD structure comprises the polar lipid extract from that archaeal species, and unless stated to the contrary, from the total polar lipids extract of that archaeal species. For example, Ms AMVAD would indicate that the AMVAD structure was prepared from the TPL extracted from *M. smithii*. When an antigen such as ovalbumin (OVA) is part of the AMVAD vaccine formulation, for example made from TPL extracted from *M. smithii*, this would be referred to as OVA/Ms AMVAD.

The compositions of the invention, and in particular for intranasal administration, may be formulated as liquids or dry powders. Compositions for administration as nasal drops may contain one or more compatible ingredients of the type customarily included in such compositions, for example preservatives, viscosity adjusting agents, tonicity adjusting agents, buffering agents and the like.

The present invention also contemplates the provision of means for the intranasal delivery of the compositions. A dispensing device, may for example, take the form of an aerosol delivery system that may be adjustable to dispense a single dose or a multiplicity of doses, or could be in the form of nasal foam or nasal ointment, or simply a suspension introduced into the nares (nose opening) using a pipeting or similar liquid dispensing devise.

Some preferred embodiments of the subject invention include:
1. A composition for administration to an animal, said composition comprising multivalent cations in association with a plurality of spherical archaeal polar lipid aggregates containing aqueous compartments, the AMVAD structure, and at least one active component selected from the group consisting of a pharmaceutical, a biologically relevant molecule, and an antigen, wherein the archaeal polar lipid is a polar lipid extract from an archaeal species.
2. The composition according to Embodiment 1, wherein the multivalent cations are divalent cations.
3. The composition according to Embodiment 2, wherein the divalent cations are $Ca^{2+}$.
4. A composition according to Embodiment 3, wherein the $Ca^{2+}$ is provided as $CaCl_2$.
5. A composition according to Embodiment 6, wherein in the total polar lipid extract from the archaeal species is mixed with the neutral lipids from the archaeal species.
6. A composition according to Embodiment 1, wherein the polar lipid extract is the total polar lipids extract from an archaeal species.
7. A composition according to Embodiments 1, 2, 3, 4, and 6, wherein the archaeal species is selected from the group consisting of *Methanobrevibacter smithii*, *Halobacterium salinarum* and *Thermoplasma acidophilum*.
8. A composition according to Embodiment 6, wherein the archaeal species is *Methanobrevibacter smithii*.
9. A composition according to Embodiment 6, wherein the archaeal species is *Halobacterium salinarum*.
10. A composition according to Embodiment 6, wherein the archaeal species is *Thermoplasma acidophilum*.
11. A composition according to Embodiment 1, wherein the polar lipid extract contains only one archaeal polar lipid.
12. A composition according to Embodiment 11, wherein the only one archaeal polar lipid in the extract is archaetidyl glycerophosphate-O-methyl.
13. A composition according to Embodiment 12, wherein the archaetidyl glycerophosphate-O-methyl is extracted from Halobacterium salinarum.
14. A composition according to Embodiment 1, comprising the following steps of preparation:
   a) preparation of unilamellar archaeosomes from a polar lipid extract from an archaeal species, with encapsulated pharmaceutical agent, biologically relevant molecule, or an antigen component;
   b) addition of $CaCl_2$ to the archaeosome suspension, without prior removal of the un-encapsulated component, in sufficient quantity in excess to the proportion of the lipid, to form typical AMVAD structures characterized by aggregates of larger spherical structures possessing aqueous capture volume;
   c) removal of the free, soluble pharmaceutical agent, biologically relevant molecule, or antigen component from the preparation, and re-suspension of the AMVAD formulation in physiological saline (0.85% NaCl, at pH 7.1) supplemented with sufficient $CaCl_2$ to maintain the integrity of the typical AMVAD structure.
15. A composition according to Embodiment 14, wherein the unilamellar archaeosomes prepared in step a) are prepared empty and the pharmaceutical agent, biologically relevant molecule, or an antigen component is then admixed with the archaeosome preparation prior to continuing with step b).
16. A composition prepared according to Embodiment 14, wherein in step a) the un-encapsulated pharmaceutical agent, biologically relevant molecule, or an antigen component is removed prior to continuing with step b).
17. A composition prepared according to Embodiment 14, wherein in step c) the free, soluble pharmaceutical agent, biologically relevant molecule, or antigen component is not removed.
18. A composition prepared according to Embodiment 14, wherein the lipid extract from an archaeal species in step a) is the total polar lipid extract.
19. A composition according to Embodiment 1, wherein the component selected is an antigen.
20. A composition according to Embodiment 19, wherein the AMVAD structure acts as a self-adjuvanting delivery vehicle for the antigen.
21. A composition according to Embodiment 19, wherein the multivalent cation is selected from the group consisting of divalent cations.
22. A composition according to Embodiment 21, wherein the divalent cation is $Ca^{2+}$.
23. A composition according to Embodiment 22, wherein the $Ca^{2+}$ is provided as $CaCl_2$.
24. A composition according to Embodiment 19, wherein the archaeal polar lipid extract is selected from the group consisting of the total polar lipid extract and only one polar lipid in the extract from the archaeal species.
25. A composition according to Embodiment 24, wherein the archaeal polar lipid extract is the total polar lipid extract of an archaeal species.
26. A composition according to Embodiments 19-25, wherein the archaeal species is selected from the group consisting of *Methanobrevibacter smithii*, *Halobacterium salinarum* and *Thermoplasma acidophilum*.
27. A composition according to Embodiment 26, wherein the archaeal species is *Methanobrevibacter smithii*.
28. A composition according to Embodiment 26, wherein the archaeal species is *Halobacterium salinarum*.
29. A composition according to Embodiment 26, wherein the archaeal species is *Thermoplasma acidophilum*.
30. A composition according to Embodiment 24, wherein the polar lipid extract contains only one archaeal polar lipid.
31. A composition according to Embodiment 30, wherein the only one archaeal polar lipid in the extract is archaetidyl glycerophosphate-O-methyl.
32. A composition according to Embodiment 31, wherein the archaetidyl glycerophosphate-O-methyl is extracted from *Halobacterium salinarum*.
33. A composition according to Embodiment 25, wherein in the total polar lipid extract from the archaeal species is mixed with the neutral lipids of the archaeal species.
34. A composition according to Embodiment 19, comprising the following steps of preparation:
   a) preparation of unilamellar archaeosomes from a polar lipid extract from an archaeal species, with an encapsulated antigen component;
   b) addition of $CaCl_2$ to the archaeosome suspension, without prior removal of the un-encapsulated antigen, in sufficient quantity in excess to the proportion of the lipid, to form typical AMVAD structures characterized by aggregates of larger spherical structures possessing aqueous capture volume;
   c) removal of the free, soluble antigen component from the preparation, and re-suspension of the AMVAD formulation in physiological saline (0.85% NaCl, at pH 7.1) supplemented with sufficient $CaCl_2$ to maintain the integrity of the typical AMVAD structure.
35. A composition prepared according to Embodiment 34, wherein the unilamellar archaeosomes prepared in step a) are prepared empty (without the encapsulated component) and the antigen component is then admixed with the archaeosome preparation prior to continuing with step b).
35a. A composition prepared according to Embodiment 35, wherein the free, soluble antigen component is not removed from the AMVAD formulation in step c).

36. A composition prepared according to Embodiment 34, wherein in step a) the un-encapsulated antigen component is removed prior to continuing with step b).
37. A composition prepared according to Embodiment 34, wherein in step c) the free, soluble antigen component is not removed.
38. A composition according to Embodiment 19, wherein the antigen is selected from the group consisting of a mixture of antigens, only a single purified antigen, a water soluble antigen, a hydrophobic antigen, a protein, a peptide, a carbohydrate-protein conjugate, a component extracted from a pathogen, and an antigen obtained by a recombinant method.
39. A composition according to Embodiment 38, wherein the antigen selected is a component extracted from a pathogen.
40. A composition according to Embodiment 39, wherein the pathogen is selected from the group consisting of *Listeria monocytogenes*, *Francisella tularensis*, and *Helicobacter pylori*.
41. A composition according to Embodiments 39 and 40, wherein the component extracted from the pathogen is the cell free extract from the pathogen.
42. A composition according to Embodiment 38, wherein the antigen selected is a mixture of antigens.
43. A composition according to Embodiment 42, wherein the mixture of antigens is the cell free extract selected from the group consisting of *Listeria monocytogenes*, *Francisella tularensis*, and *Helicobacter pylori*.
44. A composition according to Embodiment 38, wherein the antigen is a protein.
45. A composition according to Embodiment 44, wherein the protein antigen is selected from the group consisting of pneumococcal surface antigen A (PsaA), and cell free extract from a pathogen.
46. A composition according to Embodiment 38, wherein antigen is a peptide.
47. A composition according to Embodiment 46, wherein the peptide is an alkylated peptide amino acid sequence.
48. A composition according to Embodiment 38, wherein the antigen is a single purified antigen.
49. A composition according to Embodiment 48, wherein the single purified antigen is pneumococcal surface antigen A (PsaA).
50. A composition according to Embodiment 38, wherein the antigen is water soluble.
51. A composition according to Embodiment 50, wherein the water soluble antigen is pneumococcal surface antigen A (PsaA).
52. A composition according to Embodiment 38, wherein the antigen is obtained by a recombinant method.
53. A composition according to Embodiment 52, wherein the antigen obtained by a recombinant method is pneumococcal surface antigen A (PsaA).
54. A composition according to Embodiment 38, wherein the antigen is carbohydrate-protein conjugate.
55. A composition according to Embodiment 54, wherein the carbohydrate-protein conjugate is O-chain-BSA conjugate.
56. A method for the delivery of a pharmaceutical agent or a biologically relevant molecule in the composition according to Embodiment 1, to a host via administration to the host by a route to be selected from the group consisting of systemic or mucosal route, wherein the AMVAD structure acts as a carrier for the said pharmaceutical agent or the biologically relevant molecule.
57. A method for the delivery of an antigen in the composition according to Embodiment 1, to a host via administration to the host by a route to be selected from the group consisting of systemic or mucosal route, wherein the AMVAD structure acts as a self-adjuvanting delivery vehicle for the said antigen.
58. A method according to Embodiment 57, wherein the administration to the host is via the systemic route.
59. A method for the delivery of an antigen according to Embodiment 58, wherein the administration via the systemic route is via the subcutaneous route.
60. A method for the delivery of an antigen according to Embodiment 57, wherein the administration to the host is via the mucosal route selected from the group consisting of per oral and intranasal route.
61. A method for the delivery of an antigen according to Embodiment 60, wherein the administration to the host is via the intranasal route.
62. A method for the delivery of an antigen according to Embodiment 57, wherein an antigen-specific immune response is elicited in the administered host.
63. A method for the delivery of an antigen according to Embodiments 58, 59 and 62, wherein an antigen-specific systemic immune response is elicited in the administered host.
64. A method for the delivery of an antigen according to Embodiment 63, wherein the elicited antigen-specific systemic immune response is characterized by the elicitation of antigen-specific serum IgG, IgG1 and IgG2a antibody and an antigen-specific cytotoxic T lymphocyte immune responses.
65. A method for the delivery of an antigen according to Embodiment 63, wherein the elicited antigen-specific systemic immune response is characterized by the elicitation of antigen-specific cytotoxic T lymphocyte immune response.
66. A method for the delivery of an antigen according to Embodiments 63 and 64, wherein the elicited antigen-specific systemic immune response is sustained over a significant portion of the life span of the administered host.
67. A method for the delivery of an antigen according to Embodiments 63 and 64, wherein the elicited systemic immune response is subject to a strong memory boost response.
68. A method for the delivery of an antigen according to Embodiment 61, wherein the antigen-specific immune response elicited is a systemic immune response.
69. A method for the delivery of an antigen according to Embodiment 68, wherein the elicited antigen-specific systemic immune response is characterized by the elicitation of antigen-specific serum IgG, IgG1 and IgG2a antibody responses.
70. A method for the delivery of an antigen according to Embodiment 68, wherein the elicited antigen-specific systemic immune response is characterized by the elicitation of antigen-specific cytotoxic T lymphocyte immune response.
71. A method for the delivery of an antigen according to Embodiments 68 and 69, wherein the elicited systemic response is sustained over a significant portion of the life span of the administered host.
72. A method for the delivery of an antigen according to Embodiments 68, 69 and 70, wherein the elicited systemic immune response is subject to a strong memory boost responses.
73. A method for the delivery of an antigen according to Embodiments 60 and 61, wherein the elicited antigen-specific immune response is an antigen-specific mucosal immune response.

74. A method for the delivery of an antigen according to Embodiment 61, wherein the elicited antigen-specific immune response is an antigen-specific mucosal immune response.
75. A method for the delivery of an antigen according to Embodiment 74, wherein the elicited antigen-specific mucosal immune response is characterized by the elicitation of antigen-specific antibody responses consisting of one or more of serum IgA, vaginal IgA, bile IgA, fecal IgA and nasal IgA.
76. A method for the delivery of an antigen according to Embodiments 74 and 75, wherein the elicited mucosal immune response is sustained over a significant portion of the life span of the administered host.
77. A method for the delivery of an antigen according to Embodiments 74 and 75, wherein the elicited mucosal immune response is subject to a strong memory boost response.
78. A method for the delivery of an antigen according to Embodiment 74, wherein an antigen-specific systemic immune response is elicited in addition to the elicited antigen-specific mucosal immune response.
79. A method for the delivery of an antigen according to Embodiment 78, wherein the additional antigen-specific systemic immune response elicited is characterized by the elicitation of antigen-specific serum IgG, IgG1 and IgG2a antibody responses.
80. A method for the delivery of an antigen according to Embodiment 78, wherein the additional antigen-specific systemic immune response elicited is characterized by the elicitation of antigen-specific cytotoxic T lymphocyte immune response.
81. A method for the delivery of an antigen according to Embodiments 78, 79 and 80, wherein the antigen-specific systemic and antigen-specific mucosal immune responses are characterized by the elicitation of antigen-specific serum IgG, serum IgG1, serum IgG2a antibody and cytotoxic T lymphocyte responses, and of serum IgA, vaginal IgA, bile IgA, fecal IgA and nasal IgA responses, respectively.
82. A method for the delivery of an antigen according to Embodiments 78 and 79, wherein the systemic and mucosal immune responses are sustained over a significant portion of the life span of the administered host.
83. A method for the delivery of an antigen according to Embodiments 78, 99, 80 and 81, wherein the systemic and mucosal immune responses are subject to strong memory boost responses.
84. A method for the delivery of an antigen according to Embodiment 61, wherein the lipid extract is the total polar lipids extract of an archaeal species.
85. A method for the delivery of an antigen according to Embodiment 84, wherein the total polar lipids extract of an archaeal species is selected from the group consisting of *Methanobrevibacter smithii*, *Halobacterium salinarum* and *Thermoplasma acidophilum*.
86. A method for the delivery of an antigen according to Embodiment 85, wherein the archaeal species is *Methanobrevibacter smithii*.
87. A method for the delivery of an antigen according to Embodiment 85, wherein the archaeal species is *Halobacterium salinarum*.
88. A method for the delivery of an antigen according to Embodiment 85, wherein the archaeal species is *Thermoplasma acidophilum*.
89. A method for the delivery of an antigen according to Embodiment 61, wherein the antigen is selected from the group consisting of a mixture of antigens, only a single purified antigen, a water soluble antigen, a hydrophobic antigen, a protein, a peptide, a carbohydrate-protein conjugate, a component extracted from a pathogen, and an antigen obtained by a recombinant method.
90. A composition according to Embodiment 89, wherein the antigen selected is a component extracted from a pathogen.
91. A composition according to Embodiment 89, wherein the pathogen is selected from the group consisting of *Listeria monocytogenes*, *Francisella tularensis*, and *Helicobacter pylori*.
92. A composition according to Embodiments 89 and 90, wherein the component extracted from the pathogen is the cell free extract from the pathogen.
93. A composition according to Embodiment 89, wherein the antigen selected is a mixture of antigens.
94. A composition according to Embodiment 93, wherein the mixture of antigens is the cell free extract selected from the group consisting of *Listeria monocytogenes*, *Francisella tularensis*, and *Helicobacter pylori*.
95. A composition according to Embodiment 89, wherein the antigen is a protein.
96. A composition according to Embodiment 95, wherein the protein antigen is selected from the group consisting of pneumococcal surface antigen A (PsaA), and cell free extract from a pathogen.
97. A composition according to Embodiment 89, wherein antigen is a peptide.
98. A composition according to Embodiment 97, wherein the peptide is an alkylated peptide amino acid sequence corresponding to an amino acid sequence expressed by the pathogen.
99. A composition according to Embodiment 89, wherein the antigen is a single purified antigen.
100. A composition according to Embodiment 99, wherein the single purified antigen is pneumococcal surface antigen A (PsaA).
101. A composition according to Embodiment 38, wherein the antigen is water soluble.
102. A composition according to Embodiment 101, wherein the water soluble antigen is pneumococcal surface antigen A (PsaA).
103. A composition according to Embodiment 89, wherein the antigen is obtained by a recombinant method.
104. A composition according to Embodiment 103, wherein the antigen obtained by a recombinant method is pneumococcal surface antigen A (PsaA).
105. A composition according to Embodiment 89, wherein the antigen is carbohydrate-protein conjugate.
106. A composition according to Embodiment 105, wherein the carbohydrate-protein conjugate antigen is O-chain-BSA conjugate.
107. A method for administrating to an animal a vaccine composition comprising a composition according to any one of Embodiments 19, 20, 25, 27, 34, 35, 35a and 39-42, wherein the administered animal is afforded antigen-specific protective immunity against infection by a pathogen.
108. A method for administrating to an animal a vaccine composition according to Embodiment 107, wherein the composition is administered to the host via the intranasal route.
109. A method for administrating to an animal a vaccine composition according to Embodiments 107 and 108, wherein the antigen-specific protective immunity afforded against infection by a pathogen is against *Helicobacter pylori*.

110. A method for the delivery of an antigen to a host according to Embodiments 61, 68, 74, 78, 84, and 89, wherein the administered dosage of the composition comprises 0.032-0.626 mg polar lipid comprising the AMVAD structure and 1-150 µg antigen.

111. A method for the delivery of an antigen to a host according to Embodiment 110, wherein the administered dosage of the composition comprises 0.032 mg polar lipid comprising the AMVAD structure and 1 µg antigen.

112. A method according to Embodiment 1, wherein the individual AMVAD structure has an average width in the range of 1-30 µm.

113. A method according to Embodiment 112, wherein the individual AMVAD structure has an average preferable width in the range of 1-10 µm.

114. A method according to Embodiment 113, wherein the individual AMVAD structure has an average more preferable width in the range of 1-5 µm.

115. A composition according to Embodiment 5, wherein the archaeal species is *Methanobrevibacter smithii*.

116. A composition according to Embodiment 1, for eliciting an antigen-specific MHC class I-restricted cytotoxic T lymphocyte response and an antigen-specific MHC class II-restricted response in an animal, comprising administering to the animal a vaccine composition comprising an AMVAD structure made from the total polar lipids extract of an archaeal species and an antigen, wherein the AMVAD structure acts as self-adjuvanting carrier for the antigen.

117. A method for administrating to an animal a vaccine composition according to Embodiments 107 and 108, wherein the antigen-specific protective immunity afforded against infection by a pathogen is against *Francisella tularensis*.

Unless specifically indicated or implied, the terms "a", "an", and "the" signify "at least one" as used herein.

All patents, patent applications, provisional applications, and publications referred to or cited herein are incorporated by reference in their entirety to the extent they are not inconsistent with the explicit teachings of this specification.

EXAMPLES

The invention is further described by means of the following examples, which are not meant to limit scope of the invention.

Example 1

Archaeal Polar Lipids

As representative species of *Archaea*, *Methanobrevibacter smithii* ALI (DSM 2375) which is a methanogen (obligate anaerobe), *Halobacterium salinarum* ("*H. cutirubrum*") (ATCC 33170=DSM 669) which is an extreme halophile which requires 4M NaCl for optimal growth, and *Thermoplasma acidophilum* 122-1B3 (ATCC 27658=accession number 15156 of the Institute of Fermentation, Osaka, Japan) which is a thermoacidophile which grows optimally at pH 1-2 at 55° C., were obtained from the Deutsche Sammlung von Microorganismen (DSM) or the American Type Culture Collection (ATCC) as indicated. *M. smithii* was cultivated in a 75 L fermenter vessel, and the other two in a 250 L vessel, as described previously (Choquet et al., 1994). For the growth of *T. acidophilum*, the medium was supplemented with 4 g/L additional yeast extract during growth. The harvested cells were frozen (−70° C.) and thawed (room temperature) three times, and the total lipid extract (TLE) of each species was obtained by solvent extraction method as described earlier (Sprott et al., 2003). The total polar lipid (TPL) extract of each species was obtained by acetone precipitation from the respective TLE (Sprott et al., 2003). Archaetidyl glycerol-phosphate-O-methyl (PGP; PGP-0-CH$_3$) polar lipid was isolated from the TPL of *H. salinarum* as described (Kates et al., 1993). The polar lipid extracts were analyzed by FAB MS and thin layer chromatography for quality control, and were stored at 4 C in chloroform, to minimize solvent evaporation.

Example 2

Preparation and Characterization of Archaeosome Formulations

All preparations were made aseptically using pyrogen-free, sterile, deionized distilled water. The glassware used was made pyrogen-free by heating (180° C. for 6 h). All archaeosomes were prepared from the total polar lipids extract (TPL), the total lipid extract (TLE) obtained from the indicated archaeal species, or from the purified polar lipid archaetidyl glycerolphosphate-0-methyl (PGP) obtained as described in Example 1, by hydration of dried lipid film except for Ta archaeosomes. Unless indicated otherwise, 20 mg of the lipid in chloroform was dried in a 50 ml round bottom flask under vacuum (35° C., 520 mbar vacuum, 60 min), and the dried lipid film (devoid of any traces of the solvent) was hydrated for 1-2 h period in 1 ml of deionized distilled water at 35° C. using a rotary evaporator (no vacuum), followed by brief period of vortexing to obtain mostly multilamellar archaeosomes. If need be, the hydration of the lipid film can be accomplished at lower (e.g. room) or higher temperature without affecting the formation of archaeosomes. The multilamellar archaeosomes were converted to unilamellar archaeosomes of an average diameter of ca 100 nm, by a brief period of sonication (usually less than 5 minutes) in a bath sonicator. The archaeosomes were annealed by overnight (ca 18 h) storage at refrigeration temperature (4-7° C.). All the above steps for making archaeosomes, and subsequent ones including for storage, were undertaken without any precautions to exclude air or oxygen. The amount of lipid and the hydration volume can be altered as appropriate, to obtain various different weight concentrations of the archaeosomes per unit liquid volume.

For encapsulation or entrapment of ovalbumin (OVA) or bovine serum albumin (BSA), or other water soluble antigens into archaeosomes, the dried lipid film as described above (20 mg lipid) was hydrated in 1 ml of filter sterilized stock solution of OVA or BSA in water (10 mg/ml) or in appropriate solution of another antigen, instead of plain water, essentially as described earlier (Sprott et al., 2003). Fatty acid free-bovine serum albumin (BSA) and ovalbumin (OVA) were purchased from Sigma Chemical Company (Sigma Chemical Co., St. Louis, USA). The starting ratio of lipid:antigen (w/w) was kept at 2:1 unless indicated otherwise.

The pH of the antigen solution was adjusted to above the isoelectric point (pI) of the antigen (if the pI was known) prior to its addition for hydration of the lipid, so that the antigen was predominantly negatively charged. This precaution avoids charge-related aggregation of lipids and the antigen, since the archaeal total polar lipids have a net negative charge. In case the pI of the antigen is not known, and aggregation is observed upon adding the stock antigen solution to the dried lipid film, adjust the pH (more alkaline or acidic as required), until the aggregation is not visible.

The encapsulation procedure was then started with fresh materials, but having pre-adjusted the pH of the stock antigen solution to the value that resulted in clearance of the aggregates. The rest of the procedure was similar as above for making empty archaeosomes, to obtain unilamellar vesicles of ca 100 nm average diameters. The archaeosomes were annealed by overnight (ca 18 h) storage at refrigeration temperature (4-7° C.). Un-encapsulated antigen was removed by ultracentrifugation (275,000×g for 2 h) and washing the archaeosome pellet once in deionized distilled water at the appropriate pH used for hydration of the lipid film. The washed archaeosomes were resuspended into 1 ml of deionized distilled water. Prior to immunization, the archaeosome formulations were diluted using concentrated saline, to obtain the immunization dose in final concentration of 0.85% NaCl.

Empty *T. acidophilum* archaeosomes were prepared from the Ta TPL which was obtained as described in Example 1, by the reverse-phase evaporation (REV) method (Szoka and Papahadjopoulos, 1978), and the archaeosomes were re-suspended in a small volume of water. For making OVA/Ta archaeosomes, the empty archaeosomes suspension above was supplemented with OVA in water, at similar starting TPL:OVA ratio (2:1, w/w) as described above for hydrating Ms TPL in OVA/water to make OVA/Ms archaeosomes. The suspension was bath sonicated to encapsulate the OVA into small unilamellar vesicles. The rest of the procedure for processing of the OVA/Ta or Ta archaeosomes was similar to that described above for the other archaeosomes.

Archaeosome formulations were characterized for dry weight, vesicle size distribution, and antigen loading (encapsulated within the archaeosomes and associated with the vesicle surface). The preparations were also observed under phase contrast microscopy for verifying the absence of bacterial contaminants. The salt-free dry weight of lipids constituting the archaeosomes in archaeosome formulations was determined by drying (50° C.) an aliquot of the formulation to constant weight and subtracting the amount of antigen (determined as described below) and/or the dry weight of buffer salts as applicable.

The mean archaeosome vesicle diameter was determined by number weighted Gaussian size distribution using a Model 350 Nicomp® (5 mW He/Ne laser, Santa Barbara, USA) particle sizer. Unless indicated otherwise, the mean diameters of the archaeosome formulations used in immunization studies were in the range of 60-200 nm.

For determining the amount of OVA or BSA or other protein antigen encapsulated in archaeosomes, an aliquot of the archaeosome formulation was de-lipidated using a minor modification of the method of Wessel and Flugge (Wessel and Flugge, 1984), and the extracted protein was quantitated by the SDS-Lowry assay using the appropriate protein standard curves, as described (Sprott et al., 2003). The amount of antigen encapsulated in archaeosomes was also semi-quantitatively verified by performing SDS-PAGE (12.5% polycrylamide gels or as appropriate for antigens of different MW) analyses (an aliquot of the sample was mixed with Laemelli buffer and heated at 100° C. for 5 min before loading on the gel), by comparing the antigen band density against that of known amount of the antigen standard. Unless stated otherwise, the protein antigen determinations reported here are based on the Lowry assays. The antigen loading is reported as µg antigen/mg lipid. The average loading of OVA or BSA in various archaeosome formulations prepared as described above, was in the range of 24-44 µg/mg lipid.

All archaeosome formulations were stored at refrigeration temperature (4-7° C.), until required for use. The formulations were stable (no aggregation, <10% leakage of encapsulated antigen) for close to 2 years of storage. When required for immunization, the archaeosome formulations were diluted in a final concentration of 0.85% NaCl (pH 7.1) for obtaining the final immunization dose.

Unless indicated otherwise, unilamellar archaeosomes formulations used herein were prepared as described above, from the TPL extracted from the indicated species, with the specified antigen being encapsulated therein. The nomenclature used was as follows. OVA/Ms archaeosomes indicates that unilamellar archaeosomes were prepared from the TPL extracted from *M. smithii*, and OVA was the antigen encapsulated in the archaeosomes. Archaeosomes from *M. smithii* TPL, without any encapsulated antigen are referred to as empty Ms archaeosomes.

One skilled in the art will recognize that the starting ratio of lipid:antigen can be altered as appropriate, in order to increase or decrease the antigen loading in the vesicles (i.e., the amount of antigen loaded per unit weight of the lipid comprising the vesicles). Archaeosomes can also be prepared by any of the methods described in the prior art, and by methods described/applicable for making liposomes from ester lipids.

Example 3

Standard Protocols for Preparing and Characterizing OVA/AMVAD, BSA/AMVAD or Other Soluble Antigen(s)/AMVAD Formulations AMVAD formulations were prepared by the interaction of cations (for example, $CaCl_2$ solution) with suspensions of archaeosomes in water, saline or PBS. Empty AMVAD formulations (no associated antigen) were prepared from empty archaeosomes (containing only encapsulated water), and antigen/AMVAD formulations were prepared from archaeosomes containing encapsulated antigen(s). A preferred method (standard protocol) for preparing AMVAD formulations was as follows: empty or antigen-loaded (OVA, BSA or other soluble antigen) unilamellar archaeosomes from TPL, TLE or purified polar lipid PGP (20 mg lipid) were prepared (starting lipid:antigen ratio of 2:1 w/w, for hydration) in water to just prior to the annealing step as described in Example 2 (i.e., un-encapsulated OVA was not removed from the archaeosome preparation). Next, while vigorously mixing the 1 ml suspension of archaeosomes by means of vortexing, 0.1 to 1.0 M stock solution of $CaCl_2$ in water was added dropwise. As the $CaCl_2$ was added, the suspension turned milky and visible precipitate formation was observed. Calcium addition was stopped when no additional new precipitate was being seen to be formed.

The preparation was viewed under phase contrast microscopy (ca 1250× magnification) to verify that the typical, individual, very small, spherical vesicle structures were absent or very minimal, and larger aggregates with phase bright surface perimeters (typical AMVAD structures under phase contrast) were predominant (FIG. 1). If large numbers of separate, individual, small archaeosomes were evident (observed as small, dot-like structures at this magnification of ca 1250× under phase contrast microscopy), more $CaCl_2$ was added in further step-wise additions, and the microscopic observations repeated in between, till only typical AMVAD structures were observed.

At this stage, the bulk of the AMVAD structures form a precipitate that settles to the bottom of the tube, leaving a clear supernatant at top. The total amount of $CaCl_2$ added, and the final volume of the preparation were noted, to calculate the molar ratio of lipid:Ca, and the $CaCl_2$ concentration in the AMVAD preparation/suspension at this stage. After 0-18 h storage at 4-7° C. (no specific time requirement, done as per convenience), the preparation was centrifuged (12,000×g for 30 min.), and the AMVAD pellet was washed in water containing the same concentration of $CaCl_2$ as in the preparation above. It was verified that one washing step was sufficient to remove free, soluble antigen from the formulation. The washed AMVAD formulation was re-suspended into final volume of 1 ml water containing the same concentration of $CaCl_2$ as in the preparation above, and stored at refrigeration temperature (4-7° C.) until required for use.

Based on the specific polar lipid used for making the archaeosomes and the concentration of the lipid(s), the amount of $CaCl_2$ (or other cations, or positively charged ion) added would need to be varied for making the AMVAD formulation, since sufficient amount of positively charged ions would be required to sufficiently interact with the negative charges contributed by the polar lipid and the added antigen. Typically for OVA/ or BSA/Ms AMVAD prepared by the standard protocol described above, the molar ratio of TPL:Ca (the MW of lipids in all TPL extracts being taken as 1000) in the antigen/AMVAD formulation was 1:1 (equivalent to a w/w ratio of 25:1), and the concentration of $CaCl_2$ in the formulation at this stage was 14.9 mM. These figures for $CaCl_2$ were similar in the case of making empty Ms AMVAD also.

The antigen/Ms AMVAD formulations were washed, re-suspended in water supplemented with 14.9 mM $CaCl_2$, and stored till required, as described above. At lower molar ratio of lipid:Ca (e.g. 1:0.5), there was little evidence of the typical Ms AMVAD or antigen/Ms AMVAD structure formation, and most of the archaeosomes remained as individual, small vesicles as evidenced by phase contrast microscopic examination. Larger batches of the AMVAD formulation can be made by proportionally scaling up the above method, or by other alternate means that would essentially provide the same conditions as described above, for converting archaeal polar lipids to archaeosomes and the archaeosomes into the AMVAD structures. For the preparation and storage of archaeosomes and AMVAD structures, no precautions were taken to exclude air or oxygen.

For making OVA/Ms TLE archaeosomes and converting these into OVA/Ms TLE AMVAD, the procedure was the same as described above for making of OVA/Ms TPL AMVAD. The molar ratio of TLE:Ca and the final concentration of $CaCl_2$ in the suspension were similar to those noted above for Ms TPL AMVAD.

For converting OVA/ or BSA/Hs archaeosomes into OVA/Hs AMVAD or BSA/Hs AMVAD, prepared as described above for Ms AMVAD, the amount of calcium required was much higher, typically requiring a molar ratio of TPL:Ca of 1:15 for conversion to Hs AMVAD, with the resultant $CaCl_2$ concentration in the suspension being ca 172 mM. The Hs AMVAD formulations were stored at 4-7° C., in the same concentrations of $CaCl_2$ till required for immunization.

For preparing empty *T. acidophilum* AMVAD or OVA/Ta AMVAD, empty or OVA-loaded Ta archaeosomes were prepared as described in Example 2. For conversion of the Ta archaeosomes into AMVAD structures, $CaCl_2$ was added as described for preparing Ms AMVAD. Typically the molar ratio of TPL:Ca in Ta AMVAD and OVA/Ta AMVAD was 1:5 and the concentration of $CaCl_2$ in the suspension was ca 50 mM. The Ta AMVAD formulations were stored at 4-7° C. in the same concentration of $CaCl_2$ till required for immunization.

For preparing OVA/PGP AMVAD, PGP archaeosomes with encapsulated OVA were prepared as described for OVA/Ms archaeosomes, and these were converted to AMVAD as described above for Ms AMVAD. The molar ratio of PGP:Ca was 1:1 and the concentration of $CaCl_2$ in the suspension was ca 91 mM. The OVA/PGP AMVAD formulations were stored at 4-7° C. in the same concentration of $CaCl_2$ till required for immunization.

At molar ratios of archaeal polar lipid:Ca of 1:0.5, there was minimal conversion of archaeosomes to AMVAD structures. This was observed for all the above archaeosome types prepared from different archaeal polar lipids.

Besides microscopic observation to verify that the structures obtained by cation addition to archaeosomes were indeed AMVAD structures (exhibiting the typical appearance under phase contrast microscopy), a further confirmatory step was made. It was observed that addition of a minimum 2-fold excess EDTA (over the added cation concentration) to an aliquot of AMVAD formulation resulted in the conversion of the AMVAD structures into large, unilamellar and multilamellar archaeosomes.

The AMVAD formulations were characterized for particle size, dry weight, and for antigen loading. Unless indicated otherwise, the mean particle width of the AMVAD structures (single and multi-AMVAD structures) was determined by taking ocular micrometer measurements under phase contrast optics, usually from 20-50 random measurements per formulation.

The dry weight of the lipids constituting the AMVAD preparation was determined by drying an aliquot of the formulation to a constant weight (at 50° C.), and subtracting the corresponding dry weight of the $CaCl_2$ in the suspension and the amount of antigen (determined as described below) as applicable.

The amount of OVA or BSA (or other soluble protein antigen) in AMVAD formulations was determined by Lowry assay of de-lipidated samples as described in Example 2 above for determining the encapsulated proteins in archaeosomes. Semi-quantitative verification of the antigen loading in AMVAD formulations was also done by SDS-PAGE analyses as described in Example 2 for archaeosomes. Unless stated otherwise, all of the data on the protein antigen determinations reported herein are based on the Lowry assays. The antigen loading is reported at µg antigen/mg lipid.

All AMVAD formulations were stored at refrigeration temperature (4-7° C.), until required for use. The formulations were stable (<10% leakage of antigen into solution) at least for over 1 year of storage. Just prior to use for each immunization, aliquots of the AMVAD formulations were diluted to the required immunization dose, in final concentration of 0.85% saline/15 mM $CaCl_2$ (pH 7.1).

Unless indicated otherwise, all AMVAD formulations described in the disclosure were prepared by the standard protocol described above, all the AMVAD formulations were prepared from the TPL extracted from the indicated archaeal species with the specified antigen being associated therein, and all the formulations were characterized as described in this Example. The nomenclature used for describing the AMVAD formulations, for example, was as follows, OVA/Ms AMVAD indicates that the AMVAD formulation was prepared from the TPL extracted from *M. smithii*, and OVA was the antigen loaded/associated with the AMVAD structures. Empty AMVAD formulation (in the absence of an antigen) made from *M. smithii* TPL, would be referred to as empty Ms AMVAD. When AMVAD formulations were prepared from polar lipids other than the TPL, these would be specified, for example, OVA/Ms TLE AMVAD would indicate that the AMVAD formulation with OVA antigen loaded/associated was made from the TLE (total lipid extract comprising the TPL and neutral lipids) obtained from *M. smithii*.

The typical, average loading of OVA in Ms AMVAD, Hs AMVAD, Ta AMVAD, and Ms TLE AMVAD formulations prepared by the standard protocol as described above was 30-87 μg OVA/mg lipid. The typical average width of the empty or antigen loaded Ms AMVAD, Hs AMVAD, Ta AMVAD and Ms TLE AMVAD structures consisting of several individual AMVAD structures clumped together (multi-AMVAD structure) was 15-35 μm. However, it was also determined that if need be, a 15-30 min period of vortexing of the formulation, in the presence of few glass beads, resulted in the reduction of the average width of the multi-AMVAD structures to <10 μm, without significant release (less than 10%) of the AMVAD-associated OVA into the solution. In such a preparation, a high proportion of single AMVAD structures of average widths of 5 μm or less, were observed.

As per the standard protocol above for converting archaeosomes to AMVAD structures, archaeosomes were not annealed before addition of $CaCl_2$. It was observed that for the conversion of empty or antigen-loaded archaeosomes into AMVAD structures, annealing of archaeosomes did not affect their subsequent conversion to AMVAD structures. As such, the standard protocol did not involve annealing the archaeosomes prior to their conversion to AMVAD structures.

The methods described in Example 3 for making AMVAD formulations can be scaled up, keeping in mind the need to maintain the indicated molar ratios of lipid:Ca and the requisite concentration of $CaCl_2$ or other substitute cation in the preparation. Also, the starting ratio (w/w) of the lipid:antigen can be varied at the stage of encapsulating antigen in the archaeosomes, to obtain different amounts of antigen loading per unit lipid in the subsequent AMVAD formulation. One skilled in the art will recognize that the mixing of archaeosomes while adding cations for conversion to AMVAD structures can be achieved by other methods of mixing besides vortexing.

Although various preferred methods are as described, one skilled in the art will recognize that AMVAD formulations can be prepared from archaeosomes by any other methods, such as dialysis against a cation solution, which essentially replicate the method described above for the requisite extent of interaction of the inherently negatively charged archaeal polar lipid with positively charged ions. It is also expected that an appropriate concentration of other multivalent organic or inorganic cations will achieve the same effect for converting archaeosomes into AMVAD structures with the resultant characteristics and utility described herein as obtained by the use of divalent $Ca^{2+}$ added as $CaCl_2$.

Example 4

Preparation of OVA/Ms AMVAD Formulation Using Archaeosome Formulation after the Un-Encapsulated OVA has been Removed Unilamellar Ms archaeosome formulation was prepared and the un-encapsulated OVA was removed, as described in Example 2. This archaeosome formulation was then converted into OVA/Ms AMVAD formulation by addition of $CaCl_2$ and the resultant AMVAD formulation was washed and characterized, as described in Example 3. The antigen loading was 50.3 μg OVA/mg lipid, and the average diameter of the multi-AMVAD structures was ca 30 μm. The appearance under phase contrast microscopy, the molar ratio of lipid:Ca (1:1), and the $CaCl_2$ concentration (14.9 mM) in the formulation suspension were similar to that for OVA/Ms AMVAD prepared by the standard protocol in Example 3. This formulation (OVA⁻/Ms AMVAD, un-encapsulated OVA removed from archaeosome formulation prior to conversion to AMVAD) was stored and diluted to the immunization dose as described for the standard protocol in Example 3.

Example 5

Preparation of OVA/AMVAD Formulations by Admixing OVA with Empty Archaeosomes and then Converting to AMVAD by Adding $CaCl_2$ Empty, unilamellar Ms or Hs archaeosomes from 20 mg of respective TPL were prepared as described in Example 2, but in 0.9 ml hydration volume and to just prior to the archaeosome annealing step. The empty Ms and Hs archaeosome suspension was supplemented with 0.1 ml of an appropriate OVA stock solution so as to effectively add 0.90 mg and 0.61 mg OVA respectively, to these suspensions. Each suspension was mixed by brief period of vortexing. These suspensions were converted into AMVAD formulations by $CaCl_2$ addition as described in Example 3, except that the resultant AMVAD formulations were not washed to remove any free OVA in solution (un-associated with AMVAD structure) that may be present in the AMVAD formulation.

The molar ratio of lipid:Ca and the mM $CaCl_2$ concentration of these AMVAD suspensions were similar to the OVA/Ms AMVAD and OVA/Hs formulations respectively, that were made by the standard protocol in Example 3. The ratio (w/w) of TPL:OVA (total OVA, not just the AMVAD structure associated) in the OVA/Ms AMVAD-ANW and OVA/Hs AMVAD-ANW formulation (ANR, archaeosomes admixed with antigen and AMVAD formulation not washed to remove any free, soluble antigen) was the same as the starting lipid:antigen (TPL:OVA) ratios (w/w) of 22.2:1 and 32.8:1 respectively, since none of the starting OVA was removed during preparation (e.g. by washing). About 21% and 33% of the total OVA in the OVA/Ms AMVAD-ANW and OVA/Hs AMVAD-ANW respectively, was associated with the AMVAD structures and the balance being in free solution.

Under phase contrast microscopic observation, these AMVAD preparations were similar in appearance to those prepared by the standard protocol in Example 3 (FIGS. 1E-1F). The formulations were stored at refrigeration temperature, in the presence of the same respective concentrations of $CaCl_2$ as required for making each preparation. Just prior to immunization, the formulations were diluted to the immunization dose in final concentration of 0.85% NaCl/15 mM $CaCl_2$.

Example 6

Preparation of OVA/AMVAD Formulations without Removing the Un-Encapsulated OVA from Archaeosome Suspensions and without Washing the AMVAD Formulations Unilamellar archaeosomes with encapsulated OVA, were prepared from Ms TPL or Hs TPL to just prior to the archaeosome annealing step as described in Example 2, except that the starting ratio (w/w) of lipid:antigen (TPL:OVA) for hydration of the lipids to encapsulate OVA into archaeosomes was changed to 22.2:1 for Ms archaeosomes or 32.9:1 for Hs archaeosomes, from the usual 2:1 ratio. The rest of the procedure for converting the archaeosomes to AMVAD structures was as per the standard protocols described in Example 3, except that once the OVA/AMVAD formulations were made by addition of CaCl$_2$, these were not washed to remove any free OVA (soluble in the supernatant) in the AMVAD formulation.

Under phase contrast microscopy, these formulations looked similar to that of the AMVAD structures made by the standard protocols in Example 3. The formulations were stored at 4-7° C., in the same concentrations of CaCl$_2$ as when prepared, till required for immunization.

The molar ratio lipid:Ca in these formulations was 1:1 for OVA/Ms AMVAD-NW (14.9 mM CaCl$_2$ in the formulation suspension) and 1:15 for OVA/Hs AMVAD-NW (172 mM CaCl$_2$ in the formulation suspension). The ratio (w/w) of TPL:OVA in these AMVAD formulations (total OVA including that in free solution and not associated with AMVAD structure) was the same as the starting TPL:OVA ratios, respectively, since none of the starting material was removed during preparation (e.g. by washing). About 19% and 25% of the total OVA in the OVA/Ms AMVAD-NW and OVA/Hs AMVAD-NW formulations respectively, was associated with the AMVAD structures and the balance being in free solution.

The formulations were stored at refrigeration temperature, in the presence of the same respective concentrations of CaCl$_2$ as required for making each preparation. Just prior to immunization, the formulations were diluted to the immunization dose in final concentration of 0.85% NaCl/15 mM CaCl$_2$.

Example 7

Characterization of AMVAD Structures by Phase Contrast Microscopy

Empty Ms and Hs AMVAD, OVA/Ms AMVAD, and OVA/Hs AMVAD formulations were prepared by the standard protocols described in Example 3. The AMVAD formulations OVA/Ms AMVAD-ANW and OVA/Hs AMVAD-ANR, made by admixing empty archaeosomes with OVA prior to conversion to AMVAD, were prepared as described in Example 5. Well mixed aliquots of these formulations were viewed under phase contrast microscopy (Olympus Model BX51 TF microscope, Olympus America, Melville, N.Y., USA) and observations were recorded using Model Micropublisher[R] 5.0 RTV camera (QImaging, Burnaby, British Columbia, Canada) and QCapture Pro[R] software (QImaging, Canada).

Under phase contrast microscopy, the AMVAD structures appear as large particulates (several micrometers in width) which predominantly vary from roughly round to slightly oblate in shape (FIG. 1A-1F). In all formulations, the structures exhibit a typical appearance with phase-bright perimeters and some phase bright areas within. Each of the structures in FIGS. 1A-1F appears as a large aggregate composed of smaller, multiple individual aggregates. For example, in FIG. 1A, a minimum of 5 and perhaps 7 individual aggregates are discernible as part of the larger aggregate. The typical average width of the large aggregates is about 20 μm. Smaller individual aggregates can also be seen (out of focus) in FIGS. 1A, 1C, and 1F. The AMVAD structures vaguely appear to comprise aggregates of spherical structures, the latter being especially evident at the outer edges of the aggregates when the image is focused in and out. It was observed that AMVAD structures prepared by the standard protocol (Ms or Hs) have similar appearance to those of the corresponding AMVAD formulations prepared by the alternate, simplified methods. Also, for each of Ms or Hs AMVAD preparation, there are no observable differences in the appearance of empty and OVA/AMVAD structures. Under phase contrast microscopy, unilamellar archaeosomes (which have an average diameter of 100 nm) appear as barely visible, tiny, spherical objects.

Example 8

Characterization of AMVAD Structures by Electron Microscopy

Empty and OVA/AMVAD formulations from the TPL of *M. smithii* and *H. salinarum* were prepared as described in Example 3. Empty Ms archaeosomes were prepared from Ms TPL as described in Example 2. Small aliquots of well mixed formulations were put on freshly cleaved mica sheet and quickly frozen by plunging in liquid Freon, and then stored in liquid nitrogen. The samples were freeze-etched (Balzer Model BAF 400D freeze etcher, Balzer Union, Liechtenstein, Germany) for 1 h at −70° C. The etched specimens were platinum shadowed, coated with carbon (Technic Hummer[R] coater, anatech, Ltd., Springfield, Va., USA), and viewed in a scanning electron microscope (Philips XL 30 ESEM, FEI Company, Hillsboro, Oreg., USA).

Pictures of representative structures were taken and are presented (FIG. 2A-2D). FIG. 2A shows that the Ms archaeosome formulation predominantly consists of small, individual, spherical vesicles of average diameters of ca 100 nm, with no evidence of vesicle aggregation or clumping. Both empty Ms AMVAD (FIG. 2B) and OVA/Ms AMVAD (FIG. 2C) structures consist of large, spherical structures which have aggregated together like bunches of grapes. In each of FIG. 2B and FIG. 2C, it is seen that multiple, individual, smaller aggregate structures (each resembling a single bunch of grapes) have clumped together into larger aggregates. The individual smaller aggregate, each comprising of multiple spherical structures clumped together, is referred to as a single or individual AMVAD structure (similar to a single bunch of grapes). The larger aggregate, consisting of multiple, smaller individual aggregates which have further clumped together (like multiple bunches of grapes), is referred to as multi-AMVAD structure. For example, in each of FIG. 2B and FIG. 2C, several individual AMVAD structures are discernible as part of multi-AMVAD structures, and each individual AMVAD structure is less than 10 μm in width.

The term AMVAD structure includes single and multi-AMVAD structures. It is clearly seen that the AMVAD structure is distinct from that of the archaeosomes (FIG. 2A) which appear as significantly smaller, individual vesicles, of about 100 nm average width. It is seen that the empty Ms AMVAD (FIG. 2B) and OVA/Ms AMVAD (FIG. 2C) structures are similar in appearance. The structures of OVA/Hs AMVAD (FIG. 2D) are not as clearly visible as for the Ms AMVAD, possibly due to the higher calcium causing a layer of precipitate on top of the structures. However, some semblances of grape like bunches of spherical structures are evident.

Example 9

Characterization of AMVAD Structures by Fluorescence Microscopy

To determine if the AMVAD structures comprise aqueous compartment(s) or capture an aqueous volume, as would appear to be from phase contrast and electron microscopy observations indicative of spherical structures that have aggregated, AMVAD formulations were prepared using 5(6)-carboxyfluorescein (CF, Sigma Chemical Co., cat #C-7153, MW 376.32), a highly water soluble fluorescent dye (ca 490 nm excitation and ca 515 emission cut off). At 1.5 mM concentration, CF is fluorescent, and CF has been recommended and used as a marker for aqueous compartments in closed, lipidic structures such as liposomes and archaeosomes.

A formulation of unilamellar Ms archaeosomes with encapsulated CF was prepared as described for making OVA/Ms archaeosomes in Example 2, except that the hydration of the lipid was done in a solution of 1.5 mM CF in water adjusted to neutral pH, instead of in an OVA solution. The archaeosomes were not annealed. Un-encapsulated OVA was removed by ultracentrifugation and washing, as described for removing un-encapsulated antigen in Example 2, and the Ms archaeosomes with encapsulated CF (CF/Ms archaeosomes) were resuspended in water at neutral pH. The suspension of CF/Ms archaeosomes was converted into CF/Ms AMVAD formulation by addition of $CaCl_2$, and the formulation was washed to remove free CF, as described for making OVA/Ms AMVAD formulation by the standard protocol in Example 3.

The washed CF/Ms AMVAD formulation was resuspended in water supplemented with the initial concentration of $CaCl_2$ required to make the AMVAD formulation. Preparations of Ms AMVAD and Hs AMVAD with CF were also prepared by admixing protocols as described for OVA/Ms AMVAD and OVA/Hs AMVAD preparations in Example 5, with minor changes. In this case, the suspensions of empty, unilamellar, Ms or HS archaeosomes in water (at neutral pH) were subsequently supplemented with CF to give a final CF concentration of 1.5 mM, instead of the supplementation of empty archaeosomes with OVA.

The suspensions of archaeosomes admixed with CF were then converted into AMVAD structures by adding $CaCl_2$ as described in Example 5. The free CF was removed by washing the AMVAD formulations as described for washing OVA/Ms AMVAD preparation in Example 3, and re-suspended in water supplemented with the respective initial concentrations of $CaCl_2$ required to make the Ms AMVAD-ACF and the Hs AMVAD-ACF formulations (ACF, CF admixed with pre-formed archaeosomes and then converted to AMVAD structure). The molar ratios of lipid:Ca and the concentrations of $CaCl_2$ in the CF/AMVAD formulations were the same as for the Ms and Hs AMVAD formulations described in Example 3.

The final preparations were observed by fluorescence microscopy (BX51 Olympus Microscope fitted with a reflected fluorescence system) using the appropriate excitation filter for optimal CF fluorescence. It was observed that Ms archaeosomes with the encapsulated CF appear as very small, spherical, single, fluorescent structures, as expected for closed vesicles with an aqueous capture volume (FIG. 3A). All of the AMVAD formulations made with CF (by the standard AMVAD making protocol or by the admixing protocol) were fluorescent, with the fluorescence intensity appearing to be uniform over the entire AMVAD structure (FIGS. 3B-3D). This demonstrates that the AMVAD structures have captured aqueous volume containing CF, resulting in the observed fluorescence of the structures. Structures lacking aqueous compartment(s) or an aqueous capture volume, would not contain encapsulated water soluble CF dye, and hence would not exhibit the type of fluorescence seen here with the AMVAD structures or with the archaeosomes.

Example 10

Preparation of Peptide/Ms AMVAD Vaccine Formulation

Listeriolysin is one of the virulence factors of the intracellular pathogen Listeria Monocytogenes. A dipalmitoylated 20-mer peptide ($PAM_2$-KSSKGYKDGNEYIVVEKK KK-OH; $PAM_2$-peptide (SEQ ID NO:1)), containing the known H-$2K^d$ MHC-Class-I-restricted-immunodominant nonamer epitope (GYKDGNEYI) (SEQ ID NO:1) of listeriolysin recognized by Balb/c mice, was synthesized as described previously (Conlan et al., 2001). The ($PAM)_2$-peptide (an example of an alkylated peptide) is hydrophobic in nature, and not readily soluble in water. The ($PAM)_2$-peptide was encapsulated into Ms archaeosomes, by a modified dehydration-rehydration procedure as described earlier (Conlan et al., 2001), with minor modifications such as changing the starting ratio (w/w) of lipid:antigen (TPL:peptide), and using water adjusted to pH12 for hydration.

Briefly, 20 mg of Ms TPL was converted into empty archaeosomes as described in Example 2 but to just prior to the annealing stage, and using 2 ml of deionized distilled water which had been adjusted to pH12 for hydration of the lipid film. To the archaeosome suspension was added 10 mg of the $PAM_2$-peptide dissolved in 0.6 ml dimethylsulfoxide. The suspension was subjected to a brief period (less than 5 min) of bath sonication to obtain unilamellar vesicles. The suspension was lyophilized, and rehydrated slowly in 1.0 ml of water prior-adjusted to pH 12, and incubated for 1 h at 35° C. (rotary shaker). After subjecting the suspension to a 2 min period of bath sonication, it was stored overnight (ca 18 h) at 5° C.

The suspension was ultracentrifuged (275,000×g for 1 h), and the pellet containing the archaeosomes with encapsulated $PAM_2$-peptide was re-suspended into 1.0 ml of water at neutral pH. This suspension was converted into $PAM_2$-peptide/Ms AMVAD formulation by drop-wise addition 0.1 M $CaCl_2$ and washed, as described for the standard protocol for making OVA/Ms AMVAD in Example 3. The molar ratio of TPL:Ca in this formulation was 1:4.5 and the concentration of $CaCl_2$ in the suspension was 37.5 mM. The loading of the $PAM_2$-peptide in the AMVAD formulation was ca145 μg/mg TPL, determined as described previously for archaeosome formulations containing $PAM_2$-peptide (Conlan et al., 2001).

Example 11

Preparation of Listeria monocytogenes Cell Free Extract AMVAD Formulations

Listeria monocytogenes is an intracellular pathogen which primarily invades the host via the gastrointestinal tract. Listeria monocytogenes strain 10403S (obtained from Dr. W. Conlan, Institute for Biological Sciences, National Research Council of Canada, Ottawa, Ontario, Canada) was cultured in Brain Heart Infusion (BHI) broth, cells were harvested in 0.85% saline, and were ruptured by 4 successive passages (68,900-103,350 KPa) through an Emulsiflex$^R$-05 high pressure homogenizer (Avestin Inc., Ottawa, Ontario, Canada). The lysate was centrifuged (ca 20,000×g, 120 min) and the supernatant was filtered through 0.22 μm Millex-GV$^R$ sterile filter (Millipore Corporation, Bedford, Mass., USA) to obtain the L. monocytogenes cell free extract (LMCE). The total protein content of LMCE was determined by Lowry assay using OVA as the standard, and the protein profile determined by SDS PAGE analyses. The LMCE was stored at 5° C. until required for use. For longer term storage before use, aliquots of LMCE were frozen and stored at −20° C.

Unilamellar Ms or Hs archaeosomes with encapsulated LMCE were prepared as described for OVA encapsulation in Example 2, with the following modifications—40 mg of TPL was dried down and hydrated using 2.0 ml of LMCE (20 mg total protein) that had been prior adjusted to pH 10 using 0.1

N NaOH. After size reduction and annealing of archaeosomes, the un-encapsulated LMCE was removed by ultracentrifugation (using pH 10 water for make up volume in the ultracentrifuge tube) as described for OVA/archaeosomes in Example 2, and re-suspended in 2 ml of water without pH adjustment. The suspension was centrifuged (1.5×g for 1 min) to remove the few larger particles, and the supernatant containing the archaeosomes was recovered. The archaeosomes were converted into AMVAD formulation by adding 0.1 M $CaCl_2$ as described in Example 3 for OVA/Ms AMVAD preparation. The molar ratio of lipid:Ca in the LMCE/Ms AMVAD suspension was 1:3.75 and the concentration of $CaCl_2$ was 51 mM. The molar ratio of lipid:Ca in the LMCE/Hs AMVAD suspension was 1:9.5 and the concentration of $CaCl_2$ was 124 mM. The formulations were washed as described for OVA/Ms AMVAD in Example 3, and re-suspended into 1.25 ml of water supplemented with the same concentration of $CaCl_2$ as in the original, respective AMVAD suspension. The protein loading in LMCE/Ms AMVAD and LMCE/Hs AMVAD formulation was 104.3 and 139.2 µg protein/mg lipid, respectively. The SDS PAGE protein profile of the AMVAD-associated protein in the formulations was similar to that of the starting LMCE material. Just prior to use for each immunization, an aliquot of the respective AMVAD formulation was diluted to the required immunization dose, in final concentration of 0.85% saline/15 mM $CaCl_2$ (pH 7.1).

Example 12

Preparation of *Francisella tularensis* LVS Cell Free Extract/Ms AMVAD Formulation

*Francisella tularensis* is a potent respiratory and systemic pathogen that infects humans and animals. Primary and secondary *F. tularensis* LVS infections are controlled by the host's $CD4^+$ and $CD8^+$ T-cell-dependent and -independent host defense mechanisms (Conlan et al., 1994). Freshly harvested *Francisella tularensis* LVS (ATCC 29684) cells were washed and resuspended in saline, and were lysed by two by successive passages (68,900-103,350 KPa) through an Emulsiflex$^R$-05 high pressure homogenizer (Avestin Inc., Ottawa, Ontario, Canada). The lysate was centrifuged (16,000×g for 90 min), the supernatant containing the cell-free extract was collected and plated on cysteine heart agar supplemented with 1% (w/w) haemoglobin to verify absence of viable cells, and the total protein content was determined by Lowry assay using BSA as the standard.

This cell free extract (LVSCE) in saline contained 5.5 mg protein/ml. Unilamellar Ms archaeosomes with encapsulated LVSCE were prepared as described for OVA encapsulation in Example 2, with the following modifications—40 mg of Ms TPL was dried down and hydrated using 2.5 ml of the LVSCE that had been prior adjusted to pH 11 using 3 N NaOH (w/w ratio of lipid:protein of 3:1). After size reduction and annealing of archaeosomes, the un-encapsulated LVSCE was removed by ultracentrifugation (using pH 11 water for make up volume in the ultracentrifuge tube) as described for OVA/archaeosomes in Example 2, and re-suspended in 2 ml of water without pH adjustment. The archaeosomes were converted into AMVAD formulation by adding 0.1 M $CaCl_2$ as described in Example 3 for OVA/Ms AMVAD preparation. The molar ratio of lipid:Ca in this suspension was 1:2.75 and the concentration of $CaCl_2$ was 50 mM. The formulation (LVSCE/Ms AMVAD) was washed as described for OVA/Ms AMVAD in Example 3, and re-suspended into 1.5 ml water supplemented with 50 mM $CaCl_2$. The protein loading in this formulation was 56.8 μg protein/mg lipid.

Example 13

Preparation of *Helicobacter pylori* Cell Free Extract/Ms AMVAD Formulation

*Helicobacter pylori* colonizes the gastric epithelium and it causes peptic ulcers, gastritis, and has been implicated in the development of gastric cancers. The protective immunity against *H. pylori* infection in humans is believed to be dependent of the presence of antigen-specific $CD4^+$ cells and probably also on mucosal IgA responses. The mouse-adapted Sydney strain of *H. pylori* (SS1) established by Lee et al. (1997), was cultivated in a 15 liter fermenter vessel using Brucella broth supplemented with 10% fetal bovine serum and Glaxo selective supplement (GSS) antibiotics (mg/l of amphotericin B, 5; vancomycin, 10; polymyxin B, 0.33; bacitracin, 20; nalidixic acid, 1.07). Cells washed and resuspended in saline, were lysed by 2 successive passages (68,900-103,350 KPa) through an Emulsiflex$^R$-05 high pressure homogenizer (Avestin Inc., Ottawa, Ontario, Canada), the lysate was centrifuged (16,000×g for 90 min), and the collected supernatant was plated on blood agar supplemented with defribrinized horse blood, to verify the absence of viable cells. The total protein content of the cell free extract (HPCE) was determined by Lowry assay using OVA as the standard, and the protein profile determined by SDS PAGE analyses. The HPCE was stored at 5° C. until required for use.

Unilamellar Ms archaeosomes with encapsulated HPCE were prepared as described for OVA encapsulation in Example 2, with the following modifications—20 mg of dried Ms TPL was hydrated in 2.5 ml of HPCE (10 mg total protein) and the archaeosome suspension was centrifuged (0.4×g for 2 min in a bench top centrifuge) to remove the few large particles. The archaeosomes were converted to AMVAD structures by addition of $CaCl_2$ as described in Example 3 for OVA/Ms AMVAD preparation. The molar ratio of lipid:Ca in this suspension was 1:5 and the concentration of $CaCl_2$ was 40 mM. The formulation was washed as described for OVA/Ms AMVAD in Example 3, and re-suspended into 1.6 ml water supplemented with 40 mM $CaCl_2$. The protein loading in this formulation was 239.7 μg protein/mg lipid. If the staring ratio (w/w) of TPL:protein was changed from 2:1 described above, to 4:1, the HPCE loading obtained was lowered to 141.5 μg protein/mg lipid. Just prior to each immunization, aliquots of the HPCE/Ms AMVAD formulation were diluted to the required immunization dose, in final concentration of 0.85% saline/15 mM $CaCl_2$ (pH 7.1).

Example 14

Preparation of *Streptococcus pneumoniae* PsaA/AMVAD Formulations

*Streptococcus pneumoniae* is common respiratory tract pathogen that has been recognized as a causative agent for pneumonia, bacteremia, meningitis and otitis media. Pneumococcal surface antigen A (PsaA), a well conserved protein in many *S. pneumoniae* strains, has been studied as a vaccine candidate for affording protection against pathogen carriage and the diseases it causes. Recombinant *E. coli* with a histidine-tagged gene (with the peptide linker GGGS) encoding the PsaA peptide, was constructed as described (Marra et al., 2002). This protein has the following sequence:

(SEQ ID NO: 2)
ASGKKDAASGQKLKVVATNSIIADITKNIAGDKIDLHSIVPIGQDPHEY

EPLPEDVKKTSEADLIFYNGINLETGGNAWFTKLVENAKKTENKDYFAV

SDGVDVIYLEGQNEKGKEDPHAWLNLENGIIFAKNIAKQLSAKDPNNKE

FYEKNLKEYTDKLDKLDKESKDKFNKIPAEKKLIVTSEGAFKYFSKAYG

VPSAYIWEINTEEEGTPEQIKTLVEKLRQTKVPSLFVESSVDDRPMKAV

SQDTNIPIYAQIFTDSIAEQGKEGDSYYSMMKYNLDKIAEGLAKGGGGS

HHHHHH.

The protein from the recombinant *E. coli* grown in 24 L fermenter vessel (Lauria broth supplemented with 0.2 mg/ml penicillin), was extracted in phosphate buffered saline as described (De et al., 2000), and frozen at −20° C. Prior to use for making vaccine formulations, the PsaA (PsaA with the histidine tag) was thawed, dialysed (dialysis tubing with a 10KD MW cutoff) against 0.85% saline (in 1000 ml of saline, overnight at 4° C.) and then concentrated to ca 7 mg protein/ml using an Amicon Ultra-4$^R$ (Millipore Canada Ltd., Etobicocke, Ontario, Canada) centrifugal filter device with a 10 KD MW cutoff. The concentration of PsaA was determined by Lowry assay using OVA as the standard, and the protein was characterized by SDS PAGE and Western blot analyses.

Unilamellar Ms archaeosomes with encapsulated PsaA were prepared as described for OVA encapsulation in Example 2, with the following modifications—20 mg of Ms TPL was dried down and hydrated using 1.0 ml of the PsaA solution prepared above (7.4 mg protein) that had been prior adjusted to pH 10 using 0.1 N NaOH (w/w ratio of lipid:PsaA of 2.7:1). After size reduction of the archaeosomes, the preparation was annealed, the un-encapsulated protein was removed by ultracentrifugation (using pH 10 saline for making up volume in the ultracentrifuge tube) as described for OVA/archaeosomes in Example 2, and the archaeosomes re-suspended in 1 ml of water without pH adjustment.

The archaeosomes were converted into AMVAD formulation by adding 0.1 M $CaCl_2$ as described in Example 3 for OVA/Ms AMVAD preparation. The molar ratio of lipid:Ca in the PsaA/Ms AMVAD suspension was 1:1.5 and the concentration of $CaCl_2$ was 22 mM. The formulation was washed as described for OVA/Ms AMVAD in Example 3, and re-suspended into 1.0 ml water supplemented with 22 mM $CaCl_2$. The PsaA loading in PsaA/Ms AMVAD formulation was 30 µg/mg lipid. The SDS PAGE profile of the AMVAD-associated protein in the formulations was similar to that of the starting PsaA protein. The AMVAD formulation was stored at refrigeration temperature. Just prior to use for each immunization, an aliquot of the AMVAD formulation was diluted to the required immunization dose, in final concentration of 0.85% saline/15 mM $CaCl_2$ (pH 7.1).

The PsaA/Hs AMVAD archaeosome formulation was prepared as described for OVA/archaeosome formulations in Example 2, with the following changes—10 mg of Hs TPL was hydrated in 0.5 ml of PsaA stock solution (3.12 mg PsaA) and processed right up to the completion of the annealing step in Example 2. The archaeosome formulation was converted into AMVAD formulation by addition of 1 M $CaCl_2$ as described in Example 3. The molar ratio of lipid:Ca in the PsaA/Hs AMVAD suspension was 1:17.5 and the concentration of $CaCl_2$ was 243 mM. The psaA/Hs AMVAD formulation was washed as described for OVA/Ms AMVAD in Example 3, and re-suspended into 0.5 ml water supplemented with 243 mM $CaCl_2$. The PsaA loading in PsaA/Hs AMVAD formulation was 26.2 µg/mg lipid. The SDS PAGE profile of the AMVAD-associated protein in the formulation was similar to that of the starting PsaA protein. The AMVAD formulation was stored at refrigeration temperature. Just prior to use for each immunization, an aliquot of the AMVAD formulation was centrifuged (12,000×g for 30 min) and the pellet was resuspended to the required immunization dose in final concentration of 0.85% saline/15 mM $CaCl_2$ (pH 7.1).

Example 15

Preparation of *E. coli* O-Chain-BSA/Ms AMVAD (O-Chain/Ms AMVAD) Formulation

*Escherichia coli* O157:H7 is an enteric bacterial pathogen that is associated with severe illness in humans, including haemolytic uremic syndrome, leading in many instances to kidney failure and death. *E. coli* O 157:H 7 O-chain polysaccharide (O-antigen) was isolated and characterized as described previously (Perry et al., 1986). The O-antigen-bovine serum albumin conjugate (O-chain-BSA) was prepared and the proportion of O-chain in the conjugate was determined as described previously for making O-chain-horse serum albumin conjugate (Conlan et al., 1999). The amount of BSA was determined by Lowry protein assay using BSA as the standard. The O-chain-BSA conjugate in 0.9% saline was at a concentration of 2.46 mg/ml, of which O-chain was 0.72 mg/ml and the BSA was 1.72 mg/ml (ratio, w/w, of BSA:O-chain of 1:0.413).

Unilamellar Ms archaeosomes with encapsulated O-chain-BSA conjugate was prepared as described for OVA encapsulation in Example 2, with the following modifications—20 mg of Ms TPL was dried down and hydrated using 1.0 ml of the conjugate solution prepared above (2.46 mg conjugate) which had been prior adjusted to pH 9 using 0.1 N NaOH (w/w ratio of lipid:conjugate of 8.1:1). After size reduction of the archaeosomes, the preparation was centrifuged (1.5×g for 1 min) to remove the few large particles, and the supernatant containing the archaeosomes was collected. After annealing the archaeosomes, the un-encapsulated conjugate was removed by ultracentrifugation (using pH 9 water for make up volume in the ultracentrifuge tube) as described for OVA/archaeosomes in Example 2, and re-suspended in 1 ml of water without pH adjustment.

The archaeosomes were converted into AMVAD formulation by drop wise addition of 0.5 M $CaCl_2$ stock solution, as described in Example 3 for OVA/Ms AMVAD preparation. The molar ratio of lipid:Ca in the O-chain-BSA/Ms AMVAD (O-chain/Ms AMVAD) suspension was 1:1.9 and the concentration of $CaCl_2$ was 50 mM. The BSA loading in O-chain/Ms AMVAD formulation was 92.9 µg/mg lipid, with the calculated loading of the O-chain as 38.1 µg/mg lipid based on BSA:O-chain ratio of 1:0.413. The AMVAD formulation was stored at refrigeration temperature (4-7 C)°. Just prior to use for each immunization, an aliquot of the AMVAD formulation was diluted to the required immunization dose, in final concentration of 0.85% saline/15 mM $CaCl_2$ (pH 7.1).

Example 16

Preparation and Characterization of OVA/DOPS-Chol Cochleates

Cochleates containing OVA were prepared from unilamellar liposomes comprising a 9:1 mixture (w/w) of synthetic ester lipid 1,2-Dioleoyl-sn-Glycero-3-[Phospho-L-Serine] sodium salt (DOPS lyophilized powder; obtained from Avanti Polar Lipids Inc.; Alabaster, Ala., USA; MW of 810.04; cat

830035P, Lot #181PS-214) and cholesterol (Sigma Chemical Co.; Cat # C8667), by the standard cochleate method of direct addition of $CaCl_2$ as described (Gould-Fogerite and Mannino, 1993). Briefly, a dried film of 20 mg mixture of the DOPS-cholesterol was hydrated in 1 ml of OVA stock solution (10 mg OVA/ml water) and converted to unilamellar liposomes by bath sonication, by avoiding exposure to air as described (Jin et al., 2000). Ten microliter aliquots of 0.1 M $CaCl_2$ stock solution were added to the liposome suspension with mixing in between each addition, till the total concentration of calcium ions equaled to one half the molar concentration of DOPS constituting the liposomes, and then additional $CaCl_2$ was added to achieve a 3 mM excess over that already added, as described (Gould-Fogerite and Mannino, 1993).

The cochleates were washed and re-suspended in water containing the same concentration of $CaCl_2$ as in step above for conversion of liposomes to cochleates, as described for OVA/Ms AMVAD in Example 3. The cochleates were stored under nitrogen gas phase till immediately required for use. The cochleates were characterized for size, OVA loading etc., as described for OVA/Ms AMVAD in Example 3. The typical loading of OVA in DOPS-cholesterol cochleates was 25-35 µg OVA/mg DOPS plus cholesterol, and the average width of the cochleate structures was 15.8±5.95 µm. Just prior to use for each immunization, an aliquot of the cochleate formulation was diluted to the required immunization dose, in final concentration of 0.85% saline/15 mM $CaCl_2$ (pH 7.1).

Example 17

Mice, Immunizations, Sample Collection, Antibody and CTL Assays

Efficacy of various vaccine formulations in eliciting mucosal and systemic immune responses was evaluated in murine models. Specific-pathogen-free, female, Balb/c and C57BL/6 mice were purchased from Charles Rivers Laboratories (Montreal, P.Q., Canada). They entered experiments when they were 6-12 weeks old. Mice were housed and used as per the Canadian Council on Animal Care Guide to the Care and Use of Experimental Animals. Further, all animal care/use protocols were approved by the Institutional Animal Care Committee.

Groups of mice (n=5-10; mostly n=5, unless indicated otherwise) were immunized subcutaneously (s.c.) at the neck (0.1 ml volume), intranasally (i.n., 50 µA volume applied alternately, drop by drop, to the nares) to anesthetized (i.p. injection of saline buffered mixture of ketamine and xylazine at 0.1 mg and 0.05 mg/g body weight of mouse, respectively; 0.25 ml volume) mice, or perorally (p.o.) using a gavage needle (0.25 ml volume). All AMVAD formulations were diluted to the immunization dose in final concentration of 0.85% saline/15 mM $CaCl_2$ (pH 7.1) just prior to use. Archaeosome formulations were diluted to the immunization dose in 0.85% saline (pH 7.1). Unless indicated otherwise, the immunization schedule was at 0, 7 and 21 d, and the antigen dose was 10 µg/mouse/immunization.

At the various indicated time periods, samples were collected for immunology assays. Blood was collected from the tail veins (ca 0.1 ml), or by cardiac puncture of euthanized mice in the case of final sampling. The blood collected in Microtainer[R] serum separator tubes (Becton and Dickinson, Franklin Lakes, N.J., USA) was allowed to clot (1 h at 5° C.), the sera were separated by centrifugation (10,000×g for 5 min) and stored at −20° C. till assayed. For fecal samples, three to four freshly voided pellets (mouse temporarily put in a clean container) were put into a 1.5 ml micro-tube stored on ice. Fecal extraction buffer (5% fetal bovine serum, 0.02% sodium azide in 1× phosphate buffered saline) pre-cooled to 5° C., was added (0.1 ml per 0.01 g wet weight of feces). After soaking the fecal pellets for 30-60 min, they were broken up with a metal spatula. The tube was vigorously vortexed, let to stand at room temperature for 5-10 min, vortexed again, and centrifuged (16,000×g for 10 min). The supernatant was collected and stored at −20° C. till used for assay.

Vaginal wash samples were collected by slowly injecting and withdrawing (3-4 times) a 0.05 ml aliquot of 1×PBS (pH 7.2 phosphate buffered saline—8.0 g/l NaCl, 0.2 g/l $KH_2PO_4$, 1.15 g/l $Na_2HPO_4$, 0.2 g/l KCl) into the mouse vagina by means of a P100 pipette. The sample (ca 0.05 ml) was stored at −20 C until used for assay. Nasal wash and bile samples were collected after euthanizing the mice by $CO_2$ asphyxiation. For bile samples, the gall bladder was put into a 0.5 ml micro-tube and 0.1 ml of the fecal extraction buffer was added. The gall bladder was "macerated" by cutting with scissors. The tube was vortexed gently, and centrifuged (10,000×g for 5 min). The supernatant was collected and stored at −20° C. until used for assay. For nasal wash samples, the trachea was exposed by removing the skin and soft tissue. A small cut was made and a lavage tube inserted 0.5-1.0 cm towards the head. The nasal cavity was flushed with 1 ml PBS and the wash was collected from the anterior opening of the nose. The nasal wash was stored at −20° C. until used for assay.

Various antibody subtypes (IgA, IgG, IgG1 and IgG2a) specific for OVA, BSA or other antigens, were measured by indirect enzyme-linked immunosorbent assays (ELISA). Briefly, 96-well flat-bottom Immunolon $2^R$ microplates (Dynex Technologies Inc., Chantilly, Va., USA) were coated with 100 µl of the antigen in carbonate buffer (pH 9.6, 15 mM sodium carbonate and 35 mM sodium bicarbonate) at 4° C. overnight. For each specific antibody type measured, the optimal antigen (OVA, BSA, LMCE, LVSCE, HPCE or PsaA) coating concentration (µg/well) was first determined by conducting test assays using a positive antibody control sample.

For the O-chain-BSA conjugate antigen, the plates were coated with *E. coli* O157:H7 LPS since the O-chain does not adhere reliably to the ELISA plates. The antigen-coated plates were washed two times with PBS-0.05% Tween (washing solution), and blocked with 5% bovine serum in PBS (blocking buffer, 1 h at room temperature). Aliquots (100 µl/well) of appropriately diluted samples (diluted in blocking buffer) were added to duplicate wells, and the plates were incubated at room temperature for 3 h.

Unless indicated otherwise, the sample dilutions used for the ELISA assays were 1:2 for fecal and nasal wash IgA, 1:20 for vaginal, serum and bile IgA, 1:2000 for serum IgG and IgG1, and 1:200 for serum IgG2a. After washing the plates 3×, secondary antibodies were added. Alkaline phosphatase-conjugated goat antibodies specific for mouse IgA (1:1000 diluted), IgG1 or IgG2a (1:2000 diluted) or IgG (1:3000 diluted) were added (all from Caltag Laboratories, Burlingame, Calif., USA), and plates incubated for 1 h at room temperature. Color reactions were developed by the addition of p-nitrophenyl phosphate (pNPP) substrates (Kirkegaard and Perry Laboratories, Inc., Gaithersburg, Md., USA), and optical density was measured at 405 nm after 10-60 min incubation periods, using an automated ELISA plate reader (Model 354,Thermo Labsystems, Helsinki, Finland) and Multiskan Accent[R] software (Thermo Labsystems). Antibody titres are represented as mean optical density units±SD for each group, at the indicated sample dilution used for the assay.

For conducting cytotoxic (cytolytic) T Lymphocyte (CTL) assays, EL-4 and EG.7 (subclone of EL-4 that has been stably transfected with the gene encoding for OVA expression), cell lines were obtained from the American Type Culture Collection (ATCC, Manassas, Va., USA). Both cell lines were maintained in RPMI 1640 medium (Life Technologies, Grand Island, N.Y.) supplemented with 8% fetal bovine serum (FBS, Invitrogen Canada, Inc., Burlington, Ontario, Canada), except that 400 μg/ml G418 supplement (Invitrogen Canada Inc.) was also added for maintaining the EG.7 cell line. All cells were cultured at 37° C. in a humidified atmosphere of air containing 8% $CO_2$. Approximately $30 \times 10^6$ spleen cells (cells pooled from two spleens obtained from euthanized mice), obtained from spleens of immunized or naïve mice, were co-cultured with $5 \times 10^5$ irradiated EG.7 cells, in 10 ml of RPM1 1640 supplemented with 8% FBS and 0.1 ng/ml IL-2 (Becton Dickinson Canada Inc., Oakville, Ontario, Canada) contained in 25 $cm^2$ tissue culture flasks held in an upright position.

After 5 days incubation (37° C., 8% $CO_2$ in air), the cells were recovered, washed, and counted for use as effector cells for the CTL assay. Target cells were EG.7 or EL-4 cells (negative controls for non-specific killing). The target cells (ca $10^7$) were labelled with 100 μCi of $^{51}Cr$ in 50 μl of RPM1 medium containing 8% FBS medium, for 45 min. Washed target cells ($2.5 \times 10^4$ cells/well) at various ratios of effector to target cells (as indicated) were co-cultured (4 h) in 96-well, round bottom tissue culture plates. The culture supernatants were collected and the released radioactivity in 70 μl aliquots for gamma counter or in 50 μl aliquots for beta counter, was measured after adding to 150 μl Optiphase Supermix$^R$ scintillant (PerkinElmer LAS Canada, Inc., Woodbridge, Ontario, Canada). Percent specific cell lysis was calculated as 100× [(cpm experimental−cpm spontaneous)/cpm maximum−cpm spontaneous)].

Example 18

Elicitation of Anti-OVA IgA Antibody Responses by AMVAD, Archaeosome, and Cholera Toxin (CT) Vaccines Administered i.n.

Ovalbumin (OVA) was used as a model antigen to evaluate the efficacy of AMVAD vaccines to elicit immunity. The OVA/Ms archaeosome and OVA/Ms AMVAD vaccines were prepared as described in Examples 2 and 3, respectively. The loading of OVA in OVA/Ms archaeosomes and OVA/Ms AMVAD was 40.2 and 52.0 μg OVA/mg lipid, respectively. A vaccine consisting of OVA in saline (no adjuvant control) and one consisting of empty Ms AMVAD in saline (no OVA) were also included for comparative purposes. Groups of Balb/c mice (6-8 week old, n=5) were i.n.-immunized at 0, 7 and 21 days (10 μg OVA/immunization), samples collected at 29 d, and antibody subtypes were determined as described in Example 17, using sample dilutions as indicated in Example 17.

Figure 4B:
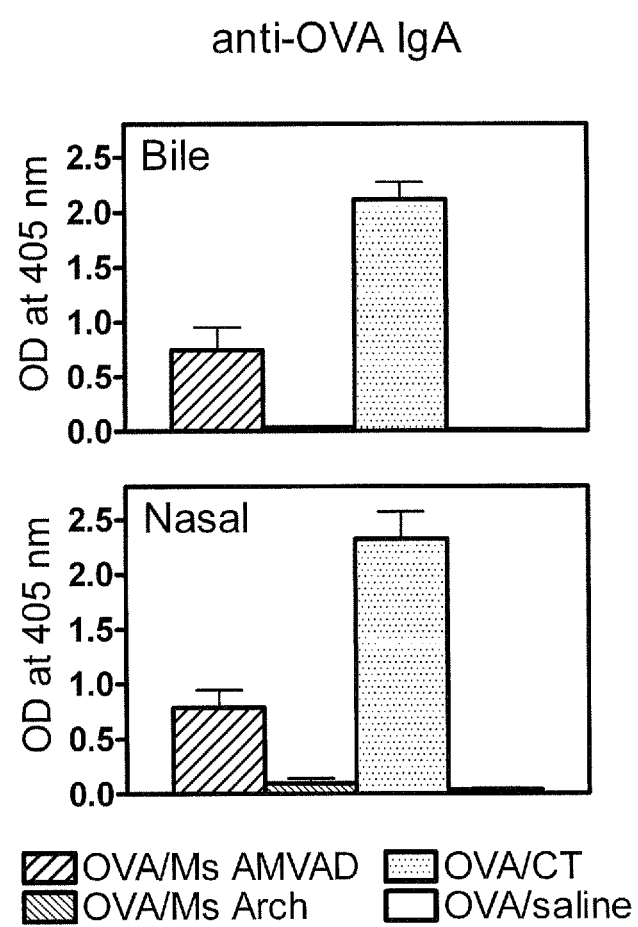
FIG. 4B shows the anti-OVA IgA antibody titres in bile and nasal lavage at 28 d in Balb/c mice that were vaccinated i.n. at 0, 7 and 21 d with 10 μg OVA formulated with Ms AMVAD, Ms archaeosomes (Ms arch), cholera toxin (CT) or saline (antigen alone, no adjuvant group). The specific antibody titres (mean OD±SD) elicited with CT and AMVAD vaccines are strong, compared with little to no responses seen with the archaeosome or saline groups.

The results demonstrate that both, CT and AMVAD vaccines elicit strong OVA-specific fecal, vaginal and serum IgA antibody responses (FIG. 4A). Archaeosome vaccine elicited negligible OVA-specific IgA responses. In a separate experiment, anti-OVA IgA responses in nasal lavage and bile samples collected at 28 d, from mice that were identically immunized as in FIG. 4A, showed that CT and AMVAD vaccines elicited robust responses (FIG. 4B). However, the IgA responses in the archaeosome vaccine mice group were not measurable, and were similar to that obtained with the OVA/saline vaccine (FIG. 4B). Data from groups of mice immunized with OVA admixed with CT (CT) are included as a positive control since CT is known as a strong mucosal adjuvant. These results show that unlike the archaeosome vaccine administered i.n., the AMVAD vaccine elicits robust mucosal immunity as indicated by the observed IgA responses.

In another experiment, there were no detectable anti-OVA mucosal immune responses in groups of mice similarly immunized i.n. (at 0, 7, 21 d, and samples collected at 28 d for assays) with either empty Ms AMVAD vaccine (i.e., AMVAD vaccine with no OVA) or with vaccine comprising pre-formed empty Ms AMVAD preparation that was admixed with OVA (at similar lipid:antigen ratio as in OVA/Ms AMVAD prepared by the standard protocol) just prior to immunization (10 μg OVA/immunization). This indicates that the antigen has to be physically associated with the AMVAD structure for the elicitation of antigen-specific mucosal immune responses.

Example 19

Elicitation of OVA-Specific Antibody Responses by Various OVA/AMVAD Vaccines

Various OVA/AMVAD vaccines, prepared from either the total polar lipids extract, the total lipids extract (total polar lipids plus the neutral lipids) or a single polar lipid extracted in a biologically pure form, from different species of *Archaea*, were prepared as described in Example 3. Ovalbumin/cohleate vaccine (OVA/coch), described in prior art, were prepared from the ester lipid 1,2-Dioleoyl-sn-Glycero-3-[Phospho-L-Serine] and cholesterol as described in Example 16.

Vaccine consisting of OVA in saline (OVA/saline) was included as a control. The loading of OVA in AMVAD vaccines prepared from the total polar lipids of *M. smithii* (OVA/Ms AMVAD), *H. salinarum* (OVA/Hs AMVAD), *T. acidophilum* (OVA/Ta AMVAD) was 52.0, 46.9 and 87.7 μg/mg lipid, respectively. The OVA loading in vaccines prepared from the total lipid extract from *M. smithii* (OVA/Ms TLE AMVAD) was 34.1 μg/mg lipid. The loading of OVA in DOPS cochleates (OVA/coch) was 37.7 μg/mg of DOPS plus cholesterol. Groups of Balb/c mice (6-8 week old, n=5) were i.n.-immunized at 0, 7 and 21 d (10 μg OVA/immunization), and all groups were given an antigen alone boost (20 μg in saline) at 225 d via the same route of administration as the primary immunization for the specific group, as described in Example 17. One group of mice was similarly immunized s.c. with OVA/Ms AMVAD (10 μg OVA/immunization) and s.c. boosted with OVA alone at 225 d. Samples were collected at 28 d, 91 d, 224 d and 232 d, and antibody subtypes were determined as described in Example 17, using sample dilutions described in Example 17, except that the vaginal wash samples were diluted 1:10 for the ELISA assays.

Figure 5A:
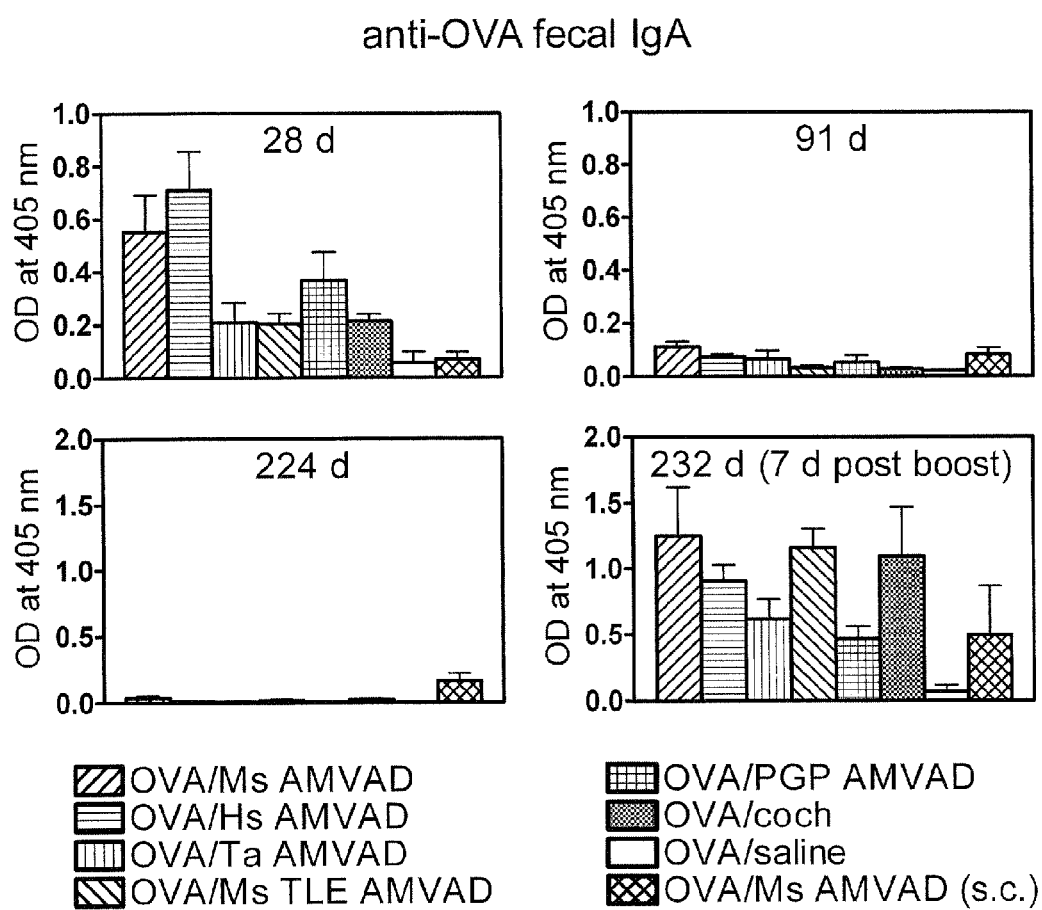
FIG. 5A shows elicitation of anti-OVA fecal IgA titres (mean OD±SD) at 28 to 224 d after i.n. immunization (0, 7, 21 d) of groups of Balb/c mice with OVA (10 μg/immunization) formulated with Ms AMVAD, Hs AMVAD, Ta AMVAD, TLE Ms AMVAD, PGP AMVAD, DOPS cochleates (coch) or saline.
Figure 5B:
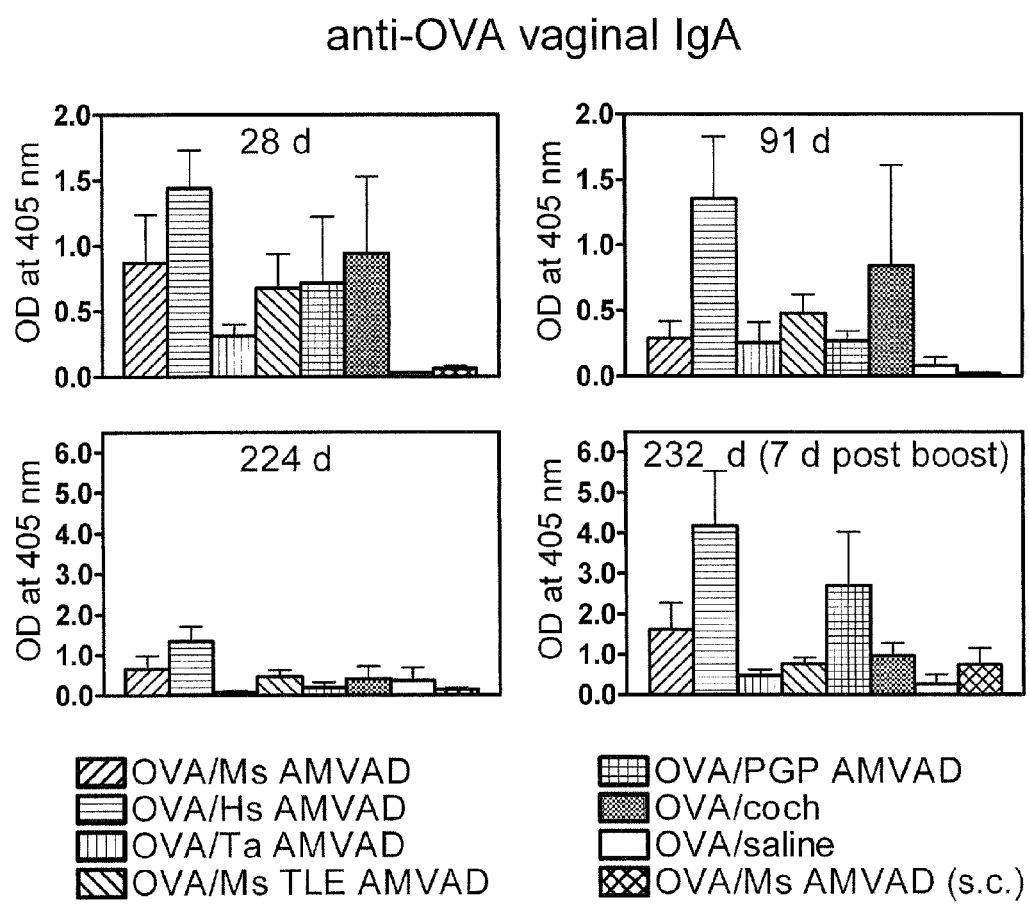
FIG. 5B shows elicitation of anti-OVA vaginal IgA titres (mean OD±SD) at 28 to 224 d after i.n. immunization (0, 7, 21 d) of groups of Balb/c mice with OVA (10 μg/immunization) formulated with Ms AMVAD, Hs AMVAD, Ta AMVAD, TLE Ms AMVAD, PGP AMVAD, DOPS cochleates (coch) or saline.
Figure 5C:
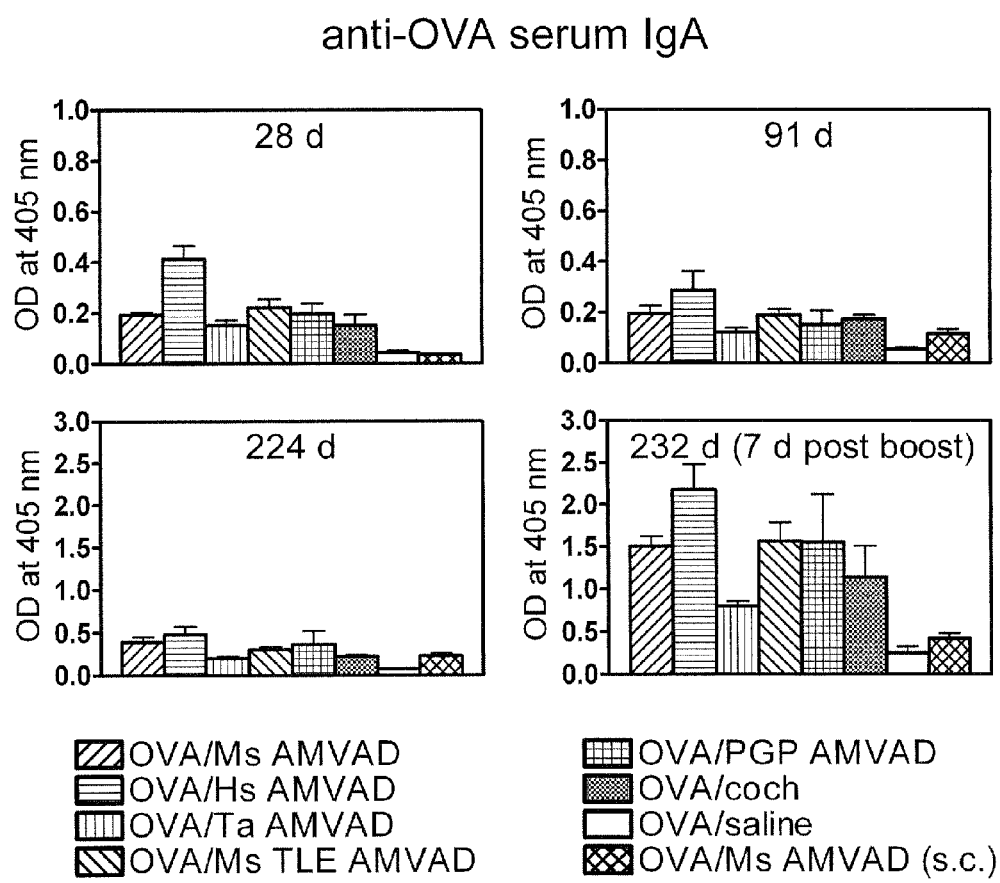
FIG. 5C shows elicitation of anti-OVA serum IgA titres (mean OD±SD) at 28 to 224 d after i.n. immunization (0, 7, 21 d) of groups of Balb/c mice with OVA (10 μg/immunization) formulated with Ms AMVAD, Hs AMVAD, Ta AMVAD, TLE Ms AMVAD, PGP AMVAD, DOPS cochleates (coch) or saline.
Figure 5D:
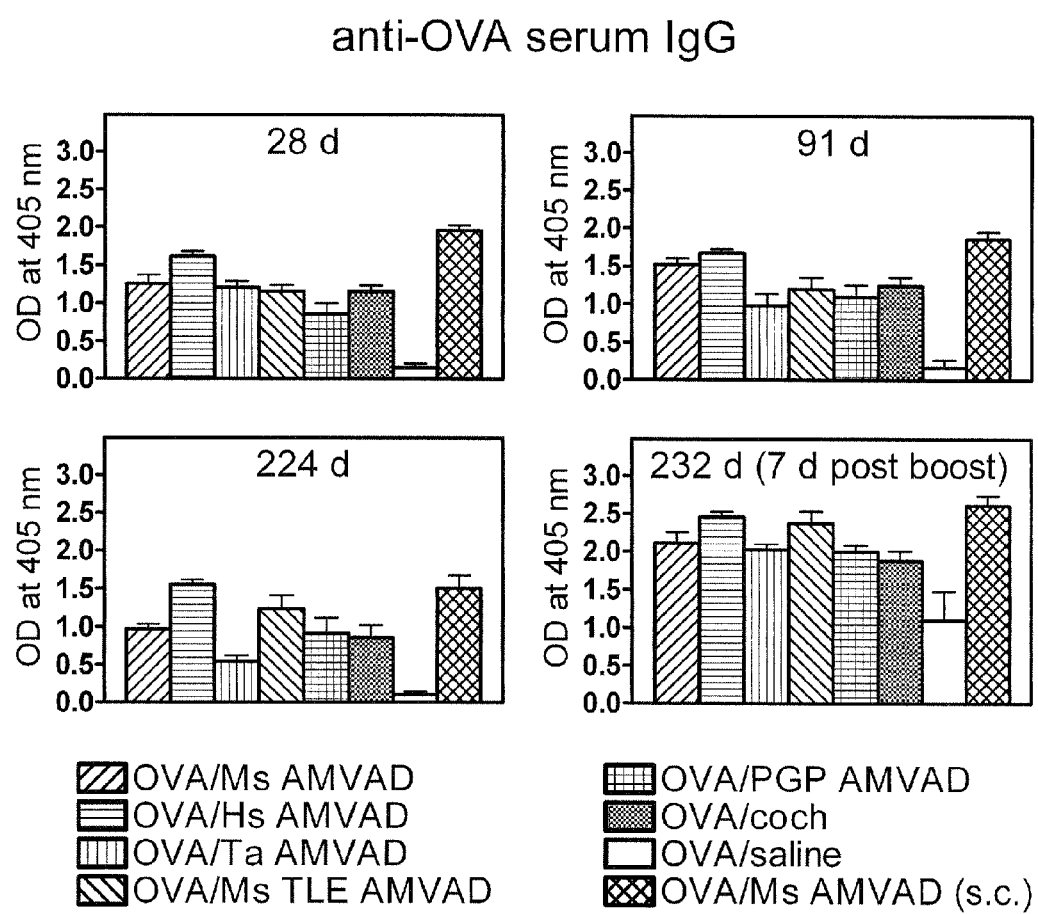
FIG. 5D shows elicitation of anti-OVA serum IgG titres (mean OD±SD) at 28 to 224 d after i.n. immunization (0, 7, 21 d) of groups of Balb/c mice with OVA (10 μg/immunization) formulated with Ms AMVAD, Hs AMVAD, Ta AMVAD, TLE Ms AMVAD, PGP AMVAD, DOPS cochleates (coch) or saline.
Figure 5E:
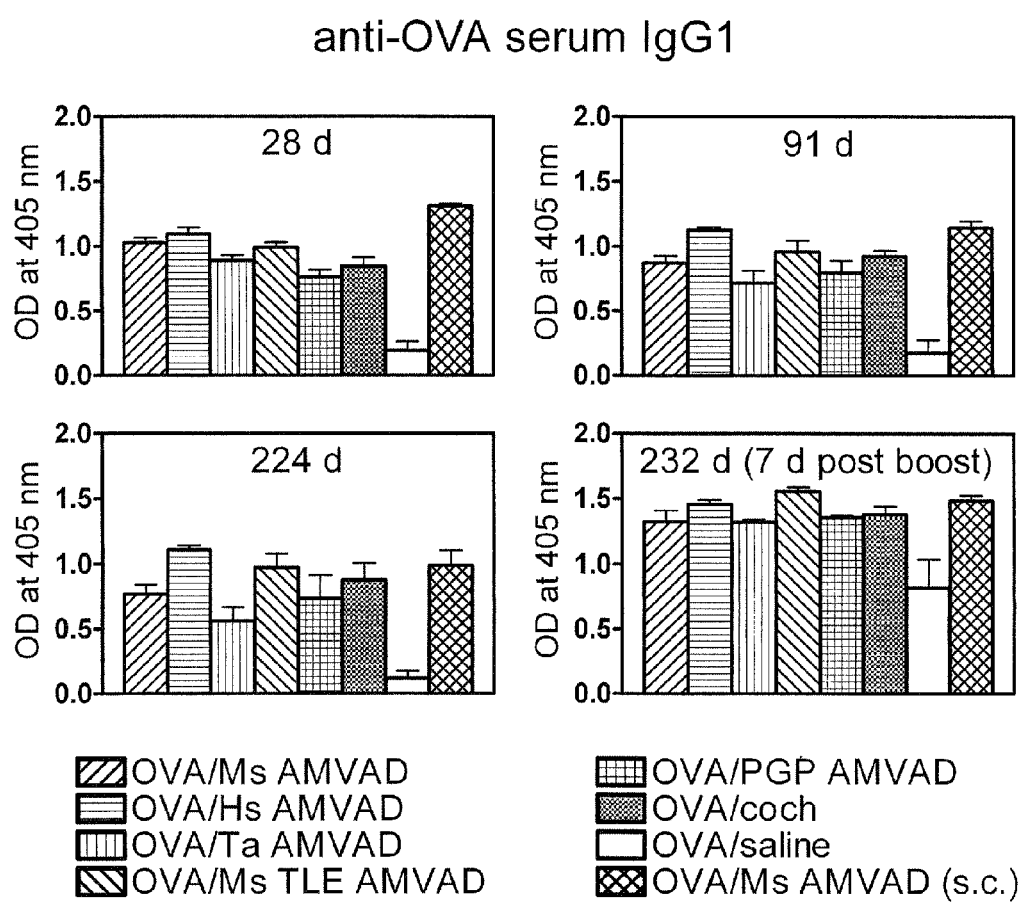
FIG. 5E shows elicitation of anti-OVA serum IgG1 titres (mean OD±SD) at 28 to 224 d after i.n. immunization (0, 7, 21 d) of groups of Balb/c mice with OVA (10 μg/immunization) formulated with Ms AMVAD, Hs AMVAD, Ta AMVAD, TLE Ms AMVAD, PGP AMVAD, DOPS cochleates (coch) or saline.
Figure 5F:
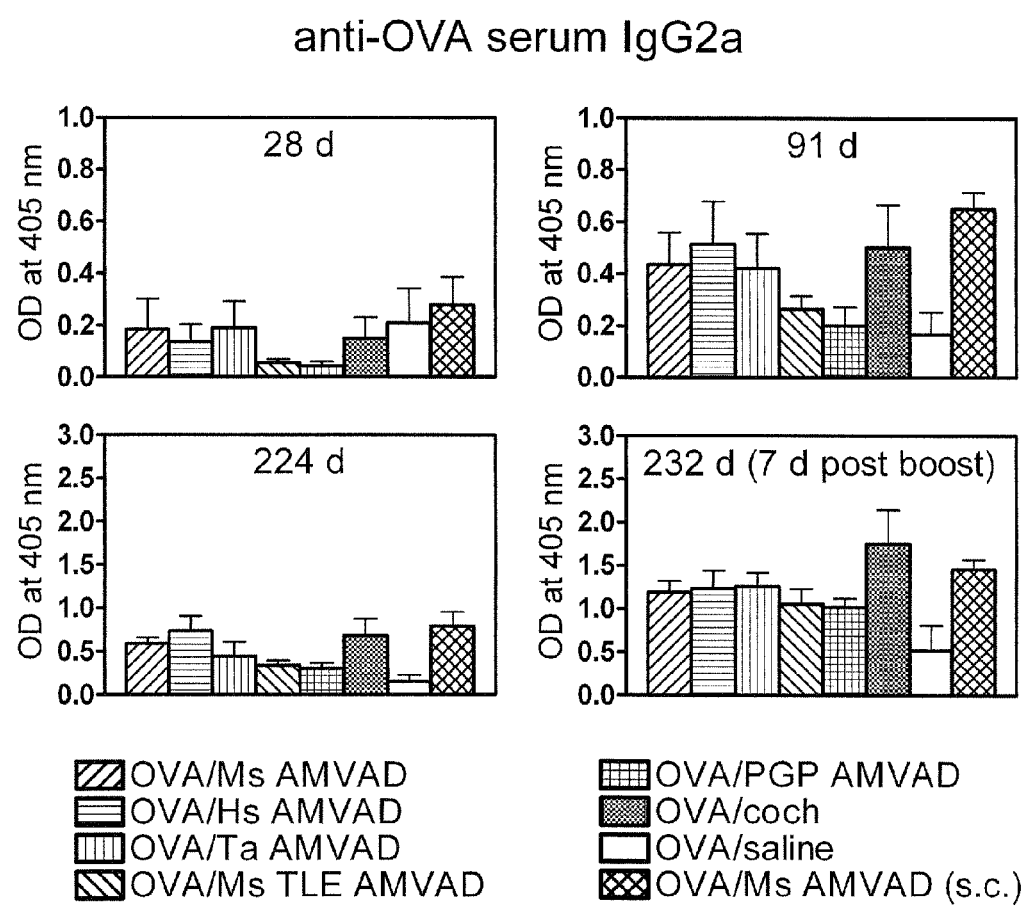
FIG. 5F shows elicitation of anti-OVA serum IgG2a titres (mean OD±SD) at 28 to 224 d after i.n. immunization (0, 7, 21 d) of groups of Balb/c mice with OVA (10 μg/immunization) formulated with Ms AMVAD, Hs AMVAD, Ta AMVAD, TLE Ms AMVAD, PGP AMVAD, DOPS cochleates (coch) or saline. Also shown (bottom right panel in FIG. 5A-5F) is the elicitation of strong memory responses at 232 d in groups immunized with AMVAD vaccines, after an antigen alone (in saline) boost (administered via the same route as original immunization) given at 225 d. The anti-OVA IgA titres in bile and nasal lavage at 232 d (7 d post boost) are shown in FIG. 5G.

The results show that all OVA/AMVAD vaccines administered by i.n. route elicit strong anti-OVA IgA responses at 28 d, as measured in the feces, vaginal wash and sera (FIGS. 5A-5C). Whereas the fecal IgA responses declined between 28 and 91 d, vaginal and serum IgA responses were sustained over the 28-224 d period. It is also seen that upon OVA alone boost at 225 d, there are strong IgA memory boost responses in all groups of mice i.n. immunized with the OVA/AMVAD vaccines, including the fecal IgA responses, as seen by the increase in the titres at 232 d compared with the pre-boost values observed at 224 d. The IgA responses in OVA/saline i.n. immunized groups were negligible to not measurable. In the case of the group of mice given OVA/Ms AMVAD vaccine systemically via the s.c route, there is little to no primary mucosal IgA response. All AMVAD vaccinated groups elicited robust and well sustained serum IgG, IgG1 and IgG2a responses, including a strong memory boost upon OVA/saline booster immunization at 224 d (FIGS. 5D-5F).

Figure 5G:
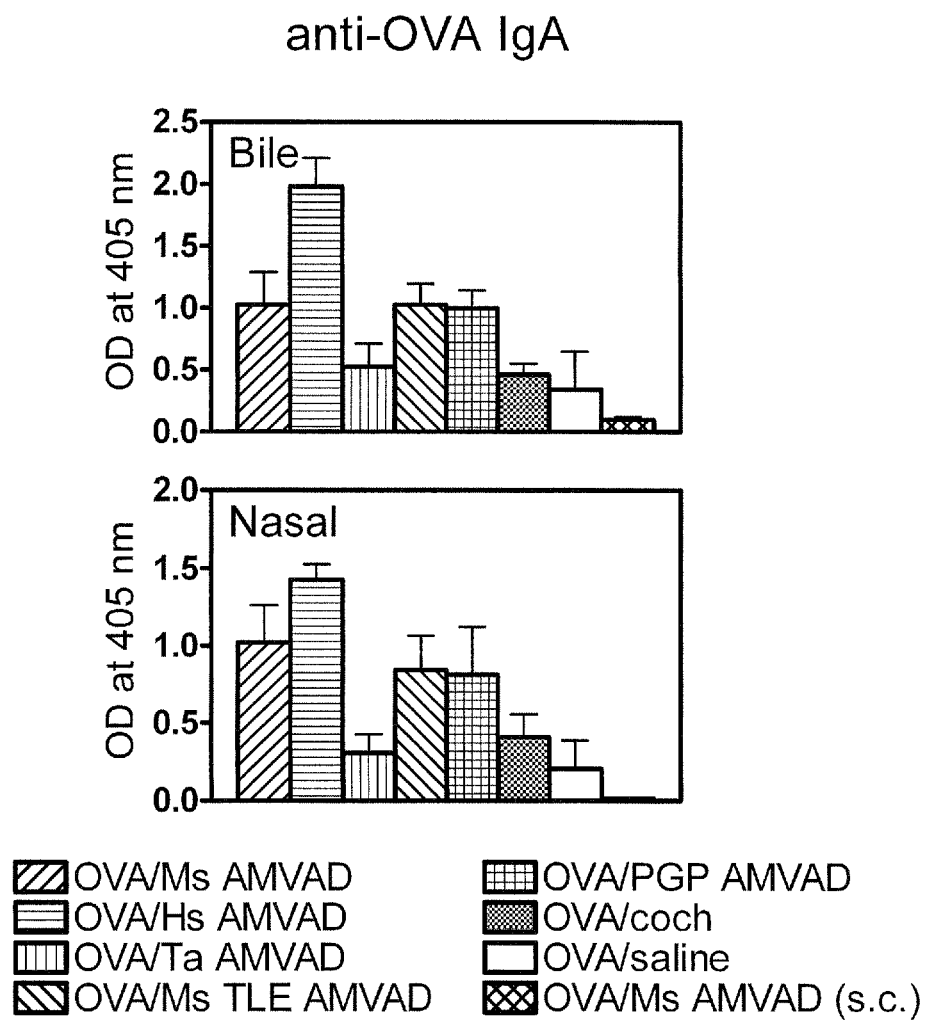

The bile and nasal IgA responses in the 232 d samples (7 d post antigen alone boost at 225 d) indicated strong responses in all of the i.n. vaccinated OVA/AMVAD groups, and these responses were generally substantially greater than those observed in the DOPS/coch group (FIG. 5G). The primary fecal IgA responses at 28 d, in mouse groups i.n. vaccinated with OVA/AMVAD vaccines were also generally higher than that obtained in the DOPS/coch group (FIG. 5A). Data from mice immunized with DOPS/coch vaccine are given for comparative purposes.

These results demonstrate that different types of OVA/AMVAD vaccines (prepared form a wide variety of archaeal polar lipids) when administered via i.n. route, elicit strong and generally well sustained antigen-specific mucosal immunity, and this immunity is boostable (memory response) by antigen alone booster vaccination. The results also show that OVA/AMVAD vaccines administered i.n. also elicit strong systemic immune responses (serum IgG, IgG1, IgG2a). However, although s.c. immunization with OVA/Ms AMVAD vaccine elicits strong systemic immune responses, it elicits very little or no mucosal immunity (i.e., fecal, vaginal, serum, nasal and bile IgA responses).

Example 20

Elicitation of Anti-BSA Antibody Responses by AMVAD Vaccines Administered i.n.

Figure 6A:
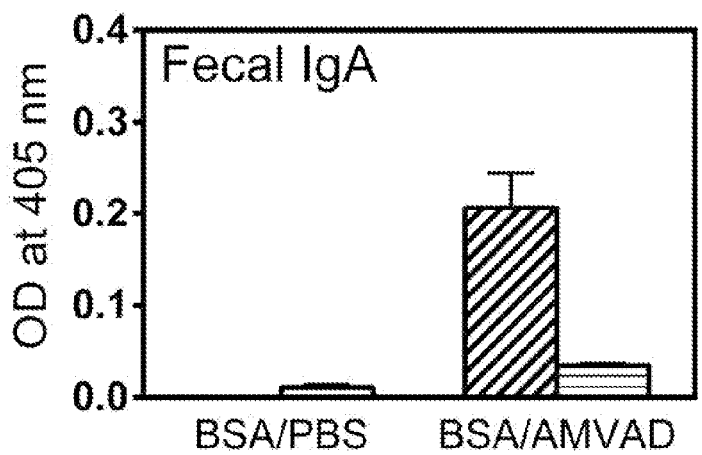
FIGS. 6A-6C show elicitation of antigen specific antibody responses in Balb/c mice upon i.n. administration of AMVAD vaccines containing another model antigen, BSA.
Figure 6B:
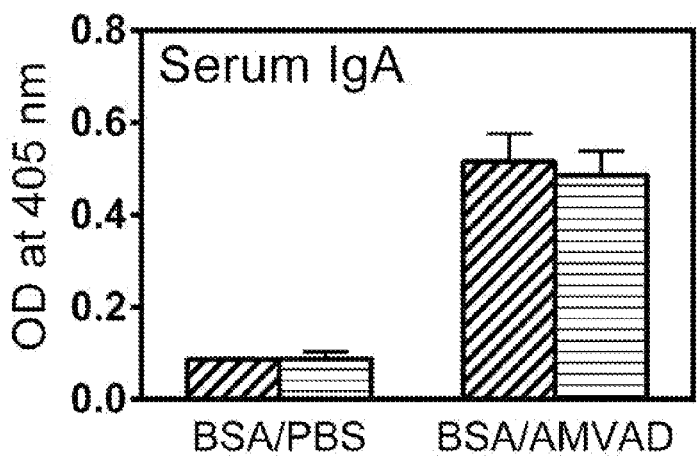
Figure 6C:
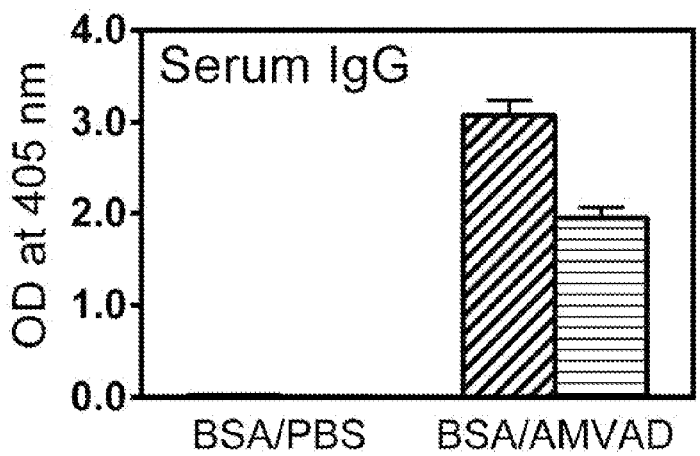

The efficacy of AMVAD vaccines to elicit mucosal immunity was also evaluated using bovine serum albumin (BSA) as another model antigen. The BSA/Ms AMVAD vaccine formulation was prepared as described in Example 3, except that the AMVAD formulation was re-suspended in PBS (pH 7.2 phosphate buffered saline described in Example 17) supplemented with 15 mM $CaCl_2$ instead of in saline. The loading of BSA was 32.1 μg/mg lipid. Balb/c mice were immunized i.n. 0, 7 and 21 d (10 μg BSA/immunization), serum and fecal samples were collected at 28 and 204 d, and antibody subtypes determined as described in Example 17. The results showed that similar to OVA as the antigen, strong anti-BSA fecal IgA, serum IgA and serum IgG responses were obtained with BSA/Ms AMVAD vaccine (FIG. 6A-6C). The BSA/PBS (no adjuvant) vaccine elicited little to no immune responses.

Example 21

Elicitation of Mucosal and Systemic Immunity Upon i.n. Immunization with OVA Ms AMVAD Formulations Prepared by Simplified Protocols The efficacy of OVA/Ms AMVAD vaccine prepared by the standard protocol in Example 3 was compared with two formulations prepared by protocols given in Examples 5 and 6. The two latter protocols were simplified to avoid both, the centrifugation steps and the final determination of the actual OVA loading in the AMVAD formulation. The OVA/Ms AMVAD-ANW formulation prepared in Example 5 by admixing of empty Ms archaeosomes with OVA and then converting these to AMVAD formulation by addition of $CaCl_2$, was used as one of the two simplified methods to make Ms AMVAD formulations.

In this protocol, the starting ratio of lipid:OVA (w/w) at the time of admixing empty archaeosomes with OVA was selected to be 22.2:1 (instead of 2:1 in the standard protocol at the time of hydration of lipids to make OVA encapsulated archaeosomes in Example 3), there were no centrifugation steps, the AMVAD formulation was not washed to remove free-OVA in the formulation. This protocol essentially also eliminated the need to prior encapsulate the OVA into archaeosomes before conversion into OVA/AMVAD formulation. The altered starting ratio assured that the total OVA in the finished formulation (45 μg/mg lipid) would be similar to that obtained (45 μg/mg lipid) in the OVA/Ms AMVAD formulation prepared by the standard protocol. However, in the AMVAD formulation prepared by the standard protocol where there was no free OVA in solution in the formulation (all OVA was associated with AMVAD), in the OVA/Ms AMVAD-ANW formulation about 79% of the total OVA in the formulation was free (or un-associated) OVA in solution, with the remainder being AMVAD associated.

The second simplified protocol for preparing OVA/Ms AMVAD formulation was as described in Example 6, which is exactly the same as the standard protocol in Example 3 except that the starting ratio (w/w) of lipid:OVA was selected to be 22.2:1 at the time of hydration of the lipids to make archaeosomes with encapsulated OVA, and that the subsequent AMVAD formulation (OVA/Ms AMVAD-NW) obtained by $CaCl_2$ addition was not washed to remove free OVA. In this protocol, the selected starting ratio of lipid:OVA at the time of hydration of lipids to obtain archaeosomes assured that the OVA in the finished AMVAD formulation (45 μg/mg lipid) would be similar to that obtained (45 μg/mg lipid) in the OVA/Ms AMVAD formulation prepared by the standard protocol. However, in the AMVAD formulation prepared by the standard protocol where there was no free OVA in solution in the formulation (all OVA was associated with AMVAD), in the OVA/Ms AMVAD-NW formulation, about 81% of the total OVA in the formulation was free (or un-associated) OVA in solution, with the remainder being AMVAD associated.

Figure 7A:
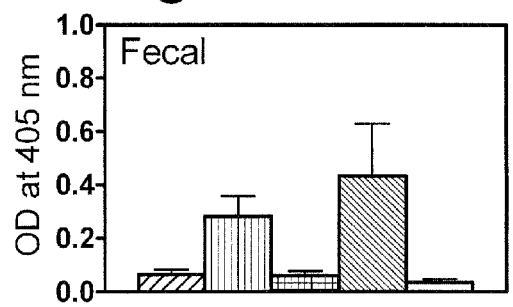
FIG. 7A shows the comparative anti-OVA fecal IgA titres (mean OD±SD) at 28 d, upon i.n. immunization of Balb/c mice with OVA Ms AMVAD formulations (10 μg OVA/immunization at 0, 7, 21 d) prepared by different protocols.
Figure 7B:
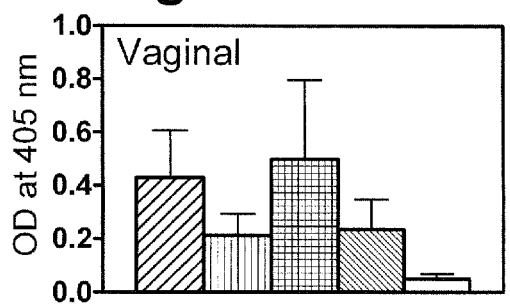
FIG. 7B shows the comparative anti-OVA vaginal IgA titres (mean OD±SD) at 28 d, upon i.n. immunization of Balb/c mice with OVA Ms AMVAD formulations (10 μg OVA/immunization at 0, 7, 21 d) prepared by different protocols.
Figure 7C:
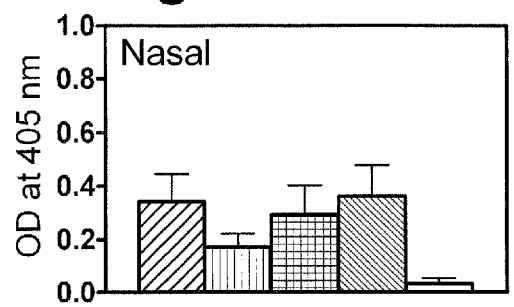
FIG. 7C shows the comparative anti-OVA nasal IgA titres (mean OD±SD) at 28 d, upon i.n. immunization of Balb/c mice with OVA Ms AMVAD formulations (10 μg OVA/immunization at 0, 7, 21 d) prepared by different protocols.
Figure 7D:
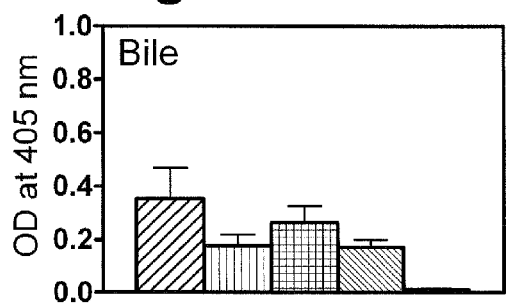
FIG. 7D shows the comparative anti-OVA bile IgA titres (mean OD±SD) at 28 d, upon i.n. immunization of Balb/c mice with OVA Ms AMVAD formulations (10 μg OVA/immunization at 0, 7, 21 d) prepared by different protocols.
Figure 7E:
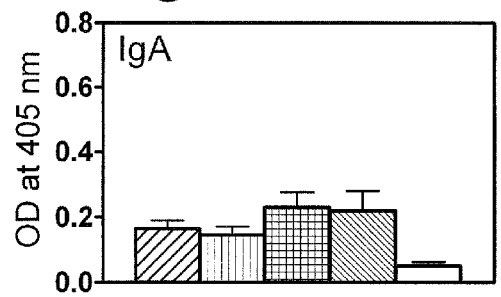
FIG. 7E shows the comparative anti-OVA serum IgA titres (mean OD±SD) at 28 d, upon i.n. immunization of Balb/c mice with OVA Ms AMVAD formulations (10 μg OVA/immunization at 0, 7, 21 d) prepared by different protocols.
Figure 7F:
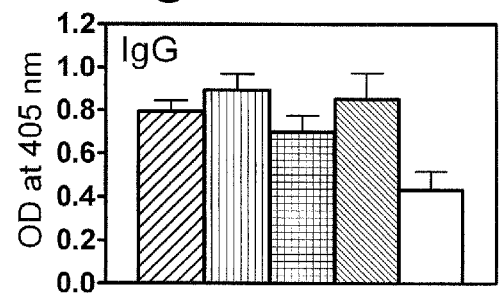
FIG. 7F shows the comparative anti-OVA serum IgG titres (mean OD±SD) at 28 d, upon i.n. immunization of Balb/c mice with OVA Ms AMVAD formulations (10 μg OVA/immunization at 0, 7, 21 d) prepared by different protocols.
Figure 7G:
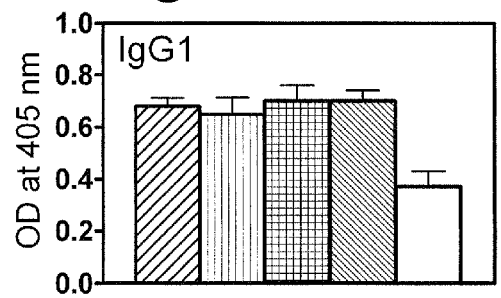
FIG. 7G shows the comparative anti-OVA serum IgG1 titres (mean OD±SD) at 28 d, upon i.n. immunization of Balb/c mice with OVA Ms AMVAD formulations (10 μg OVA/immunization at 0, 7, 21 d) prepared by different protocols.
Figure 7H:
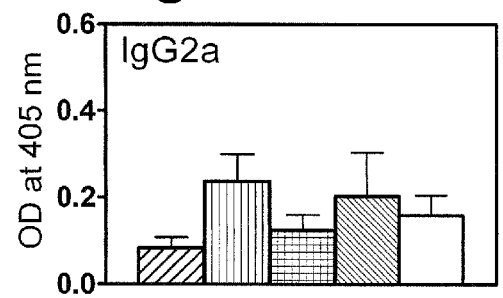
FIG. 7H shows the comparative anti-OVA serum IgG2a titres (mean OD±SD) at 28 d, upon i.n. immunization of Balb/c mice with OVA Ms AMVAD formulations (10 μg OVA/immunization at 0, 7, 21 d) prepared by different protocols. The OVA AMVAD formulations used were OVA/Ms AMVAD prepared by the standard protocol as described in Example 3, OVA/Ms AMVAD-NW prepared as described in Example 6, OVA/Ms AMVAD-ANW prepared as described in Example 5, or OVA$^-$/Ms AMVAD prepared as described in Example 4. A control group was similarly immunized with OVA in saline supplemented 15 mM $CaCl_2$ (OVA/$CaCl_2$, no adjuvant group). The results show that the immune responses elicited by the Ms AMVAD vaccines prepared by the various methods were comparable to the responses obtained with the formulation prepared by the standard protocol.

Groups of Balb/c mice (6-8 week old, n=5) were i.n.-immunized at 0, 7 and 21 d (10 μg OVA/immunization), samples collected at 28 d, and antibody subtypes were determined as described in Example 17. The results show that the fecal, vaginal, nasal, bile (FIGS. 7A-7D) and serum (FIG. 7E) anti-OVA IgA antibody titres in the groups of mice immunized with the OVA/Ms AMVAD vaccine prepared by the standard protocol were similar to the titres obtained in the groups of mice vaccinated with either of the two formulations (OVA/Ms AMVAD-ANW or OVA/Ms AMVAD-NW) prepared by the simplified protocols (FIG. 7A-7E). The group vaccinated with OVA in saline supplemented with 15 mM $CaCl_2$ (OVA/$CaCl_2$) elicited little or no measurable IgA antibody responses. It is also seen that the serum IgG, IgG1 and IgG2a anti-OVA antibody responses in the groups of mice immunized with Ms AMVAD prepared by the standard and the two simplified protocols are comparable (FIGS. 7F-7H).

It is also seen in FIGS. 7A-7H that in the group of mice which was similarly i.n. immunized with OVA$^-$/Ms AMVAD formulation prepared in Example 4, the elicitation of anti-OVA IgA, IgG, IgG1 and IgG2a antibody titres were comparable to those obtained in the group immunized with OVA/Ms AMVAD prepared by the standard protocol. Since the OVA$^-$/Ms AMVAD formulation was prepared exactly as per the standard protocol except that the un-encapsulated OVA was removed from the archaeosome preparation before adding $CaCl_2$ to convert the archaeosomes to AMVAD structures, these results show that the elicitation of mucosal and systemic immunity is not affected whether or not the un-encapsulated OVA in the archaeosome formulation is removed prior to conversion to AMVAD formulation.

Results in this Example demonstrate that protocols for AMVAD vaccine formulation preparation can be simplified for practical purposes, without adversely affecting the efficacy in the elicitation of mucosal and systemic immunity. Additionally, the possible precipitation of free OVA by $CaCl_2$ is not a factor in the elicitation of mucosal immunity by i.n. administration of OVA/AMVAD formulations prepared as described herein by various different protocols. The latter conclusion is further supported by the observation that i.n. administration of OVA/$CaCl_2$ vaccine failed to elicit anti-OVA mucosal immune responses (FIGS. 7A-7D).

Example 22

Elicitation of Mucosal and Systemic Immunity Upon i.n. Immunization with OVA/Hs AMVAD Formulations Prepared by Simplified Protocols The efficacy of OVA/Hs AMVAD vaccine prepared by the standard protocol in Example 3, was compared with a formulation prepared by alternate, simpler protocol given in Example 5. The latter protocol was simplified to avoid both, the centrifugation steps and the determination of the actual OVA loading in the final AMVAD formulation. The OVA/Hs AMVAD-ANW formulation prepared in Example 5 by admixing of empty Hs archaeosomes with OVA and then converting these to AMVAD formulation by addition of $CaCl_2$, was used in the current Example.

In this protocol, the starting ratio of lipid:OVA (w/w) at the time of admixing empty archaeosomes with OVA was selected to be 32.9:1 (instead of 2:1 in the standard protocol at the time of hydration of lipids to make OVA encapsulated archaeosomes in Example 3), there were no centrifugation steps, and the final AMVAD formulation was not washed to remove free-OVA in the formulation. This protocol essentially also eliminated the need to encapsulate the OVA into archaeosomes prior to their conversion into OVA/AMVAD formulation. The altered starting ratio of lipid:OVA assured that the total OVA in the finished formulation (30.5 µg/mg lipid) would be similar to that obtained (30.4 µg/mg lipid) in the OVA/Hs AMVAD formulation prepared by the standard protocol. However, in contrast to the AMVAD formulation prepared by the standard protocol where there was no free OVA in solution in the formulation (all OVA was associated with AMVAD), in the OVA/Hs AMVAD-ANW formulation about 66% of the OVA in the formulation was free (or un-associated) OVA in solution, with the remainder being AMVAD associated.

Figure 8A:
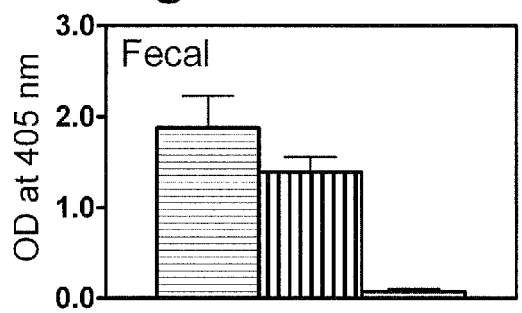
FIG. 8A shows the comparative anti-OVA fecal IgA titres (mean OD±SD) at 28 d, upon i.n. immunization of Balb/c mice with OVA Hs AMVAD formulations (10 μg OVA/immunization at 0, 7 21 d) prepared by different protocols.
Figure 8B:
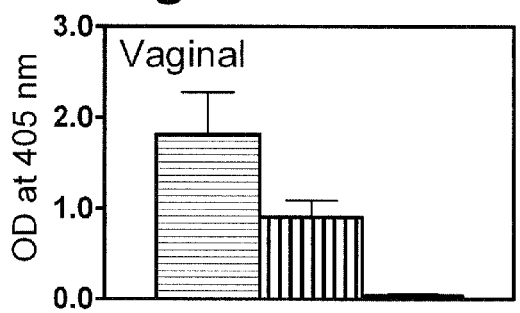
FIG. 8B shows the comparative anti-OVA vaginal IgA titres (mean OD±SD) at 28 d, upon i.n. immunization of Balb/c mice with OVA Hs AMVAD formulations (10 μg OVA/immunization at 0, 7 21 d) prepared by different protocols.
Figure 8C:
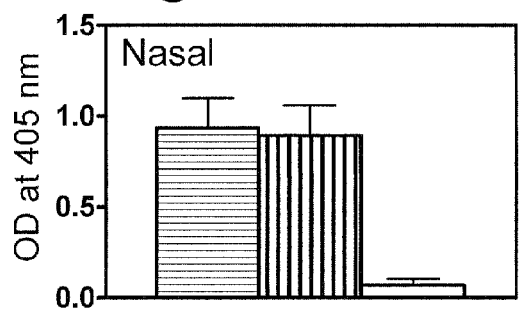
FIG. 8C shows the comparative anti-OVA nasal IgA titres (mean OD±SD) at 28 d, upon i.n. immunization of Balb/c mice with OVA Hs AMVAD formulations (10 μg OVA/immunization at 0, 7 21 d) prepared by different protocols.
Figure 8D:
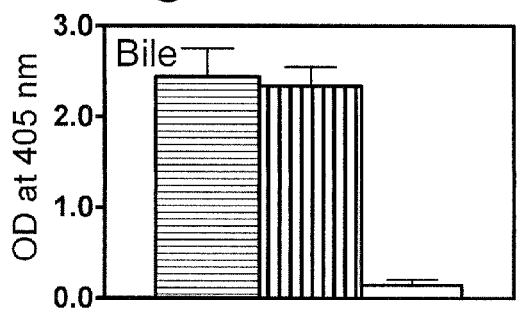
FIG. 8D shows the comparative anti-OVA bile IgA titres (mean OD±SD) at 28 d, upon i.n. immunization of Balb/c mice with OVA Hs AMVAD formulations (10 μg OVA/immunization at 0, 7 21 d) prepared by different protocols.
Figure 8E:
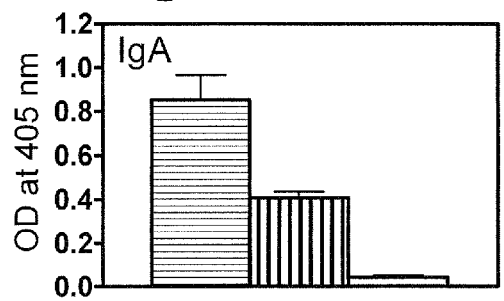
FIG. 8E shows the comparative anti-OVA serum IgA titres (mean OD±SD) at 28 d, upon i.n. immunization of Balb/c mice with OVA Hs AMVAD formulations (10 μg OVA/immunization at 0, 7 21 d) prepared by different protocols.
Figure 8F:
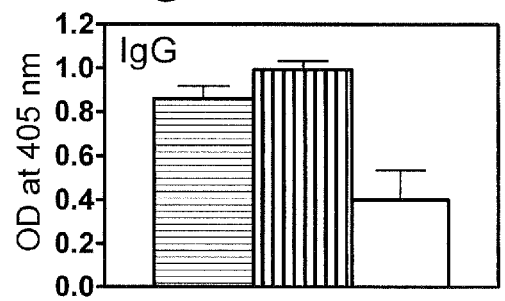
FIG. 8F shows the comparative anti-OVA serum IgG titres (mean OD±SD) at 28 d, upon i.n. immunization of Balb/c mice with OVA Hs AMVAD formulations (10 μg OVA/immunization at 0, 7 21 d) prepared by different protocols.
Figure 8G:
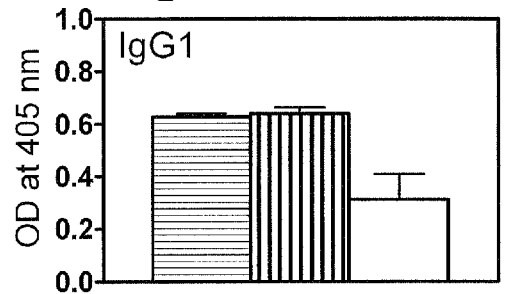
FIG. 8G shows the comparative anti-OVA serum IgG1 titres (mean OD±SD) at 28 d, upon i.n. immunization of Balb/c mice with OVA Hs AMVAD formulations (10 μg OVA/immunization at 0, 7 21 d) prepared by different protocols.
Figure 8H:
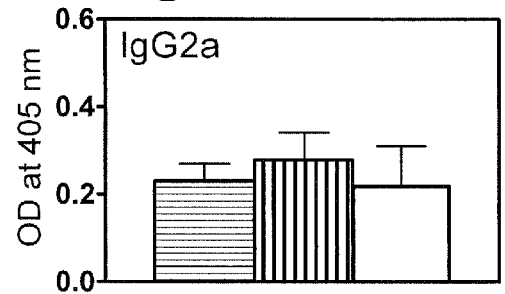
FIG. 8H shows the comparative anti-OVA serum IgG2a titres (mean OD±SD) at 28 d, upon i.n. immunization of Balb/c mice with OVA Hs AMVAD formulations (10 μg OVA/immunization at 0, 7 21 d) prepared by different protocols. The OVA AMVAD formulations used were OVA/Hs AMVAD prepared by the standard protocol as described in Example 3 and OVA/Hs AMVAD-ANW prepared as described in Example 5. A control group was similarly immunized with OVA in saline supplemented 15 mM $CaCl_2$ (OVA/$CaCl_2$, no adjuvant group). The results show that the immune responses elicited by the Hs AMVAD vaccines prepared by the various methods were comparable to the responses obtained with the formulation prepared by the standard protocol.

Groups of Balb/c mice (6-8 week old, n=5) were immunized i.n. at 0, 7 and 21 days (10 µg OVA/immunization), samples collected at 28 d, and antibody subtypes were determined as described in Example 17. The results show that the fecal, vaginal, nasal, bile (FIGS. 8A-8D) and serum (FIG. 8E) anti-OVA IgA antibody titres in the group of mice immunized with OVA/Hs AMVAD-ANW prepared by the simplified protocol were comparable with the titres obtained in mice immunized with OVA/Hs AMVAD prepared by the standard protocol. The group vaccinated with OVA in saline supplemented with 15 mM $CaCl_2$ (OVA/$CaCl_2$) elicited little or no measurable anti-OVA IgA antibody responses FIG. 8A-8E). It is also seen that the serum IgG, IgG1 and IgG2a anti-OVA antibody responses in the groups of mice immunized with Hs AMVAD prepared by the standard and the simplified protocols are comparable (FIG. 8F-8H).

Results in this Example demonstrate that protocols for Hs AMVAD vaccine formulation preparation can also be simplified for practical purposes, without adversely affecting the efficacy in the elicitation of mucosal and systemic immune responses.

Example 23

Elicitation of Cytotoxic T Lymphocyte (CTL) Responses by OVA/AMVAD Vaccines Administered by i.n. and s.c. Routes The elicitation of CTL responses by i.n. administered OVA/Ms AMVAD, OVA/Hs AMVAD, empty Ms AMVAD and empty Hs AMVAD formulations, prepared as described in Example 3, was determined in female, 6-8 week old C57BL/6 mice. In this Example, for all immunizations wherein OVA was present in the vaccine formulation, the immunization dose was 10 µg OVA/immunization. A mouse group i.n. immunized with OVA/saline vaccine was included as one control group, as was a naïve group of mice. An OVA/Ms archaeosome vaccine formulation prepared as described in Example 2, was s.c. administered to one group of mice, for use as a positive control for the determination of the CTL responses. The OVA loading in OVA/Ms AMVAD, OVA/Hs AMVAD and OVA/Ms archaeosomes was 55.1, 33.5, and 46.9 µg/mg lipid. Groups (n=7-10) C57BL/6 mice were immunized i.n. at 0, 7 and 21 d (10 µg OVA/immunization). The OVA/Ms archaeosome vaccine mouse group (n=10) was s.c. immunized at the same OVA dose, at 0 and 21 d. Fecal, vaginal wash and serum samples were collected at 28 d and anti-OVA antibody responses determined, as described in Example 17. The CTL assays were conducted as described in Example 17, using spleen cells collected from sub-groups of mice euthanized at 36-42 d.

Figure 9A:
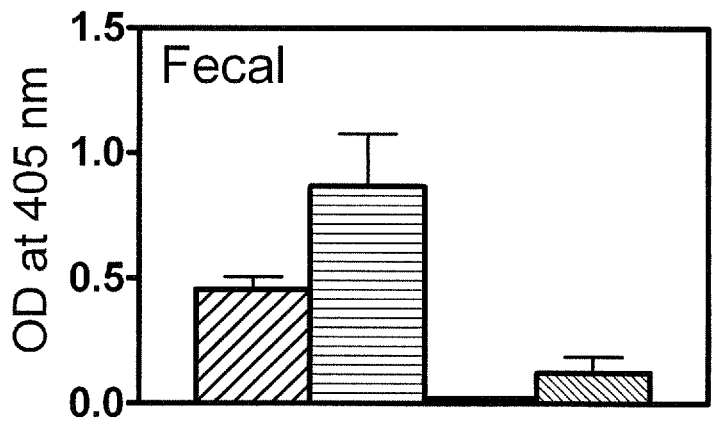
FIG. 9A shows elicitation of anti-OVA fecal IgA titres (mean OD±SD) at 28 d, upon i.n. immunization (0, 7, 21 d) of groups of C57BL/6 mice with OVA (10 μg/immunization) formulated with Ms AMVAD (OVA/Ms AMVAD) or Hs AMVAD (OVA/Hs AMVAD) vaccines prepared as described in Example 3.
Figure 9B:
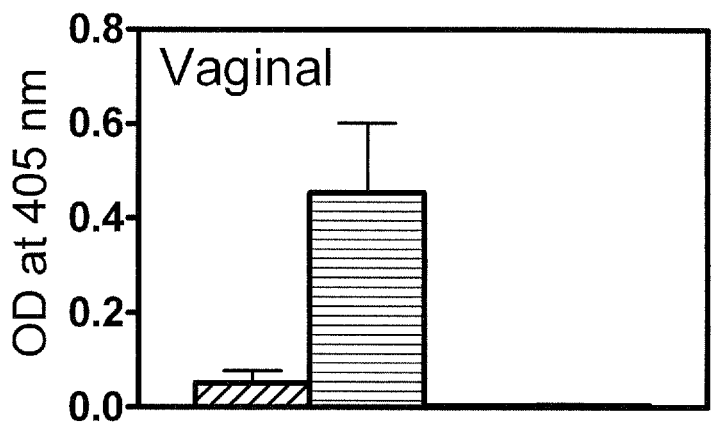
FIG. 9B shows elicitation of anti-OVA vaginal IgA titres (mean OD±SD) at 28 d, upon i.n. immunization (0, 7, 21 d) of groups of C57BL/6 mice with OVA (10 μg/immunization) formulated with Ms AMVAD (OVA/Ms AMVAD) or Hs AMVAD (OVA/Hs AMVAD) vaccines prepared as described in Example 3.
Figure 9C:
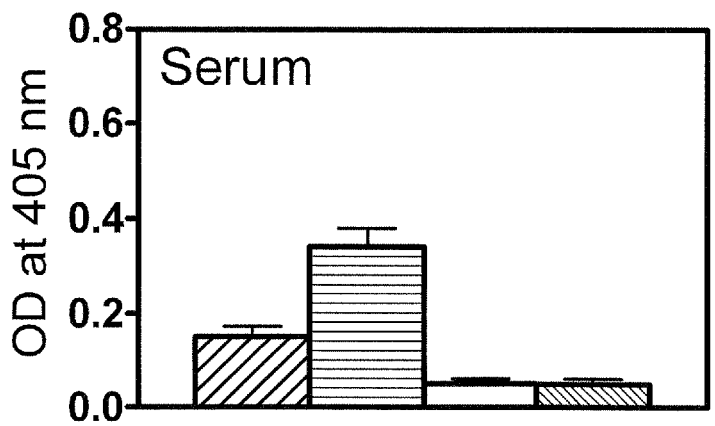
FIG. 9C shows elicitation of anti-OVA serum IgA titres (mean OD±SD) at 28 d, upon i.n. immunization (0, 7, 21 d) of groups of C57BL/6 mice with OVA (10 μg/immunization) formulated with Ms AMVAD (OVA/Ms AMVAD) or Hs AMVAD (OVA/Hs AMVAD) vaccines prepared as described in Example 3.

Anti-OVA IgA responses were observed in fecal, vaginal wash and serum samples collected from the OVA/Ms AMVAD and OVA/Hs AMVAD vaccinated groups of mice (FIGS. 9 A-9C). Little to no measurable IgA antibody responses were observed in the samples from the OVA/Ms archaeosome (s.c. vaccination) and the OVA/saline (i.n. vaccination) groups. The serum IgG, IgG1 and IgG2a responses were high, and comparable, in the two i.n. immunized OVA/AMVAD groups, and the s.c. immunized OVA/Ms archaeosome group (FIG. 9D-9F). There were measurable, but smaller systemic immune responses the i.n. immunized OVA/saline group.

Figure 10:
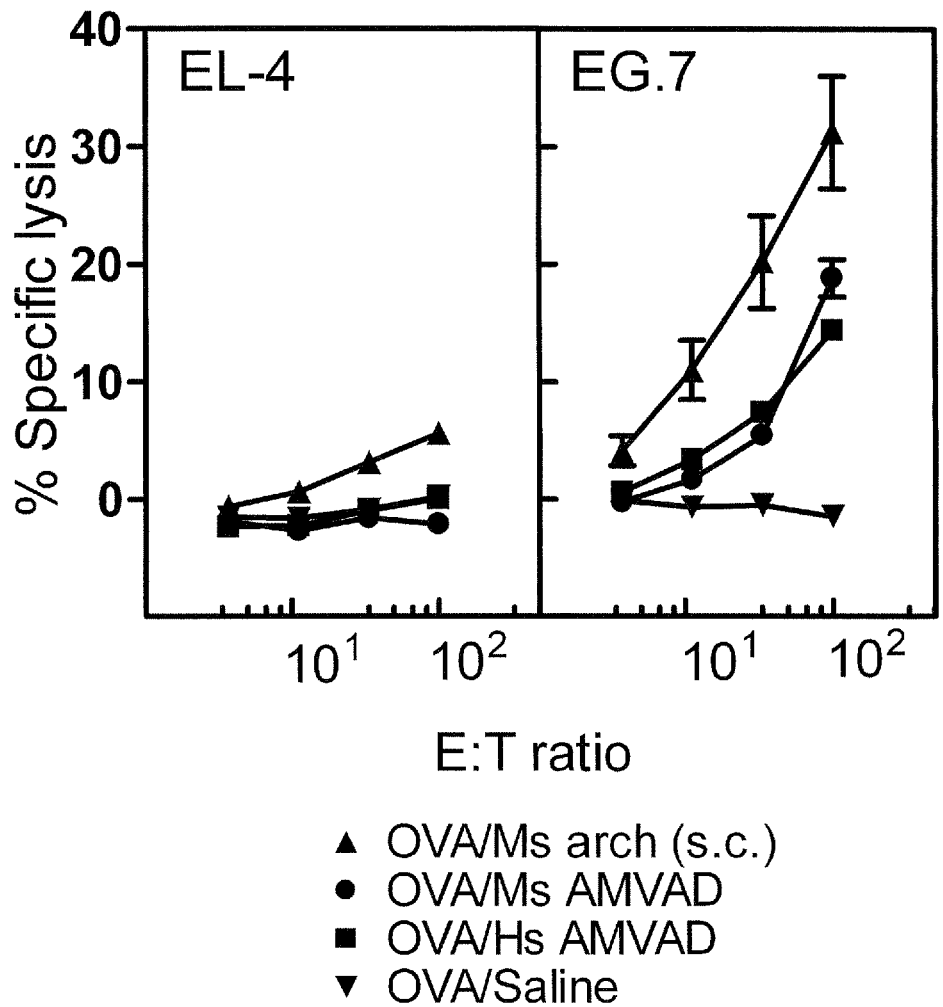
FIG. 10 shows the antigen specific CTL responses, as measured by the % specific lysis, elicited at 36-42 d, in the same groups of C57BL/6 mice that were immunized in FIG. 9. The results show that the OVA/Ms archaeosome s.c. vaccinated positive CTL control group exhibited ca 31% lysis of the target EG.7 cells compared with the 16-19% lysis with the OVA/Ms and OVA/Hs vaccinated groups. There was no CTL response in the OVA/saline group. Data represent the mean % specific lysis±SD of three independent assays which involved the spleens obtained from 2-3 mice from each group, at each assay.

The CTL assay indicated that the strongest response (ca 31% specific cell lysis) was observed in the group that was s.c. immunized with OVA/Ms archaeosome vaccine (FIG. 10), which was used as the positive control for the CTL assays. Good CTL responses were also observed in groups of mice i.n. immunized with OVA/Ms AMVAD and OVA/Hs AMVAD (16-19% specific cell lysis) vaccines, the responses being about 50% of that seen with the s.c. administered archaeosome vaccine (FIG. 10) which is known to elicit strong CTL responses upon systemic immunization. There was no CTL response in the group immunized i.n. with OVA/saline (FIG. 10).

Figure 11A:
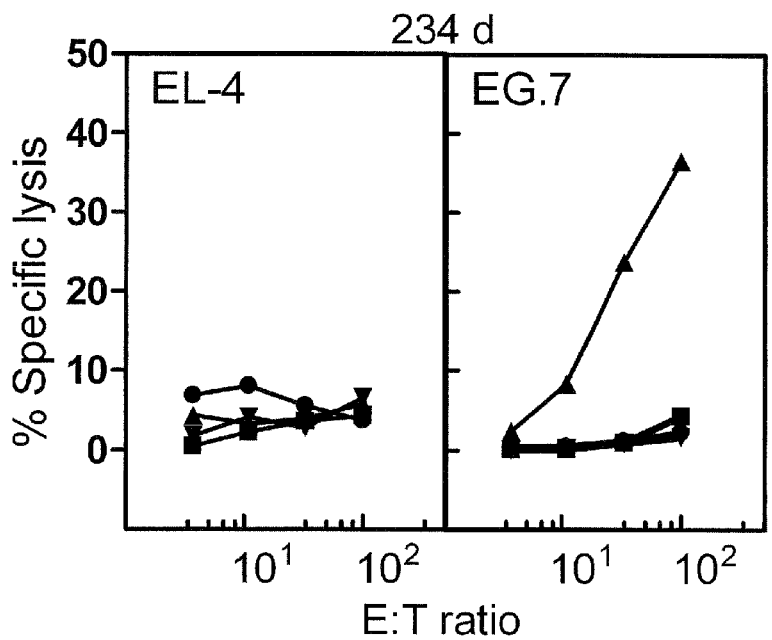
FIGS. 11A-11B show the antigen-specific memory CTL responses in C57BL/6 mice that were immunized (10 μg OVA/immunization at 0, 7 21 d) i.n. or s.c. with OVA/Ms AMVAD vaccine, i.n. with empty Ms AMVAD vaccine (Ms AMVAD, no OVA), or s.c. with OVA/Ms archaeosome vaccine (OVA/Ms arch) and then given an antigen alone boost (20 μg OVA/saline) at 251 d (except the empty Ms AMVAD group) via the s.c route.
Figure 11B:
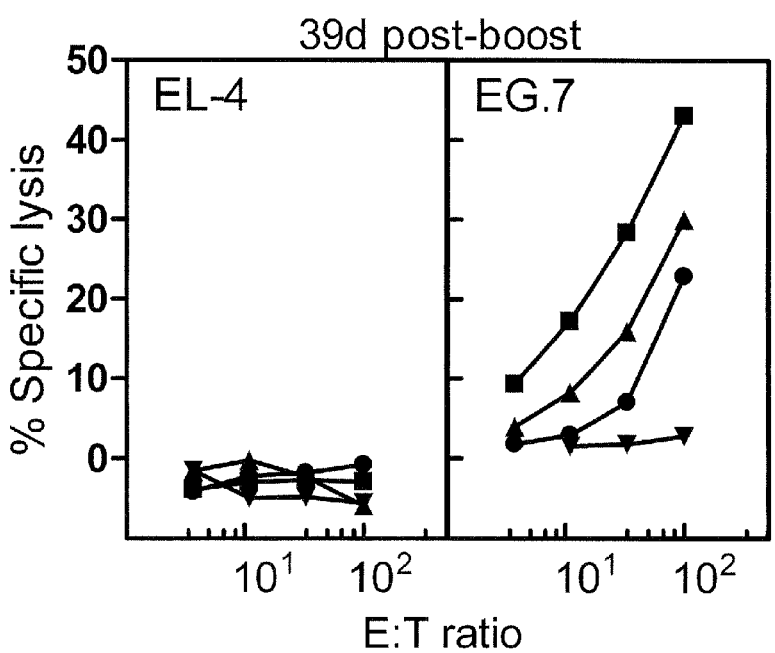

In another experiment, groups of C57BL/6 mice were similarly immunized at 0, 7 and 21 day, either i.n. with OVA/Ms AMVAD, empty Ms AMVAD, or s.c. with OVA/Ms archaeosome or OVA/Ms AMVAD vaccine. The CTL assays were conducted at 234 d using representative mice from each group. The remaining mice in all groups, were given a s.c. booster immunization on 251 d, with 20 µg OVA/saline, and the CTL assays were conducted on at 290 d (i.e. at 39 days post OVA alone boost). The results showed that only the s.c. immunized OVA/Ms archaeosome group had measurable CTL response at 234 d (FIG. 11A). However, upon antigen alone s.c. boost, CTL responses were also observed in OVA/Ms AMVAD groups immunized by the i.n. or the s.c. route (FIG. 11B). The results demonstrate that i.n. vaccination with OVA/Ms AMVAD vaccine elicits a primary CTL response that is subject to elicitation of a memory CTL response upon antigen alone boost.

Example 24

Elicitation of Mucosal and Systemic Immune Responses Upon i.n. Immunization with LMCE/Hs AMVAD Vaccine The *Listeria monocytogenes* cell-free extract/Hs AMVAD formulation (LMCE/Ms AMVAD) prepared in Example 11 was used to i.n. immunize (10 µg LMCE/immunization) C57BL/6 mice (female, 6-8 week old, n=5) at 0, 7 and 21 d as described in Example 17. Fecal, vaginal wash and serum samples were collected at 28 d and anti-LMCE antibody titres determined as described in Example 17, except that the sample dilutions for ELISA assays for vaginal IgA (1:10), serum IgA (1:50), and serum IgG (1:500) were changed as indicated in the brackets. Control groups (n=5) consisted of mice immunized with saline (0 µg LMCE/immunization) or 10 µg LMCE in saline (no adjuvant control).

Figure 12:
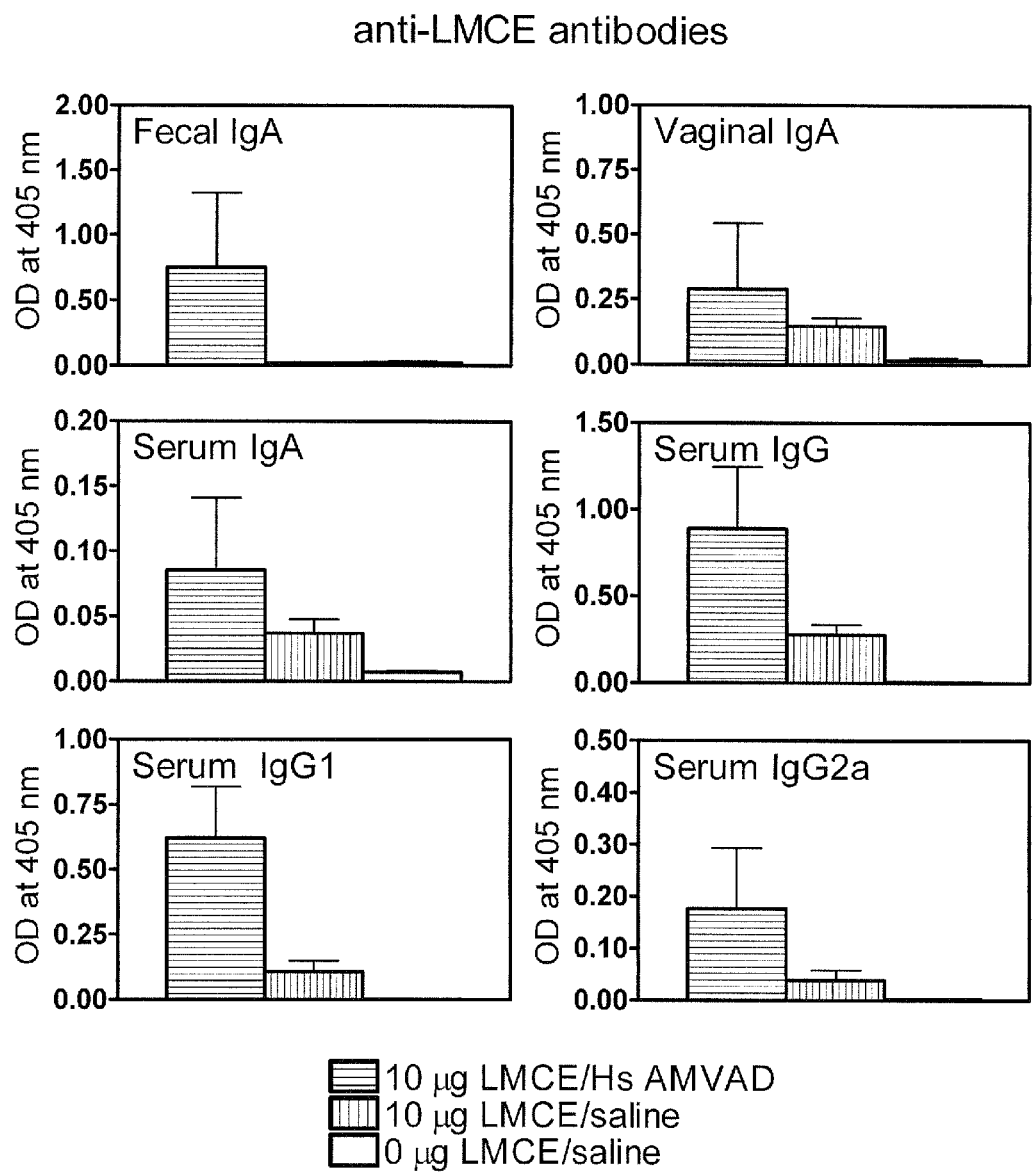
FIG. 12 shows elicitation of anti-LMCE fecal IgA, vaginal IgA, serum IgA, serum IgG, serum IgG1 and serum IgG2a antibody titres (mean OD±SD) at 28 day, after i.n. immunization (0, 7, 21 d) of groups of C57BL/6 mice with LMCE (10 μg/immunization) formulated with Hs AMVAD or in saline. A naïve group was included as the negative control. The results show that the antibody titres with the AMVAD vaccine were higher than those obtained with LMCE/saline.

The results show that LMCE alone elicits little to no anti-LMCE IgA, IgG, IgG1 or IgG2a antibody responses. However, the LMCE/Hs AMVAD vaccinated group had substantially elevated levels of anti-LMCE antibody responses compared with those seen in the 10 µg LMCE/saline group (FIG. 12). There were no measurable immune responses in the 0 µg LMCE/saline group.

Example 25

Elicitation of Mucosal Immune Responses by HPCE/Ms AMVAD Vaccine Administered Via the Per Oral (p.o.) Route The *H. pylori* cell free extract/Ms AMVAD formulation (HPCE/Ms AMVAD) was prepared as described in Example 13, using a starting lipid:protein ratio (w/w) of 4:1. The antigen loading in this formulation was 141.5 µg HPCE/mg lipid. Female, Balb/c mice (6-8 week old, n=5) were p.o. immunized at 0, 7 and 21 d at a dose of 100 µg HPCE/immunization, and fecal, vaginal wash and serum samples were collected at 28 d and analyzed for antibody responses, as described in Example 17, except that the dilutions of samples for ELISA assays for serum IgA (1:100), serum IgG, IgG1 and IgG2a (1:1000) were as indicated in the brackets. Groups of mice similarly immunized with CT adjuvant (10 µg CT/100 µg HPCE) or with 100 µg HPCE in saline (HPCE/saline, no adjuvant) were included as controls.

Figure 13:
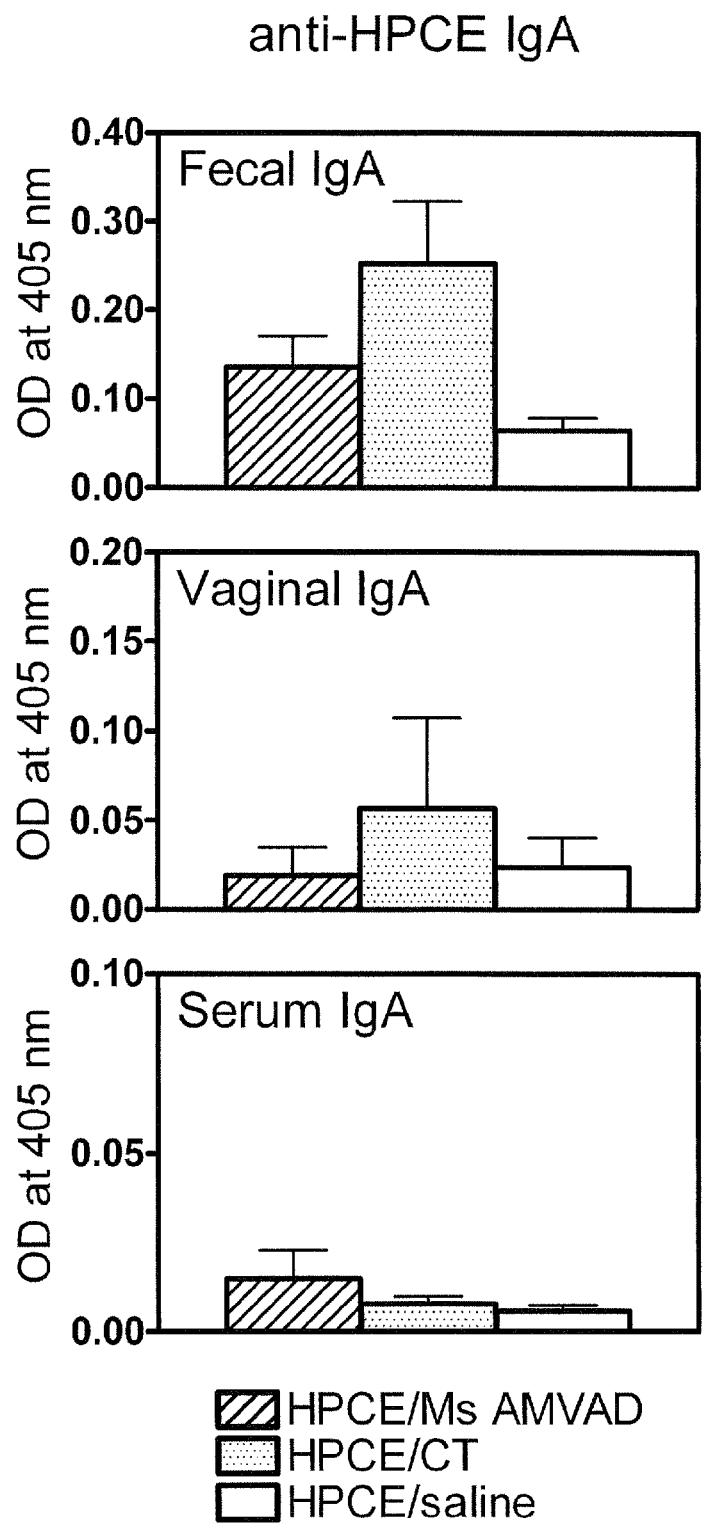
FIG. 13 shows elicitation of anti-HPCE fecal IgA, vaginal IgA, and serum IgA antibody titres (mean OD±SD) at 28 day, upon p.o. immunization (0, 7, 21 d) of groups of Balb/c mice with HPCE (100 μg/immunization) formulated with Ms AMVAD (HPCE/Ms AMVAD), cholera toxin (HPCE/CT) or with saline (HPCE/saline, no adjuvant). It is seen that the antibody responses upon p.o. immunization with AMVAD vaccine are comparable to those obtained with CT, and both are higher than those obtained with HPCE alone in saline.

The results showed that the anti-HPCE fecal IgA antibody responses in the AMVAD and CT vaccinated groups were higher than those in the HPCE/saline group, and the vaginal and serum IgA responses in all groups were negligible (FIG. 13). The elicitation of immunity by p.o. immunization with the AMVAD vaccine was comparable to that obtained with the CT vaccine.

Example 26

Elicitation of Mucosal Immunity by HPCE/Ms AMVAD Vaccine Administered Via the i.n. Route, and Protection Against Colonization Upon p.o. Challenge The *H. pylori* cell free extract/Ms AMVAD formulation (HPCE/Ms AMVAD) was prepared as described in Example 13, using a starting lipid:protein ratio (w/w) of 2:1. The antigen loading in this formulation was 239.7 µg HPCE/mg lipid. Female, Balb/c mice (6-8 week old, n=7-8) were i.n. immunized at 0, 7 and 21 d with HPCE/Ms AMVAD vaccine (AMVAD) at a dose of 10, 25 or 150 µg HPCE/immunization, and fecal and serum samples were collected at 32 d and analyzed for antibody responses, as described in Example 17, using samples dilutions as indicated in Example 25 for the ELISA assays. Groups of mice similarly immunized with HPCE using either CT (1 µg CT) as the adjuvant (CT), or in saline (saline, no adjuvant group) were included as controls. A naïve group (0 µg HPCE/saline) was included as a negative control.

All mice were challenged p.o. at 41 and 43 d by gavaging 0.5 ml of *H. pylori* culture containing $3.8 \times 10^9$ and $3.4 \times 10^{10}$ colony forming units (CFU), respectively. Fecal and serum samples were collected at 91 d, the mice were euthanized and the *H. pylori* burdens in the stomach were determined by plating serially diluted tissue extracts on blood agar which was supplemented with the GSS supplement as described in Example 13. The typical *H. pylori* colonies were enumerated after 3 d incubation (37° C., 85% $N_2$:10% $CO_2$:5% $O_2$ atmosphere). The minimum detection level was $1 \times 10^3$/CFU per organ, and when no CFU were observed at this level, the stomach and the mouse was considered to be not colonized. Statistical analyses of the percentage of mice colonized with *H. pylori* were done by $x^2$ test. Values are considered to be statistically significant if $p < 0.05$.

Figure 14:
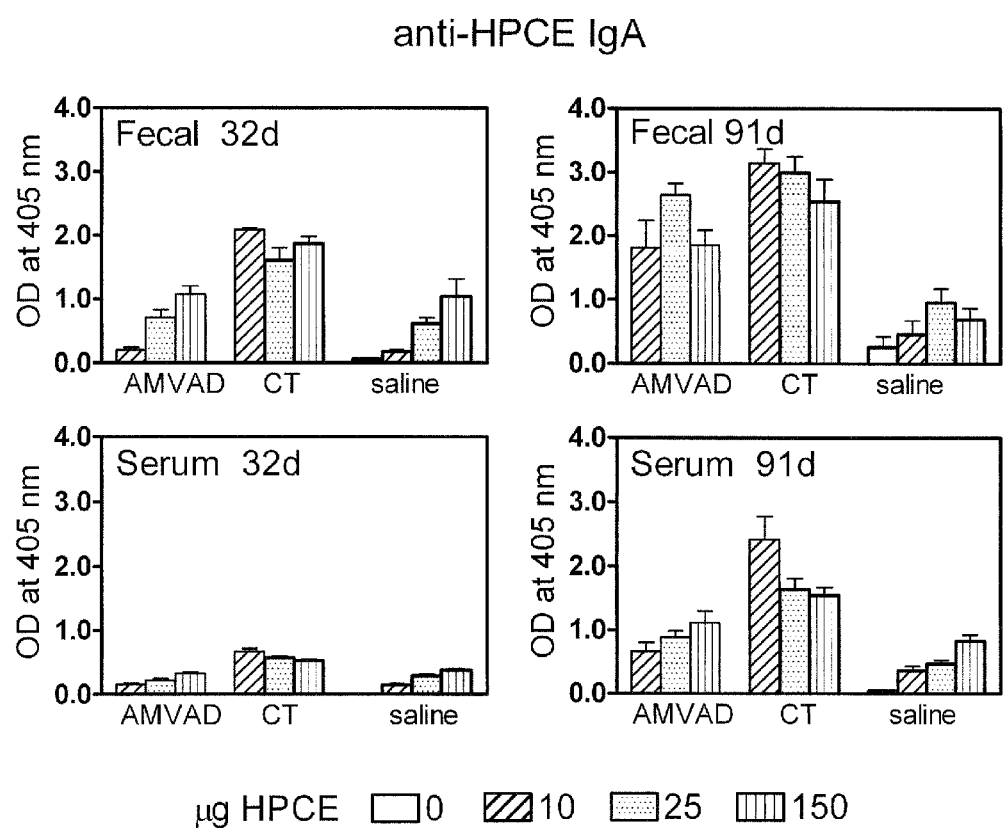
FIG. 14 shows anti-HPCE fecal and serum IgA antibody titres at 32 d upon i.n immunization (0, 7, 21 d) of groups of Balb/c mice with 10, 25 or 150 μg HPCE/immunization when formulated with Ms AMVAD (AMVAD), cholera toxin (CT) or with saline (saline). The antibody responses at 91 d represent titres subsequent to the p.o. challenge with ca $10^9$ CFU of *H. pylori* at 41-43 d. In response to the challenge, there was a substantial increase in the antibody titres of all groups of mice immunized with the AMVAD and CT vaccines, whereas there was no change in titres of the group immunized with 0-150 μg HPCE alone in saline.

There were no measurable anti-HPCE fecal or serum IgA antibody responses (FIG. 14), in the naïve group (0 µg HPCE) of mice at 32 and 91 d. At 32 d, the anti-HPCE fecal and serum IgA antibody responses in the AMVAD and saline (no adjuvant) groups immunized with 10-150 µg HPCE were comparable to each other at the equivalent HPCE immunization doses, but the responses with CT adjuvant were higher (FIG. 14). However, subsequent to the p.o. challenge with *H. pylori*, the fecal and serm IgA responses in the AMVAD and CT groups at 91 d were substantially elevated compared to the titres at 32 d. In contrast, the comparative titres in the HPCE/saline group were not as elevated compared with the 32 d titres (FIG. 14).

The results of the challenge experiment indicated that the mice vaccinated with the AMVAD vaccine were better protected against colonization, as compared to the group immunized with the antigen alone in saline (Table 1). The protection against colonization of the stomach in AMVAD vaccinated group was comparable to that seen with the CT group. At the highest dose of 150 µg HPCE, none of the mice in the AMVAD group had detectable level of *H. pylori* colonization, compared with 50% of the mice in the antigen alone (no adjuvant) that were colonized. This difference in colonization between the AMVAD vaccinated and saline groups was statistically significant ($p < 0.05$).

TABLE 1

Mice i.n. immunized with HPCE/Ms AMVAD vaccine are protected against stomach colonization upon p.o. challenge[1].

| | % of mice colonized[2] | | |
|---|---|---|---|
| µg HPCE | Ms AMVAD | CT | Saline |
| 0 | ND[3] | ND[3] | 85.7 |
| 10 | 50.0 | 42.9 | 85.7 |

TABLE 1-continued

Mice i.n. immunized with HPCE/Ms AMVAD vaccine are protected against stomach colonization upon p.o. challenge[1].

| | % of mice colonized[2] | | |
|---|---|---|---|
| μg HPCE | Ms AMVAD | CT | Saline |
| 25 | 37.5 | 50.0 | 75.0 |
| 150 | 0.0* | 12.5 | 50.0 |

[1]Groups of Balb/c mice were immunized i.n. (0, 7, 21 d) with the indicated doses of HPCE in HPCE/Ms AMVAD (Ms AMVAD), HPCE/cholera toxin (CT) or HPCE/saline (saline, no adjuvant) vaccines. The mice were p.o. challenged with $H.$ $pylori$ at 41 ($3.8 \times 10^9$ CFU) and 43 d ($3.4 \times 10^{10}$ CFU), and the $H.$ $pylori$ burden in the stomachs determined at 91 d as described in Example 26.
[2]The minimum pathogen detection limit is $1 \times 10^3$ CFU/organ, and the stomach and the mouse is considered to be not colonized when no pathogens are detected at this level.
[3]ND—not determined.
*p < 0.05 vs. HPCE/saline group at 150 μg HPCE dosage.

Example 27

Elicitation of Mucosal and Systemic Immune Responses Upon i.n. Immunization with PsaA/AMVAD Vaccines Balb/c mice (female, 6-8 week old, n=5/group) were immunized i.n. (at 1 μg PsaA antigen dose/immunization) at 0, 7 and 21 d with PsaA/Ms AMVAD or PsaA/Hs AMVAD vaccine formulations prepared in Example 14, as described in Example 17. The PsaA loading in PsaA/Ms AMVAD and PsaA/Hs AMVAD preparations was 30.0 and 26.2 μg PsaA/mg lipid, respectively. Fecal, vaginal wash and serum samples were collected at 28 d, and anti-PsaA antibody responses determined, as described in Example 17, except that the dilutions of samples for ELISA assays for serum IgA (1:50) and serum IgG2a (1:500) were as indicated in brackets. Control groups of mice were similarly immunized with PsaA adjuvanted with CT (1 μg CT/1 μg PsaA) or with no adjuvant (1 μg PsaA/saline).

Figure 15:
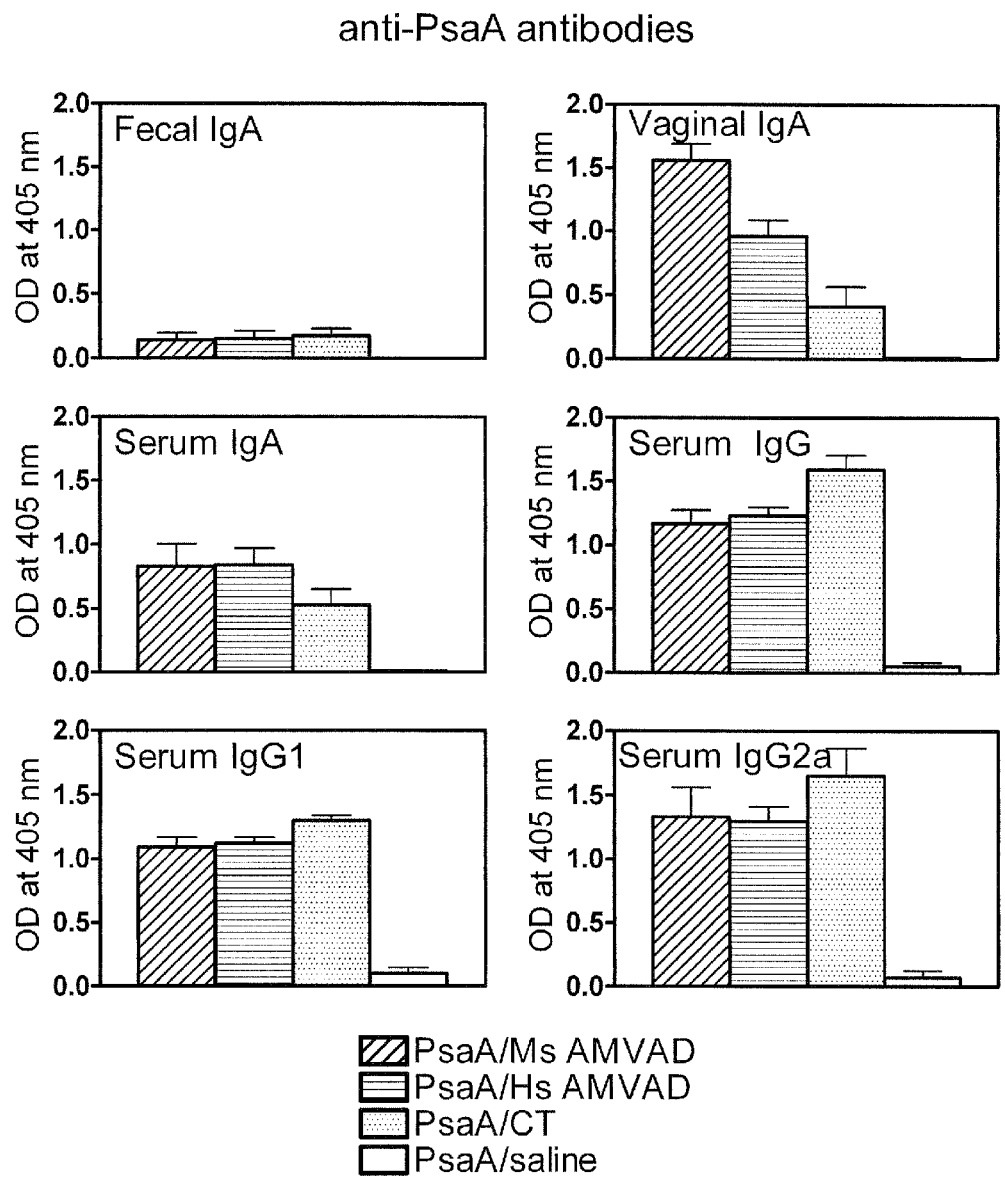
FIG. 15 shows elicitation of anti-PsaA fecal IgA, vaginal IgA, serum IgA, serum IgG, serum IgG1 and serum IgG2a antibody titres (mean OD±SD) at 28 d, upon i.n. immunization (0, 7, 21 d) of groups of Balb/c mice with PsaA (1 μg PsaA/immunization) formulated with Ms AMVAD (PsaA/Ms AMVAD), Hs AMVAD (PsaA/Hs AMVAD) prepared as described in Example 14, or with cholera toxin (PsaA/CT). One control group was similarly i.n immunized with PsaA/saline (no adjuvant). The antibody titres in the two groups of mice immunized with the AMVAD vaccines were high and comparable to those obtained with the CT group. There was little to no response in the absence of an adjuvant.

Results (FIG. 15) demonstrate that in the absence of any adjuvant (PsaA/saline), there are no measurable mucosal IgA responses, and negligible systemic responses (serum IgG subtype responses) immune responses. However, immunization with PsaA/Ms or PsaA/Hs AMVAD vaccine elicited anti-PsaA IgA (feces, vaginal wash, serum) and anti-PsaA serum IgG, IgG1 and IgG2a antibody responses that were comparable to those elicited by the CT vaccine (FIG. 15).

Example 28

Elicitation of Mucosal and Systemic Immune Responses Upon i.n. Immunization with O-Chain/Ms AMVAD Vaccine Balb/c mice (female, 6-8 week old, n=5/group) were immunized i.n. or s.c. (20 μg O-chain antigen dose/immunization, equivalent to 67.6 μg O-chain-BSA conjugate) at 0, 7 and 21 d, with O-chain/Ms AMVAD vaccine formulation prepared in Example 15, as described in Example 17. The O-chain-BSA conjugate loading in O-chain/Ms AMVAD preparation was 92.9 μg/mg lipid, with the O-chain equivalent being 38.1 μg/mg lipid. Fecal, vaginal wash and serum samples were collected at 28 d, and anti-O-chain antibody responses determined, as described in Example 17, except that the dilutions of samples for ELISA assays for vaginal IgA (1:25), serum IgA (1:50) and serum IgG (1:100) were as indicated in the brackets. Control groups of mice were similarly immunized i.n. with O-chain conjugate adjuvanted with CT (1 μg CT/20 μg O-chain) or with O-chain conjugate with no adjuvant (20 μg O-chain/saline).

Figure 16:
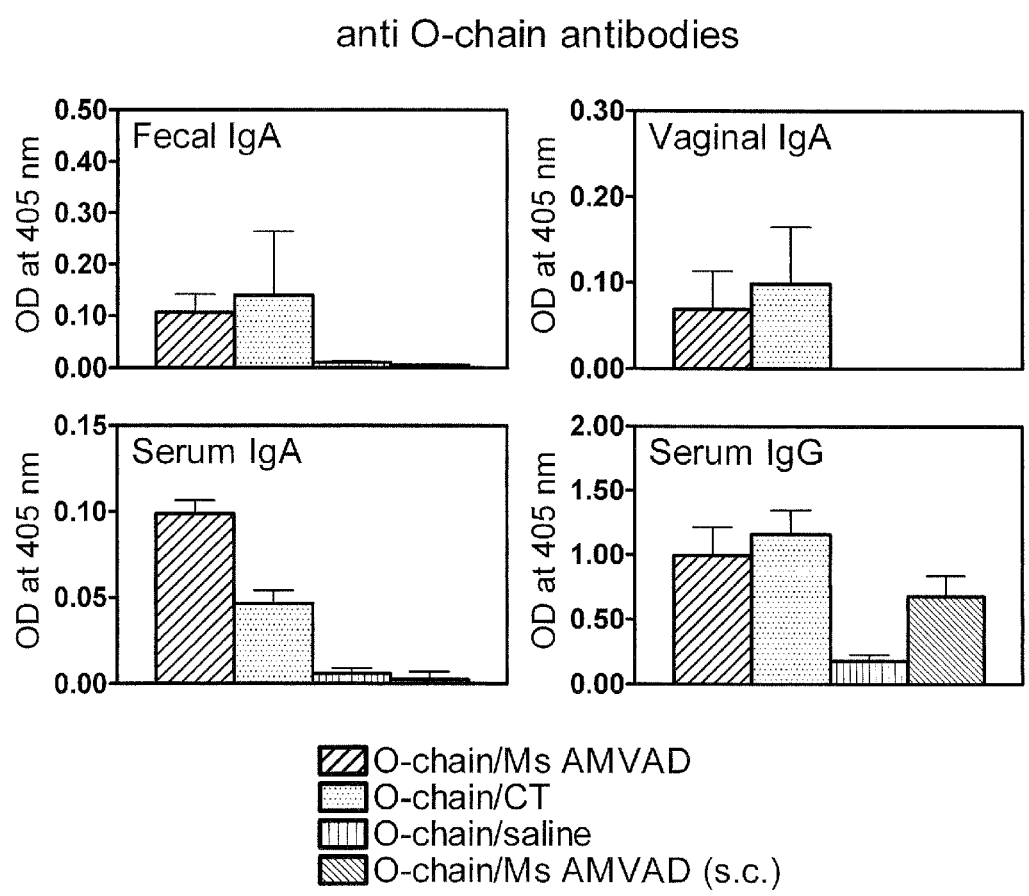
FIG. 16 shows anti-O-chain fecal IgA, vaginal IgA, serum IgA and serum IgG antibody titres (mean OD±SD) at 28 d, upon i.n. or s.c. immunization (0, 7, 21 d) of groups of Balb/c mice with O-chain-BSA conjugate (20 μg O-chain/immunization) formulated with Ms AMVAD (O-chain/Ms AMVAD) prepared as described in Example 15, or i.n. with O-chain conjugate adjuvanted with 1 μg cholera toxin (O-chain/CT). One control group was similarly i.n immunized with O-chain-BSA conjugate/saline (O-chain/saline, no adjuvant). The results demonstrate that AMVAD vaccines elicit strong O-chain specific IgA and IgG responses, which were comparable to those obtained with the CT group.

Results demonstrate that in the absence of any adjuvant (O-chain/saline), there were negligible to no measurable anti-O-chain mucosal IgA antibody responses (FIG. 16). However, anti-O-chain IgA antibody responses were observed in the groups that were i.n. immunized with the AMVAD or the CT vaccine, and these responses in the two groups were comparable (FIG. 16). The mouse group immunized s.c. with AMVAD vaccine elicited negligible to no measurable anti-O-chain IgA antibody responses, but did elicit strong serum IgG response. The group immunized with O-chain/saline vaccine elicited little serum IgG response, but the groups immunized with CT or AMVAD vaccines, including the group s.c. immunized with AMVAD vaccine, elicited strong serum anti-O-chain IgG antibody responses (FIG. 16).

Example 29

Immunostimulatory Properties of Empty Ms AMVAD Formulation

C57BL/6 mice (female, 6-8 week old) were i.n. immunized once at 0 d, with empty Ms AMVAD formulation (in saline) prepared by the standard protocol as described in Example 3, as described in Example 17. The immunization volume of 50 μl contained Ms AMVAD formulation equivalent to 0.2 mg dry weight of lipid (Ms TPL). Groups of 3 mice were sacrificed at day 0, 1, 2, 3, 7, 14 and 21 post-immunization, and their lungs were lavaged with 5×1 ml PBS containing 30 mM EDTA. The total cell numbers in the collected bronchoalveolar lavage (BAL) fluids were counted on a haemocytometer.

Figure 17:
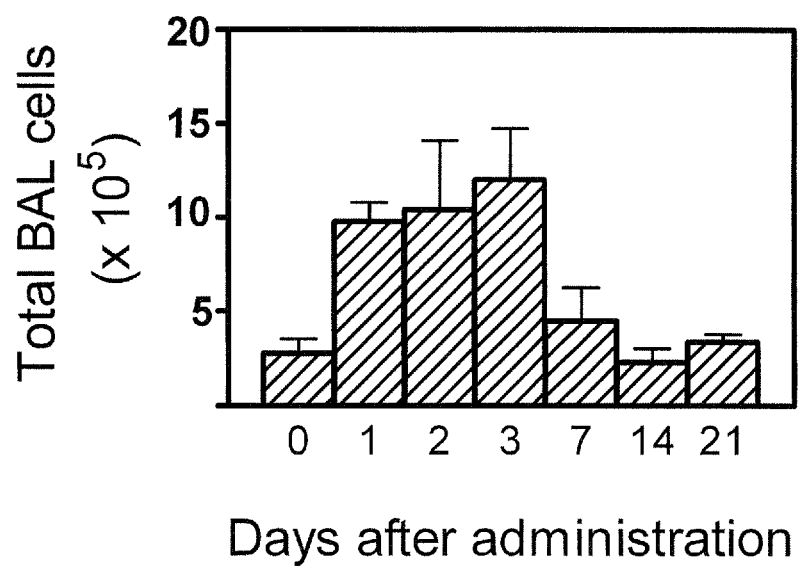
FIG. 17 shows the induction of inflammatory and immunologic responses (infiltration of macrophages, neutrophils and lymphocytes) in the lungs of mice following the intranasal administration of empty Ms AMVAD in saline, prepared by the standard protocol as described in Example 3. Mice were i.n. immunized at 0 d as described in Example 17, with AMVAD formulation equivalent to 0.2 mg dry weight of lipid (Ms TPL) in 50 μl saline. Groups of mice were sacrificed at the indicated times subsequent to the immunization, and their lungs were lavaged. The total cell numbers in the bronchoalveolar lavage (BAL) were enumerated. Each bar represents the mean total cell count±SD of 3 mice.

Intranasal administration of empty Ms AMVAD (absence of an antigen) induced remarkable but transient inflammatory and immunologic responses in the lungs (infiltration of macrophages, neutrophils and lymphocytes), which peaked at 24 hours and returned to baseline level by $7^{th}$ day after the administration (FIG. 17). These data suggest that AMVAD structure is immunostimulatory but at the same time it does not induce persistent inflammation at the site of immunization, the latter of which could be detrimental to the host.

Example 30

Preparation of AMVAD Structures Using Other Divalent Cations, Trivalent Cations, and Multivalent Organic Cationic Compounds Empty, unilamellar Ms archaeosomes were prepared in water, as described in Example 2. The Ms archaeosomes were successfully converted into AMVAD structures (as observed under phase contrast microscopy) by drop-wise addition of 0.5 M sock solution of any one of the following divalent cationic solutions $MgCl_2.6H_2O$, $MgSO_4.7H_2O$, $ZnCl_2$, or $ZnSo_4.7H_2O$ instead of $CaCl_2$, as described in Example 3. The molar ratio of lipid: $Mg^{2+}$ or lipid:$Zn^{2+}$ in these preparations was 1:1, and the final concentration of the respective salts in the preparation at this stage was 19.2 mM in each instance.

The empty Ms archaeosomes could also be converted into typical AMVAD structures by the drop-wise addition of either trivalent ($AlCl_3$; 0.5 M) or quadruvalent ($AlK(SO_4)_2.12H_2O$; 0.1 M) cationic stock solutions, instead of $CaCl_2$, as described in Example 3. The molar ratio of lipid:aluminium in these formulations was 1:0.5 and 1:0.2, respectively.

Empty Ms archaeosomes could also be converted into typical AMVAD structures by the drop-wise addition of organic, multivalent cationic solution of tobramycin sulphate (0.1 M) or 2,4,5,6-Tetraminopyrimidine sulphate (0.01 M). The molar ratio of lipid:tobramycin was 1:0.2 in the tobramycin/Ms AMVAD formulation, and the molar ratio of lipid: tetraminopyrimidine sulphate was 1:1.5 in the tetraminopyrimidine sulphate/Ms AMVAD formulation.

Example 31

Efficacy in the elicitation of OVA-specific immune responses in mice by OVA/AMVAD-ANW formulations prepared by admixing protocol as described in Example 5, but using different starting ratios (w/w) of TPL:OVA (from 32:1 to 4:1), and also after reducing the AMVAD particle size Two batches of OVA/Ms AMVAD-ANW were prepared as described in Example 5, but using a starting TPL:OVA ratio (w/w) of 32:1 when admixing empty Ms archaeosomes with OVA (31.25 µg total OVA/mg lipid in formulation, i.e., 10 µg total OVA/0.32 mg lipid in formulation). In this OVA/Ms AMVAD-ANW/0.32 (10 µg OVA/0.32 mg lipid) formulation, ca 5%, 8%, 67% and 20% of the AMVAD structures were in the size ranges (widths) of <5 µm, 6-9 µm, 10-30 µm and >30 µm, respectively. The AMVAD structure sizes were determined using phase contrast microscopy as described in Example 3, using a minimum of 100 random measurements per formulation. Five sterile glass beads (ca 3 mm diameter each) were added to one batch of the above formulation contained in a 15 ml glass test tube, and the tube was vortexed for a period of 3-5 min to reduce the size of the AMVAD structures in the formulation. In this OVA/Ms AMVAD-ANW/0.32-SR (10 µg OVA/0.32 mg lipid) formulation, approximately 40% of the total OVA in the formulation was AMVAD particle associated. In the OVA/Ms AMVAD-ANW/0.32-SR formulation, ca 75%, 15% and 9% of the AMVAD structures were in the size ranges of <5 µm, 6-9 µm and 10-30 µm, respectively, indicating that the bulk of the AMVAD particle structures were 5 µm or less in width. Additional OVA/Ms AMVAD-ANW formulations, without size reduction, were prepared as described above, using starting TPL:OVA ratios of 16:1 (10 µg OVA/0.16 mg lipid; OVA/Ms AMVAD-ANW/0.16), 8:1 (10 µg OVA/0.08 mg lipid; OVA/Ms AMVAD-ANW/0.08) or 4:1 (10 µg OVA/0.04 mg lipid; OVA/Ms AMVAD-ANW/0.04).

Groups of Balb/c mice (n=5) were intranasally immunized at 0, 7, and 21 d with OVA/Ms AMVAD-ANW/0.32-SR, OVA/Ms AMVAD-ANW/0.32, OVA/Ms AMVAD-ANW/0.16, OVA/Ms AMVAD-ANW/0.08 or OVA/Ms AMVAD-ANW/0.04 formulation at 10 µg OVA dose per mouse, per immunization in 50 µl immunization volume, as described in Example 17. An additional group of mice was similarly immunized at 10 µg OVA dose with OVA/Ms AMVAD-ANW/0.32 formulation but in 10 µl immunization volume (OVA/Ms AMVAD/0.32-10 µl). Another additional group was similarly immunized in 50 µl immunization volume with a dose of 1 µg OVA per immunization, using OVA/Ms AMVAD-ANW/0.32 (10 µg OVA/0.32 mg lipid) formulation that was diluted 10-fold in saline/15 mM $CaCl_2$ prior to immunization. The latter formulation is referred to as OVA/Ms AMVAD-ANW/1 µg OVA-32 µg lipid. At 28 d, vaginal wash, nasal wash and serum samples were collected and the elicited OVA-specific antibody responses were measured by ELISA assays, as described in Example 17.

Figure 18A:
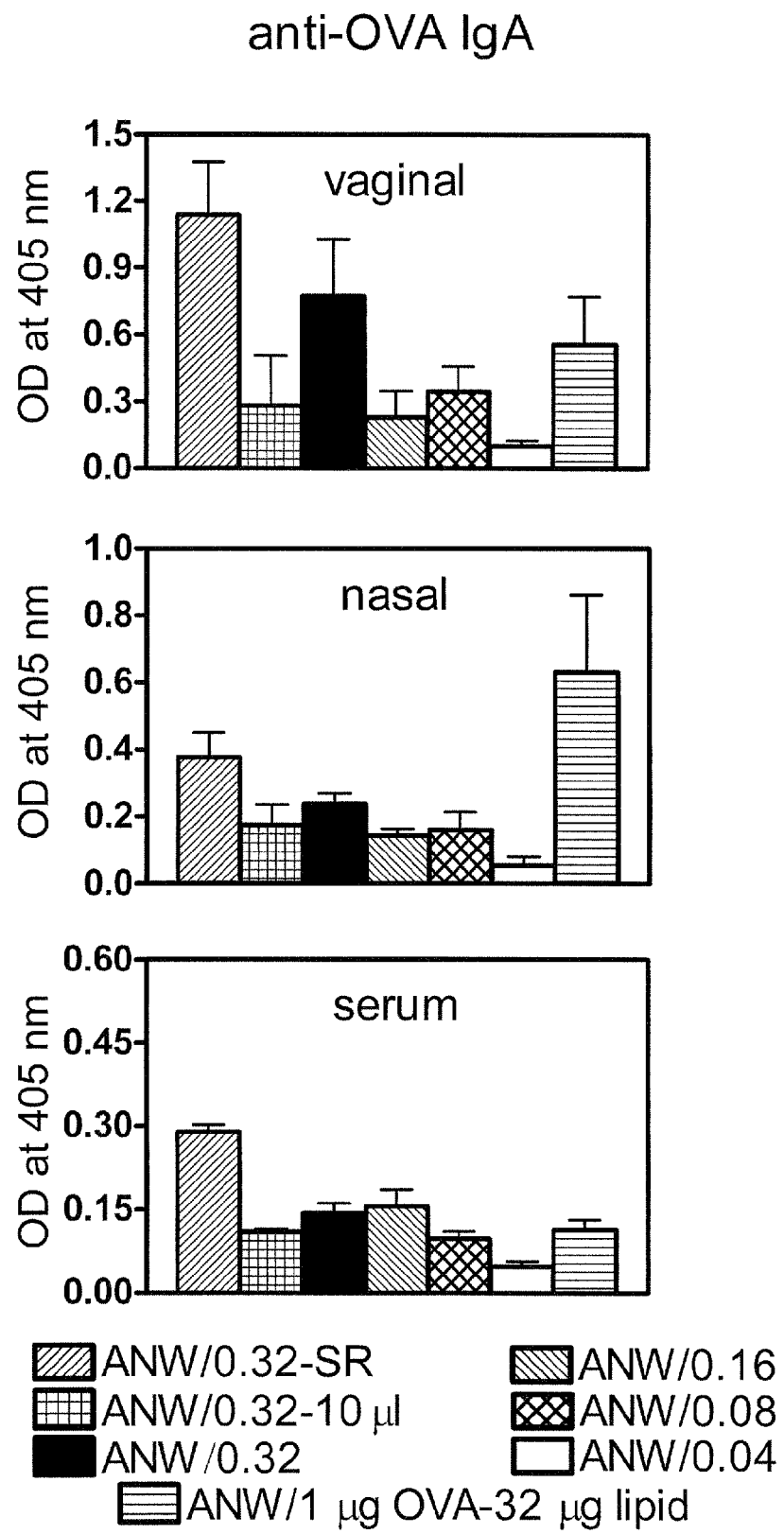
FIG. 18A shows elicitation of anti-OVA vaginal, nasal and serum IgA antibody responses (mean OD±SD) at 28 day, upon i.n. immunization (0, 7, 21 d) of groups of Balb/c mice (n=5) with OVA/Ms AMVAD-ANW/0.32-SR (10 μg OVA/0.32 mg lipid; ANW/0.32-SR), OVA/Ms AMVAD-ANW/0.32 (10 μg OVA/0.32 mg lipid; ANW/0.32), OVA/Ms AMVAD-ANW/0.16 (10 μg OVA/0.16 mg lipid; ANW/0.16), OVA/Ms AMVAD-ANW/0.08 (10 μg OVA/0.08 mg lipid; ANW/0.08) or OVA/Ms AMVAD-ANW/0.04 (10 μg OVA/0.04 mg lipid; ANW/0.04) formulation at 10 μg OVA dose per mouse, per immunization in 50 μl immunization volume.
Figure 18B:
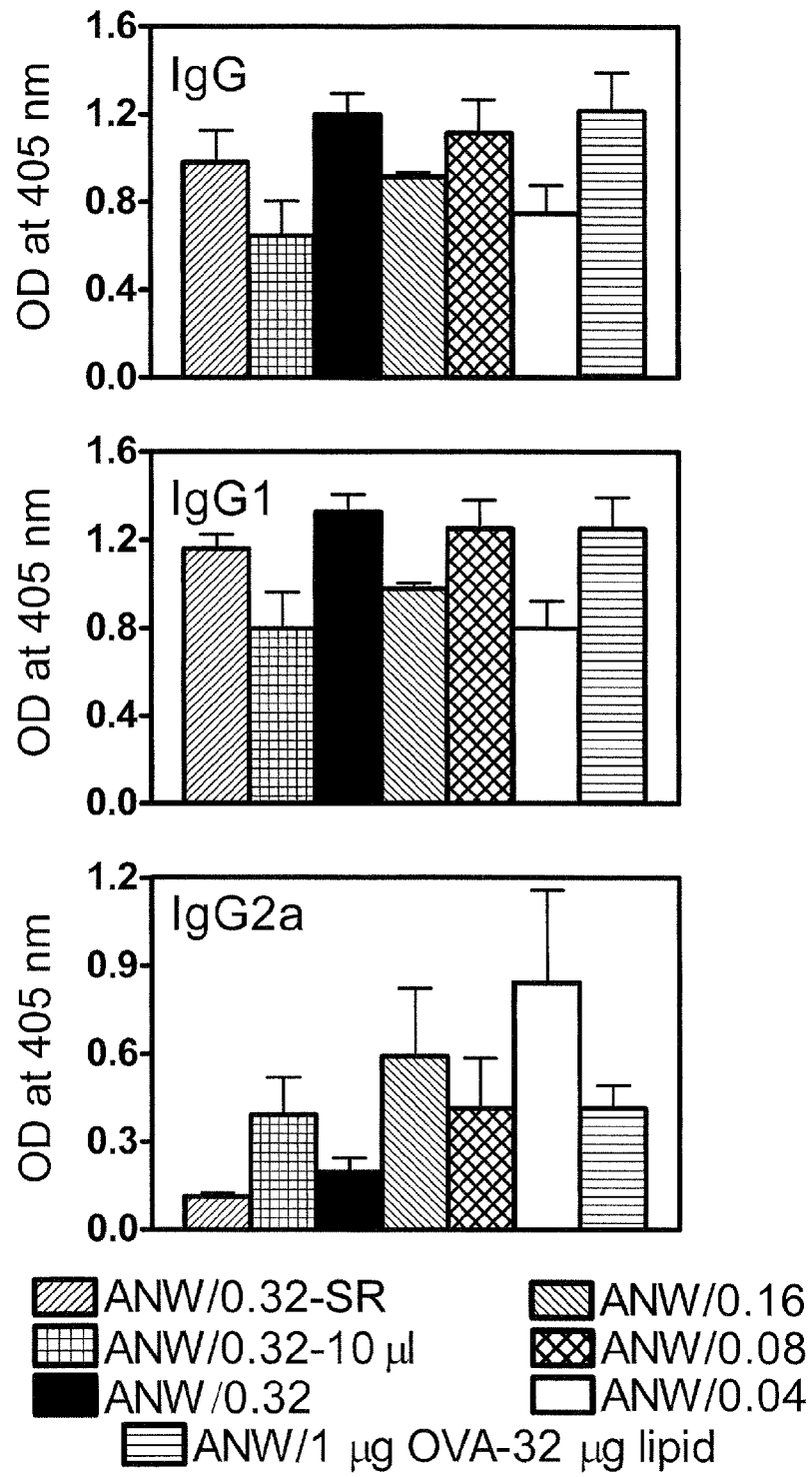
FIG. 18B shows elicitation of anti-OVA serum IgG, IgG1 and IgG2a antibody responses (mean OD±SD) at 28 day, upon i.n. immunization (0, 7, 21 d) of groups of Balb/c mice (n=5) with OVA/Ms AMVAD-ANW/0.32-SR (10 μg OVA/0.32 mg lipid; ANW/0.32-SR), OVA/Ms AMVAD-ANW/0.32 (10 μg OVA/0.32 mg lipid; ANW/0.32), OVA/Ms AMVAD-ANW/0.16 (10 μg OVA/0.16 mg lipid; ANW/0.16), OVA/Ms AMVAD-ANW/0.08 (10 μg OVA/0.08 mg lipid; ANW/0.08) or OVA/Ms AMVAD-ANW/0.04 (10 μg OVA/0.04 mg lipid; ANW/0.04) formulation at 10 μg OVA dose per mouse, per immunization in 50 μl immunization volume. Additional groups of mice were similarly immunized with OVA/Ms AMVAD-ANW/0.32 formulation but in 10 μl immunization volume (10 μg OVA/Ms AMVAD-ANW/0.32-10 μl; ANW/0.32-10 μl), or with OVA/Ms AMVAD-ANW/1 μg OVA-32 μg lipid (ANW/1 μg OVA-32 μg lipid) formulation (in 50 μl immunization volume) that was obtained by making a 10-fold dilution of OVA/Ms AMVAD-ANW/0.32 formulation in saline/15 mM $CaCl_2$. The results show that all these formulations elicit good and generally comparable OVA-specific mucosal and systemic immune responses.

The anti-OVA IgA antibody responses in vaginal wash, nasal wash, and sera (FIG. 18A), and anti-OVA IgG, IgG1 and IgG2a antibody responses in sera (FIG. 18B) showed that these responses were generally comparable in all groups of mice intranasally immunized with OVA/Ms AMVAD-ANW formulations (10 µg OVA dose in 50 µA volume) irrespective of the ratio (w/w) of lipid:OVA in the range of 32:1 to 4:1. Therefore, even at a lipid dose of 0.08 or 0.04 mg per mouse, the OVA-specific mucosal and systemic immune responses obtained were comparable to those attained with the higher lipid doses in the AMVAD vaccine formulations. The results also showed that the reduction in the size of the bulk of the AMVAD structures in the formulation to less than 5 µm widths (OVA/Ms AMVAD-ANW-SR), elicited comparable immune responses to those obtained with the formulation (OVA/Ms AMVAD-ANW) without size reduction, where the bulk of the AMVAD structures were >5 µm in width. Further, the immune responses were comparable when an identical antigen/lipid dose (10 µg OVA in 0.32 mg lipid in OVA/Ms AMVAD-ANW formulations) was administered in 10 µl volume instead of 50 µl. The results also demonstrated that comparably good mucosal and systemic immune responses were achieved with immunization dose as low as 1 µg OVA in 32 µg of lipid in the AMVAD formulation.

Example 32

Protective efficacy against intranasal *Francisella tularensis* LVS challenge in mice intranasally immunized with LVSCE/Ms AMVAD-ANW-SR formulations prepared by admixing of empty Ms archaeosomes with *F. tularensis* LVS cell free extract

*Francisella tularensis* LVS cell free extract (LVSCE) obtained in Example 12 was used to prepare the vaccine formulations in this example. Formulation of LVSCE/Ms AMVAD-ANW was prepared by admixing of empty, unilamellar Ms archaeosomes prepared from the TPL of *M. smithii* with LVSCE antigen, as described for preparing OVA/Ms AMVAD-ANW formulation in Example 5, with the exception noted below. The starting ratio (w/w) of TPL:LVSCE protein was 200:1 (5 μg LVSCE/mg lipid or 1 μg LVSCE/0.2 mg lipid) at the time of adding LVSCE to empty archaeosomes prior to their conversion to AMVAD structures, instead of the TPL:OVA ratio of 22.2:1 in Example 5. The molar ratio of lipid:Ca in this formulation was 1:5 and the $CaCl_2$ concentration was 50 mM. The LVSCE/Ms AMVAD-ANW formulation was vortexed in the presence of glass beads to reduce the size of the AMVAD particulates, as described in Example 31. Approximately 80% of the AMVAD structures in the size reduced LVSCE/Ms AMVAD-ANW-SR formulation were <5 μm in width, and about 12% were between 6 to 9 μm in width.

Groups of Balb/c mice (n=10) were intranasally immunized (50 μl volume) at 0, 7 and 21 d with 1 μg LVSCE in saline or 1 μg LVSCE/Ms AMVAD-ANW-SR formulation, as described in Example 17. A control group was similarly sham-immunized with only saline. At 28 d, vaginal wash and serum samples were collected from all mice, and anti-LVSCE antibody responses were evaluated by ELISA method, as described in Example 17, except that the samples for serum IgG and serum IgA were diluted 1:1000 and 1:50, respectively. At 35 d, 5 mice per each group (after anaesthetizing as done for i.n. immunization) were intranasally challenged with $2.8\times10^5$ CFU of *F. tularensis* LVS in 50 μl saline (frozen stock culture was thawed and re-suspended at the indicated and verified viable CFU dose in 50 μl saline). At 3-d post-challenge, the challenged mice were euthanized and the *F. tularensis* burdens ($\log_{10}$ CFU/organ) in the lungs and spleen were determined by plating serially diluted tissue extracts on cysteine heart agar (Becton Dickinson and Co, Sparks, Md., USA) supplemented with 1% (w/v) haemoglobin (Becton Dickinson), 0.1% (v/v) reconstituted IsoVitalex$^R$ enrichment (Becton Dickinson), 40 mg/l sulfamethoxazole, and 8 mg/l trimethoprim as described elsewhere (Conlan et al., 2003). The bacterial colonies were enumerated after 3 days incubation at 37° C. Statistical analyses of the mean bacterial burdens in the lungs or the spleen of the different groups of mice was done by one-way analyses of variance (ANOVA), followed by Newman-Keuls multiple comparison test. Values are considered to be statistically significant if p<0.05. The remaining 5 mice in each immunized group were similarly challenged at 77 d with $2.0 \times 10^5$ CFU of F. tularensis LVS, and the pathogen burdens in lungs and spleen were determined and statistically analyzed as described for the challenge at 35 d.

The results showed (FIG. 19A) that the anti-LVSCE IgA antibody responses in the vaginal wash and serum samples, and the anti-LVSCE IgG antibody responses in sera of the group of mice immunized with the LVSCE/Ms AMVAD-ANW-SR formulation were higher than the corresponding responses observed in the group immunized with LVSCE/ saline (antigen alone, no adjuvant). In another similar experiment, immunization with LVSCE/Ms AMVAD-ANW-SR formulation at 0.5 µg LVSCE dose in 0.2 mg AMVAD lipid was also observed to elicit relatively comparable LVSCE-specific immune responses in mice. There were no measurable LVSCE-specific antibody responses in the group sham-immunized with saline only. The results of the i.n. challenge at 35 d demonstrated that the mean F. tularensis burden in the lungs from LVSCE/Ms AMVAD-ANR-SR immunized mice showed substantially, although not statistically significant, lower pathogen burdens than the lungs from mice immunized with antigen alone (LVSCE/saline). The spleens from the group immunized with the LVSCE/Ms AMVAD-ANR-SR vaccine had significantly lower pathogen burdens (both p<0.01) than in the spleens from the groups immunized with the antigen (LVSCE) only or sham-immunized with saline (FIG. 19B). Similarly, the challenge at 77 d confirmed the protective efficacy of the AMVAD vaccine. The pathogen burdens in the lungs and spleen in the LVSCE/Ms AMVAD-ANR-SR vaccinated group were significantly (p<0.001 and p<0.05, respectively) lower (generally about 10-fold lower) than those in the corresponding organs from the LVSCE/ saline group and saline group (FIG. 19C).

In another experiment, groups of Balb/c (n=10) mice were intranasally immunized at 0, 7 and 21 d as described above, with 1 µg LVSCE in saline or 1 µg LVSCE/Ms AMVAD-ANW-SR formulation which was prepared exactly as described above. A control group was similarly sham-immunized with saline. The immune responses at 28 d, in the groups of mice in this experiment were similar to those shown for the experiment just above. At 35 d, all mice were intranasally challenged with $2.8 \times 10^5$ CFU of F. tularensis LVS as described above. The body weights of the challenged mice were recorded once a day and the mice were clinically evaluated at least twice daily. The clinical scores assigned were 0 (normal; healthy, active, lively), 1 (slightly sick; slightly ruffled fur, otherwise normal), 2 (sick; ruffled fur, slow movement, some hunching), 3 (very sick; ruffled fur, very slow movement, hunched, eyes squeezed). Mice that showed signs of irreversible morbidity (exhibiting a clinical score of 3, or a loss of >20% of their pre-challenge body weight, or a clinical score of 2 in combination with >than 20% loss of their pre-challenge body weight) were euthanized and were counted as having survived the day they were euthanized. It was observed that none of the mice in the groups immunized with saline or LVSCE/saline, survived beyond 5 and 6 d, respectively, post challenge (FIG. 20). In contrast, 90% and 70% of the mice immunized with the LVSCE/Ms AMVAD-ANW-SR vaccine were alive at 8 d and 10 d post challenge, respectively (FIG. 20). This example further demonstrates the protective efficacy of LVSCE/Ms AMVAD-ANW-SR vaccination, where the LVSCE/AMVAD immunized mice had prolonged survival outcome compared with the LVSCE/saline or the saline immunized groups.

REFERENCES

1. Alpar, H. O. and Brown, M. R. W. (1992) Effectiveness of liposomes as adjuvants of orally and nasally administered tetanus toxoid. Int. J. Pharm. 88:335-344.
2. Arakawa, T., Chong, D. K., and Langridge, W. H. (1998) Efficacy of a food plant-based oral cholera toxin B subunit vaccine. Nature Biotechnol. 16:292-297.
3. Baca-Estrada, M. E. Foldvari, M., Snider, M., Harding, K., Kournikakis, B., Babiuk, L. A., and Griebel, P. (2000) Intranasal immunization with liposome-formulated Yersinia pestis vaccine enhances mucosal immune responses. Vaccine 18:2203-2211.
4. Bracho, G., Lastre, M., Campo, J., Zayas, C., Gonzales, D., Gil, D., Acevedo, R., Taboada, C., Solis, R. L., and Perez, O. (2006) Proteoliposome derived cochleate as novel adjuvant. Vaccine, 24S2:30-31.
5. Campo, J., Lastre, M., Bracho, G., Rodriguez, T., Gil, D., Zayas, C., Taboada, C., Acevedo, R., Perez, D. R., and Perez, O. (2006) Immunological evaluation of bacterial derived cochleate and proteoliposome as mucosal adjuvants. Vaccine, 24S2:50-51.
6. Carol, H., and Nieto, A. (1998) A mucosal IgA response, but no systemic antibody response, is evoked by intranasal immunization of dogs with Echinococcus granulosus surface antigens iscoms. Veterinary Immunol. Immunopathol. 65:29-41.
7. Choquet, C. G., Patel, G. B., Beveridge, T. J., and G. D. Sprott. (1994) Stability of pressure-extruded liposomes made from archaeobacterial ether lipids. Appl. Microbiol. Biotechnol. 42:375-384.
8. Conlan, J. W., Cox, A. D., KuoLee, R., Webb, A., and Perry, M. B. (1999) Parenteral immunization with a glycoconjugate vaccine containing the O157 antigen of Escherichia coli O157:H7 elicits a systemic humoral immune response in mice, but fails to prevent colonization by the pathogen. Can. J. Microbiol. 45:279-286.
9. Conlan, J. W., Krishnan, L., Willick, G., Patel, G. B., and Sprott, G. D. (2001) Immunization of mice with lipopeptide antigens encapsulated in novel liposomes prepared from the polar lipids of various Archaeobacteria elicits rapid and prolonged specific protective immunity against infection with the facultative intracellular pathogen, Listeria monocytogenes. Vaccine 19:3509-3517.
10. Conlan, J. W., Sjostedt, A., and North, R. J. (1994) CD4$^+$ and CD8$^+$ T-cell-dependent and—independent host defense mechanisms can operate to control and resolve primary and secondary Francisella tularensis LVS infection in mice. Infect. Immun. 62:5603-5607.
11. Davis, S. S. (2001) Nasal vaccines. Adv. Drug Del. Rev. 51:21-42.
12. De, B. K., Sampson, J. S., Ades, E. W., Huebner, R. C., Jue, D. L., Johnson, S. E., Espina, M., Stinson, A. R., Briles, D. E., and Carlone, G. M. (2000) Purification and characterization of Streptococcus pneumoniae palmitoylated pneumococcal surface adhesin A expressed in Escherichia coli. Vaccine, 8:1811-1821.
13. de Haan, A., Geerligs, H. J., Huchshorn, J. P., van Scharrenburg, G. J. M, Palache, A. M., and Wilschut, J. (1995)

Mucosal immunoadjuvant activity of liposomes: induction of systemic IgG and secretory IgA responses in mice by intranasal immunization with an influenza subunit vaccine and coadministered liposomes. Vaccine, 13:155-162.

14. Gould-Fogerite, S., and Mannino, R. J. (1996) Mucosal and systemic immunization using cochleate and liposome vaccines. J. Liposome Res. 6:357-379.

15. Gould-Fogerite, S., and Mannino, R. J. (2000) Cochleates for induction of mucosal and systemic immune responses. In: D. T. O'Hagan (ed)., Vaccine adjuvants: Preparation methods and research protocols, pp 179-196, Humana Press, Inc., NJ.

16. Gould-Fogerite, S., and Mannino, R. J. (1997) Protein- or peptide-cochleate vaccines and method of immunizing using the same. U.S. Pat. No. 5,643,574.

17. Gould-Fogerite, S., Kheiri, M. T., Zhang, F., Wang, Z., Scolpino, A. J., Feketeova, E., Canki, M., and Mannino, R. J. (1998) Targeting immune response induction with cochleate and liposome-based vaccines. Advanced Drug Delivery Rev. 32:273-287.

18. Gould-Fogerite, S, and Mannino, R. J. (1999) Cochleate delivery vehicles. U.S. Pat. No. 5,994,318.

19. Gould-Fogerite, S., and Mannino, R. J. (1993) Preparation of large unilamellar liposomes with high entrapment yield by rotary dialysis or agarose plug diffusion. In: G. Gregoriadis (ed)., Liposome technology Volume 1, 2nd edition, pp 68-80, CRC Press, Inc., Boca Raton, USA.

20. Harokopakis, E., Hajishengallis, G., and Michalek, S. M. (1998) Effectiveness of liposomes possessing surface-linked recombinant B subunit of cholera toxin as an oral antigen delivery system. Infect. Immun. 66:4299-4304.

21. Henkart, P.A. (1997) CTL effector functions. Semin. Immunol. 9:85-86.

22. Holmgren, J., Czerkinsky, C., Eriksson, K., and Mharandi, A. (2003) Mucosal immunization and adjuvants: a brief overview of recent advances and challenges. Vaccine, 21:S2/89-95.

23. Jakobsen, H., and Jonsdottir, I. (2003) Mucosal vaccination against encapsulated respiratory bacteria—new potentials for conjugate vaccines? Scandinavian J. Immunol. 58:119-128.

24. Jin, T. (2004) Cochleates without metal cations as the bridging agents. PCT International publication #WO 2004/0112709 A1.

25. Jin, T., Zarif, L., and Mannino, R E. J. (2000) Nanocochleate formulations, process of preparation and method of delivery of pharmaceutical agents. U.S. Pat. No. 6,153,217.

26. Kates, M. (1992) Archaebacterial lipids: structure, biosynthesis and function. Biochem. Soc. Symp. 58: 51-72.

27. Kates, M., Moldoveanu, N., and Stewart, L.C. (1993) On the revised structure of the major phospholipid of Halobacterium salinarum. Biochim. Biophys. Acta 1169:46-53.

28. Kemble, G., and Greenberg, H. (2003) Novel generations of influenza vaccines. Vaccine 21:1789-1795.

29. Krishnan, L. and Mosmann, T. R. (1998) Functional subpopulation of CD4+ T lymphocytes. In: I. Kimber and M. K. Selgrade, (ed.), T lymphocyte subpopulations in immunotoxicology, pp 7-32, John Wiley & Sons, USA.

30. Lauterslager, T. G. M., Stok, W., and Hilgers, L. A. T. (2003) Improvement of systemic prime/oral boost strategy for systemic and local responses. Vaccine 21:1391-1399.

31. Lee, A., O'Rourke, J., De Ungria, M. C., Robertson, B., Daskalopoulos, G., and Dixon, M. F. (1997) A standardized mouse model of Helicobacter pylori infection: introducing the Sydney strain. Gastroenterology, 112:1386-1397.

32. Lemoine, D., Francotte, M., and Preat, V. (1998) Nasal vaccines. From fundamental concepts to vaccine development. S.T.P. Pharma Sciences 8(1):5-18.

33. Mannino, R. J., and Gould-Fogerite, S. (1998) Stabilizing and delivery means of biological molecules. U.S. Pat. No. 5,840,707.

34. Marra, A., Lawson, S., Asundi, J. S., Brigham, D., and Hromockyj, A. E. (2002) In vivo characterization of the psa genes from Streptococcus pneumoniae in multiple models of infection. Microbiology, 148::1483-1491.

35. Margolis, D., Gould-Fogerite, S., and Mannino, R. J. (2002) Integrative protein-DNA cochleate formulations and methods for transforming cells. U.S. Pat. No. 6,340,591.

36. McElrath, M. J. (1995) Selection of potent immunological adjuvants for vaccine construction. Seminars in Cancer Biology 6:375-385.

37. Mestecky, J., Moldoveanu, Z., Michalek, S. M., Morrow, C. D., Compans, R. W., Schafer, D. P., and Russell, M. W. (1997) Current opinions for vaccine delivery systems by mucosal routes. J. Controlled Release 48:243-257.

38. Neutra, M. R., and Kozlowski, P. A. (2006) Mucosal vaccines: the promise and the challenge. Nature Reviews Immunology, 6:148-158.

39. Ogra, P. L., Faden, H., and Welliver, R. C. (2001) Vaccination strategies for mucosal immune responses. Clinical Microbiol. Rev. 14(2):430-445.

40. O'Hagan, D. T. (1998) Microparticles and polymers for the mucosal delivery of vaccines. Advanced Drug Del. Rev. 34:305-320.

41. Papahadjopoulos, D. (1978) Large unilamellar vesicles (LUV) and method of preparing same. U.S. Pat. No. 4,078,052.

42. Papahadjopoulos, D., Vail, W. J., Jacobson, K., and Poste, G. (1975) Cochleate lipid cylinders: formation by fusion of unilamellar lipid vesicles. Biochimica Biophysica Acta, 394:483-491.

43. Papahadjopoulos, D., Vail, W. J., Newton, C., Nir, S., Jacobson, K., Poste, G., and Lazo, R. (1977) Studies on membrane fusion. III. The role of calcium-induced phase changes. Biochimica Biophysica Acta, 465:579-598.

44. Patel, G. B. and Chen, W. (2005) Archaeosome immunostimulatory vaccine delivery system. Current Drug Delivery 2:407-421.

45. Patel G. B., and Sprott, G. D. (1999) Archaeobacterial ether lipid liposomes (Archaeosomes) as novel vaccine and drug delivery systems. Critical Rev. Biotechnol. 19(4): 317-357.

46. Perez, O., Bracho, G., Lastre, M., Zayas, C., Gonzalez, D., Gil, D., Campo, J., Acevedo, R., Taboada, C., Rodriguez, T., Fajardo, M. E., Sierra, G., Campa, C., Mora, N., Barbera, R., and Solis, R. L. (2006) Proteoliposome-derived cochleate as an immunomodulator for nasal vaccine. Vaccine, 24S2:52-53.

47. Perry, M. B., MacLean, L., and Griffith, D. W. (1986) Structure of the O-chain polysaccharide of the phenol-phase soluble lipopolysaccharide of Escherichia coli O157:H7. Biochem. Cell Biol. 64:21-28.

48. Rubido, J. C. A., et al. (2002) Immunopotentiating formulations for vaccinal use. U.S. Pat. No. 6,355,414 B1.

49. Ryan, E. J., Daly, L. M., and Mills, K. H. G. (2001) Immunomodulators and delivery systems for vaccination by mucosal routes. Trends in Biotechnol. 19:293-304.

50. Singh, M., and O'Hagan, D. T. (2002) Recent advances in vaccine adjuvants. Pharmaceutical Res. 19:715-728.

51. Sprott, G. D. (1992) Structures of archaebacterial membrane lipids. J. Bioenrg. Biomembr. 24: 555-566.

52. Sprott, G. D., Krishnan, L., Conlan, W., Omri, A., and Patel, G. B. (2001) Archaeosomes as immunomodulating carriers for acellular vaccines to induce cytotoxic T lymphocyte (CTL) responses and protect the vaccinated host against intracellular pathogens and cancer. PCT International Publication No. WO 01/26683 A2.
53. Sprott, G. D., Patel, G. B., and Krishnan, L. (2003) Archaeobacterial ether lipid liposomes as vaccine adjuvants. Methods Enzymol. 373:155-172.
54. Sprott, G. D., Patel, G. B., Makabi-Panzu, B., and Tolson, D. L. (2000) Archaeosomes, archaeosomes containing coenzyme $Q_{10}$, and other types of liposomes containing $Q_{10}$ as adjuvants and as delivery vehicles. U.S. Pat. No. 6,132,789.
55. Szoka, F., and Papahadjopoulos, D. (1978) Procedure for preparing of liposomes with large internal aqueous space and high capture by reverse-phase evaporation. Proc. Natl. Acad. Sci. USA, 75:4194-4198.
56. Vadolas, J., Davies, J. K., Wright, P. J., and Strugnell, R. A. (1995) Intranasal immunization with liposomes induces strong mucosal immune responses in mice. Eur. J. Immunol. 25:969-975.
57. Wessel, D., and Flugge, U. I. (1984) A method for the quantitative recovery of protein in dilute solution in the presence of detergents and lipids. Anal. Biochem. 138:141-143.
58. Yuki, Y., and Kiyono, H. (2003) New generation of mucosal adjuvants for the induction of protective immunity. Rev. Med. Virol. 13:293-310.
59. Zarif, L., Jin, T., Segarra, I., and Mannino, R. J. 2001. Cochleate formulations and their use for the delivery of biologically relevant molecules. PCT International Publication No. WO 01/52817 A3.
60. Zarif, L., Jin, T., Segarra, I., and Mannino, R. J. (2003) Hydro-gel associated cochleate formulations and their use for the delivery of biologically relevant molecules. U.S. Pat. No. 6,592,894 B1; 2003;
61. Zarif, L., and Tan, F. (2003) Cochleates made with purified soy phosphatidylserine. US patent application publication #2003/0219473 A1

---

The invention claimed is:

1. A composition comprising an antigen and an archaeal polar lipid mucosal vaccine adjuvent and delivery (AMVAD) structure, wherein the AMVAD structure comprises multivalent cations and a plurality of aggregates of spherical archaeal polar lipid structures containing aqueous compartments, wherein the archaeal polar lipid is a total polar lipids extract or archaetidyl glycerophosphate-O-methyl, obtained from an archaeal species.

2. The composition according to claim 1, wherein the archaeal polar lipid is a total polar lipids extract.

3. The composition according to claim 2, wherein the multivalent cations are divalent or trivalent cations.

4. The composition according to claim 3, wherein the multivalent cations are divalent cations $Ca^{2+}$ or $Mg^{2+}$, or trivalent cation $Al^{3+}$.

5. The composition according to claim 4, wherein the divalent cations are $Ca^{2+}$.

6. The composition according to claim 5, wherein the $Ca^{2+}$ is provided as $CaCl_2$.

7. The composition according to claim 4, wherein the $Al^{3+}$ is provided as $AlCl_3$ or $AlK(SO_4)_2$.

8. The composition according to claim 3, wherein the archaeal species is selected from the group consisting of *Methanobrevibacter smithii*, *Halobacterium salinarum*, and *Thermoplasma acidophilum*.

9. The composition according to claim 2, wherein the total polar lipids extract from an archaeal species is mixed with neutral lipids from the archaeal species.

10. The composition according to claim 1, wherein the archaeal polar lipid is archaetidyl glycerophosphate-O-methyl obtained from *Halobacterium salinarum*.

11. The composition according to claim 10, wherein the multivalent cations are $Ca^{2+}$ provided as $CaCl_2$.

12. The composition according to claim 2, wherein the antigen is selected from the group consisting of a mixture of antigens, only a single purified antigen, a water soluble antigen, a hydrophobic antigen, a protein, a peptide, a carbohydrate-protein conjugate, a component extracted from a pathogen, and an antigen obtained by a recombinant method.

13. The composition according to claim 12, wherein the antigen is a component extracted from a pathogen, wherein the pathogen is selected from the group consisting of *Listeria monocytogenes, Francisella tularensis*, and *Helicobacter pylori*.

14. The composition according to claim 12, wherein the antigen is selected from the group consisting of protein, peptide, carbohydrate-protein conjugate.

15. The composition according to claim 2, wherein the AMVAD structure has an average width in the range of 1-5 µm.

16. The composition according to claim 2, wherein the archaeal species is *Methanobrevibacter smithii*.

17. A method of producing a composition for administration to an animal, said composition comprising an antigen and an archaeal polar lipid mucosal vaccine adjuvent and delivery (AMVAD) structure, wherein the AMVAD structure comprises multivalent cations and a plurality of aggregates of spherical archaeal polar lipid structures containing aqueous compartments, wherein the archaeal polar lipid is a total polar lipids extract obtained from an archaeal species; said method comprising the following steps:
- a) preparing unilamellar archaeosomes from a total polar lipids extract obtained from an archaeal species, with said antigen, at a pH above the pI of the antigen, to form an archaeosome suspension;
- b) adding multivalent cations to the archaeosome suspension, without prior removal of un-encapsulated antigen, in sufficient amount and in proportion to the archaeal polar lipid to form said AMVAD structures characterized by aggregates of a plurality of spherical structures containing aqueous compartments;
- c) re-suspending the AMVAD structures in physiological saline (0.85% NaCl, at pH 7.1) supplemented with sufficient quantity of the multivalent cations as in the adding step, to maintain integrity of the AMVAD structures; and
- d) just prior to administration to an animal, diluting the re-suspended AMVAD structures to the required administration dose in a final concentration of physiological saline of 0.85% NaCl, at pH 7.1 and the multivalent cation of the adding step, to maintain integrity of the AMVAD structures.

18. The method of claim 17, wherein the unilamellar archaeosomes prepared in step a) are prepared in absence of the antigen and the antigen is then admixed, at a pH above the pI of the antigen, with the archaeosome suspension prior to continuing with step b).

19. A method of eliciting an antigen-specific immune response in an animal, comprising administering the composition of claim 2 to the animal, wherein the response which affords the animal protection against the effects of a specific disease or infection by a pathogen, and wherein the specific disease or pathogen against which protection is afforded is predicated by the specific antigen selected in making the composition.

20. The method of claim 19, wherein the composition is administered to the animal by a route selected from the group consisting of a systemic route and a mucosal route.

21. The method of claim 20, wherein the mucosal route is an intranasal route.

22. The method of claim 19, wherein the elicited antigen-specific immune response comprises a systemic immune response,
wherein the elicited systemic immune response is characterized by the elicitation of a cell-mediated immune response comprising an antigen-specific MHC class I-restricted $CD8^+$ cytotoxic T lymphocyte response, and an antigen-specific MHC class II-restricted response comprising a humoral antibody response,
wherein the antigen-specific humoral antibody response is characterized by the elicitation of antigen-specific serum IgG, IgG1 and IgG2a antibody response.

23. The method of claim 21, wherein the elicited antigen-specific immune response comprises an antigen-specific mucosal immune response and an antigen-specific systemic immune response,
wherein the mucosal immune response is characterized by an antigen-specific IgA antibody response at mucosal sites, and the systemic immune response is characterized by a cell-mediated immune response comprising an antigen-specific MHC class I-restricted $CD8^+$ cytotoxic T lymphocyte response, and an antigen-specific MHC class II-restricted response comprising a humoral antibody response comprising antigen-specific serum IgG, IgG1 and IgG2a response.

* * * * *

SEQUENCE LISTING

```
<160> NUMBER OF SEQ ID NOS: 2

<210> SEQ ID NO 1
<211> LENGTH: 20
<212> TYPE: PRT
<213> ORGANISM: Listeria monocytogenes
<220> FEATURE:
<221> NAME/KEY: Hyl
<222> LOCATION: (1)..(1)
<220> FEATURE:
<221> NAME/KEY: Palmitate
<222> LOCATION: (1)..(1)
<220> FEATURE:
<221> NAME/KEY: Palmitate
<222> LOCATION: (1)..(1)
<220> FEATURE:
<221> NAME/KEY: Hyl
<222> LOCATION: (20)..(20)

<400> SEQUENCE: 1

Lys Ser Ser Lys Gly Tyr Lys Asp Gly Asn Glu Tyr Ile Val Val Glu
1               5                   10                  15

Lys Lys Lys Lys
            20

<210> SEQ ID NO 2
<211> LENGTH: 300
<212> TYPE: PRT
<213> ORGANISM: Streptococcus pneumoniae

<400> SEQUENCE: 2

Ala Ser Gly Lys Lys Asp Ala Ala Ser Gly Gln Lys Leu Lys Val Val
1               5                   10                  15

Ala Thr Asn Ser Ile Ile Ala Asp Ile Thr Lys Asn Ile Ala Gly Asp
                20                  25                  30

Lys Ile Asp Leu His Ser Ile Val Pro Ile Gly Gln Asp Pro His Glu
            35                  40                  45

Tyr Glu Pro Leu Pro Glu Asp Val Lys Lys Thr Ser Glu Ala Asp Leu
        50                  55                  60

Ile Phe Tyr Asn Gly Ile Asn Leu Glu Thr Gly Gly Asn Ala Trp Phe
65                  70                  75                  80

Thr Lys Leu Val Glu Asn Ala Lys Lys Thr Glu Asn Lys Asp Tyr Phe
```

-continued

```
                        85                  90                      95
Ala Val Ser Asp Gly Val Asp Val Ile Tyr Leu Glu Gly Gln Asn Glu
            100                 105                 110

Lys Gly Lys Glu Asp Pro His Ala Trp Leu Asn Leu Glu Asn Gly Ile
        115                 120                 125

Ile Phe Ala Lys Asn Ile Ala Lys Gln Leu Ser Ala Lys Asp Pro Asn
    130                 135                 140

Asn Lys Glu Phe Tyr Glu Lys Asn Leu Lys Glu Tyr Thr Asp Lys Leu
145                 150                 155                 160

Asp Lys Leu Asp Lys Glu Ser Lys Asp Lys Phe Asn Lys Ile Pro Ala
            165                 170                 175

Glu Lys Lys Leu Ile Val Thr Ser Glu Gly Ala Phe Lys Tyr Phe Ser
            180                 185                 190

Lys Ala Tyr Gly Val Pro Ser Ala Tyr Ile Trp Glu Ile Asn Thr Glu
        195                 200                 205

Glu Glu Gly Thr Pro Glu Gln Ile Lys Thr Leu Val Glu Lys Leu Arg
        210                 215                 220

Gln Thr Lys Val Pro Ser Leu Phe Val Glu Ser Ser Val Asp Asp Arg
225                 230                 235                 240

Pro Met Lys Ala Val Ser Gln Asp Thr Asn Ile Pro Ile Tyr Ala Gln
                245                 250                 255

Ile Phe Thr Asp Ser Ile Ala Glu Gln Gly Lys Glu Gly Asp Ser Tyr
            260                 265                 270

Tyr Ser Met Met Lys Tyr Asn Leu Asp Lys Ile Ala Glu Gly Leu Ala
            275                 280                 285

Lys Gly Gly Gly Gly Ser His His His His His
    290                 295                 300
```